US012723063B2

(12) United States Patent
Alsina-Fernandez et al.

(10) Patent No.: US 12,723,063 B2
(45) Date of Patent: Sep. 1, 2026

(54) GIPR-AGONIST COMPOUNDS

(71) Applicant: Eli Lilly and Company, Indianapolis, IN (US)

(72) Inventors: Jorge Alsina-Fernandez, Indianapolis, IN (US); Andrea Renee Geiser, Greenwood, IN (US); Lili Guo, Carmel, IN (US); Samantha Grace Lyons Keyser, Carmel, IN (US); John Lee, Carmel, IN (US); Hongchang Qu, Carmel, IN (US); William Christopher Roell, Avon, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 18/390,877

(22) Filed: Dec. 20, 2023

(65) Prior Publication Data

US 2024/0218031 A1 Jul. 4, 2024

Related U.S. Application Data

(63) Continuation of application No. 17/573,317, filed on Jan. 11, 2022, now Pat. No. 11,897,926, which is a continuation of application No. 16/941,990, filed on Jul. 29, 2020, now Pat. No. 11,254,721.

(60) Provisional application No. 62/881,685, filed on Aug. 1, 2019.

(51) Int. Cl.
*C07K 14/47* (2006.01)
*A61K 38/00* (2006.01)

(52) U.S. Cl.
CPC .......... *C07K 14/4703* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 11,254,721 | B2 * | 2/2022 | Alsina-Fernandez | A61P 3/10 |
| 11,897,926 | B2 * | 2/2024 | Alsina-Fernandez | A61P 3/10 |
| 2015/0299281 | A1 * | 10/2015 | Just | A61P 43/00 530/324 |
| 2018/0155407 | A1 * | 6/2018 | Bossart | C07K 14/605 |
| 2020/0024322 | A1 * | 1/2020 | Abraham | A61K 9/4858 |

FOREIGN PATENT DOCUMENTS

| | | | | |
|---|---|---|---|---|
| WO | WO-2016066744 A2 * | 5/2016 | | A61K 38/00 |
| WO | WO 2019/125929 * | 6/2019 | | |

OTHER PUBLICATIONS

Finan et al. ('Unimolecular dual incretins maximize metabolic benefits in rodents, monkeys and humans' Science Translational Medicine v5(209) Oct. 30, 2013 pp. 1-17) (Year: 2013).*
Finan supplement (Supplement to 'Unimolecular dual incretins maximize metabolic benefits in rodents, monkeys and humans' Science Translational Medicine v5(209) Oct. 30, 2013 pp. 1-8) (Year: 2013).*

* cited by examiner

*Primary Examiner* — Ronald T Niebauer
(74) *Attorney, Agent, or Firm* — Charles H. Rexer

(57) ABSTRACT

The present invention relates to compounds having activity at the human glucose-dependent insulinotropic polypeptide (GIP) receptor. The present invention also relates to compounds having an extended duration of action at the GIP receptor. Such compounds may be useful in the treatment of diabetes, including type 2 diabetes mellitus ("T2DM"). Also, the compounds may be useful in the treatment of obesity.

4 Claims, No Drawings

Specification includes a Sequence Listing.

SEQUENCE LISTING

```
Sequence total quantity: 126
SEQ ID NO: 1           moltype = AA  length = 42
FEATURE                Location/Qualifiers
MOD_RES                42
                       note = AMIDATION
source                 1..42
                       mol_type = protein
                       organism = Homo sapiens
SEQUENCE: 1
YAEGTFISDY SIAMDKIHQQ DFVNWLLAQK GKKNDWKHNI TQ                    42

SEQ ID NO: 2           moltype = AA  length = 30
FEATURE                Location/Qualifiers
MOD_RES                30
                       note = AMIDATION
source                 1..30
                       mol_type = protein
                       organism = Homo sapiens
SEQUENCE: 2
HAEGTFTSDV SSYLEGQAAK EFIAWLVKGR                                  30

SEQ ID NO: 3           moltype = AA  length = 29
FEATURE                Location/Qualifiers
source                 1..29
```

-continued

```
                        mol_type = protein
                        organism = Homo sapiens
SEQUENCE: 3
HSQGTFTSDY SKYLDSRRAQ DFVQWLMNT                                      29

SEQ ID NO: 4            moltype = AA  length = 39
FEATURE                 Location/Qualifiers
REGION                  1..39
                        note = Synthetic Construct
MOD_RES                 1
                        note = The N-terminus of Xaa at position 1 is modified with
                         Z1, wherein the modification is selected from the group
                         consisting of acetyl and absent.
VARIANT                 1
                        note = Xaa at position 1 is Y or D-Tyr
VARIANT                 2
                        note = Xaa at position 2 is A, Aib, or D-Ala
VARIANT                 6
                        note = Xaa at position 6 is F, alpha-methyl-Phe, Iva, L,
                         alpha-methyl-Leu, or alpha-methyl-Phe(2F)
VARIANT                 13
                        note = Xaa at position 13 is alpha-methyl-Leu, A, L or Aib
VARIANT                 16
                        note = Xaa at position 16 is K, E, or Orn
VARIANT                 17
                        note = Xaa at position 17 is I or K
MOD_RES                 17
                        note = When Xaa at position 17 is K, then K is chemically
                         modified by conjugation of the epsilon-amino group of the
                         Lys side chain with
                         K(2-[2-(2-amino-ethoxy)-ethoxy]-acetyl)2-gamma-Glu-CO-(CH2)
                         q-CO2H , wherein q=16 or 18
REGION                  17..26
                        note = MISC_FEATURE - wherein one and only one selected
                         from the group consisting of X17 and X26 is
                         K(2-[2-(2-amino-ethoxy)-ethoxy]-acetyl)2-(gamma-Glu)-CO-(CH
                         2)q-CO 2H
VARIANT                 18
                        note = Xaa at position 18 is H, A or R
VARIANT                 20
                        note = Xaa at position 20 is Aib or Q
VARIANT                 21
                        note = Xaa at position 21 is D or E
VARIANT                 22
                        note = Xaa at position 22 is F or alpha-methyl-Phe
VARIANT                 24
                        note = Xaa at position 24 is E, N, Q or D-Glu
VARIANT                 25
                        note = Xaa at position 25 is Y, 4-Pal, W or alpha-methyl-Tyr
VARIANT                 26
                        note = Xaa at position 26 is K or L
MOD_RES                 26
                        note = When Xaa at position 26 is K, then K is chemically
                         modified by conjugation of the epsilon-amino group of the
                         Lys side chain with
                         K(2-[2-(2-amino-ethoxy)-ethoxy]-acetyl)2-gamma-Glu-CO-(CH2)
                         q-CO2H , wherein q=16 or 18
VARIANT                 28
                        note = Xaa at position 28 is E or A
VARIANT                 29
                        note = Xaa at position 29 is A, G, Q or T
MOD_RES                 39
                        note = The C-terminus of Xaa at position 39 is modified
                         with Z2, wherein Z2 is absent or the modification is
                         amidation.
source                  1..39
                        mol_type = protein
                        organism = synthetic construct
SEQUENCE: 4
XXEGTXISDY SIXLDXXXQX XXVXXXLXXG PSSGAPPPS                           39

SEQ ID NO: 5            moltype = AA  length = 39
FEATURE                 Location/Qualifiers
REGION                  1..39
                        note = Synthetic Construct
SITE                    2
                        note = MISC_FEATURE - Xaa at position 2 is D-Ala
MOD_RES                 17
                        note = Lys at position 17 is chemically modified by
```

```
                        conjugation of the epsilon-amino group of the Lys side
                        chain with
                        (2-[2-(2-amino-ethoxy)-ethoxy]-acetyl)2-(gamma-Glu)-CO-(CH2
                        )18-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 5
YXEGTFISDY SILLDKKAQX DFVNWLLAQG PSSGAPPPS                        39

SEQ ID NO: 6            moltype = AA  length = 39
FEATURE                 Location/Qualifiers
REGION                  1..39
                        note = Synthetic Construct
SITE                    2
                        note = MISC_FEATURE - Xaa at position 2 is D-Ala
MOD_RES                 17
                        note = Lys at position 17 is chemically modified by
                        conjugation of the epsilon-amino group of the Lys side
                        chain with
                        (2-[2-(2-amino-ethoxy)-ethoxy]-acetyl)2-(gamma-Glu)-CO-(CH2
                        )16-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 6
YXEGTFISDY SILLDKKAQX DFVNWLLAQG PSSGAPPPS                        39

SEQ ID NO: 7            moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                        conjugation of the epsilon-amino group of the Lys side
                        chain with
                        (2-[2-(2-amino-ethoxy)-ethoxy]-acetyl)2-(gamma-Glu)-CO-(CH2
                        )18-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 7
YXEGTFISDY SIXLDKKHQX DFVEXLLEAG PSSGAPPPS                        39

SEQ ID NO: 8            moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
SITE                    16
                        note = MISC_FEATURE - Xaa at position 16 is Orn
MOD_RES                 17
                        note = Lys at position 17 is chemically modified by
                        conjugation of the epsilon-amino group of the Lys side
                        chain with
                        (2-[2-(2-amino-ethoxy)-ethoxy]-acetyl)2-(gamma-Glu)-CO-(CH2
                        )18-CO 2H
SITE                    20
```

```
                      note = MISC_FEATURE - Xaa at position 20 is Aib
SITE                  25
                      note = MISC_FEATURE - Xaa at position 25 is 4-Pal
MOD_RES               39
                      note = Ser at position 39 is amidated
source                1..39
                      mol_type = protein
                      organism = synthetic construct
SEQUENCE: 8
YXEGTFISDY SIXLDXKHQX DFVEXLLEAG PSSGAPPPS                        39

SEQ ID NO: 9          moltype = AA  length = 39
FEATURE               Location/Qualifiers
REGION                1..39
                      note = Synthetic Construct
SITE                  2
                      note = MISC_FEATURE - Xaa at position 2 is Aib
SITE                  13
                      note = MISC_FEATURE - Xaa at position 13 is alpha-methyl-Leu
SITE                  20
                      note = MISC_FEATURE - Xaa at position 20 is Aib
MOD_RES               26
                      note = Lys at position 26 is chemically modified by
                       conjugation of the epsilon-amino group of the Lys side
                       chain with
                       (2-[2-(2-amino-ethoxy)-ethoxy]-acetyl)2-(gamma-Glu)-CO-(CH2
                       )18-CO 2H
MOD_RES               39
                      note = Ser at position 39 is amidated
source                1..39
                      mol_type = protein
                      organism = synthetic construct
SEQUENCE: 9
YXEGTFISDY SIXLDKIHQX DFVEYKLEGG PSSGAPPPS                        39

SEQ ID NO: 10         moltype = AA  length = 39
FEATURE               Location/Qualifiers
REGION                1..39
                      note = Synthetic Construct
SITE                  2
                      note = MISC_FEATURE - Xaa at position 2 is Aib
SITE                  13
                      note = MISC_FEATURE - Xaa at position 13 is alpha-methyl-Leu
SITE                  16
                      note = MISC_FEATURE - Xaa at position 16 is Orn
SITE                  20
                      note = MISC_FEATURE - Xaa at position 20 is Aib
MOD_RES               26
                      note = Lys at position 26 is chemically modified by
                       conjugation of the epsilon-amino group of the Lys side
                       chain with
                       (2-[2-(2-amino-ethoxy)-ethoxy]-acetyl)2-(gamma-Glu)-CO-(CH2
                       )18-CO 2H
MOD_RES               39
                      note = Ser at position 39 is amidated
source                1..39
                      mol_type = protein
                      organism = synthetic construct
SEQUENCE: 10
YXEGTFISDY SIXLDXIHQX DFVEYKLEGG PSSGAPPPS                        39

SEQ ID NO: 11         moltype = AA  length = 39
FEATURE               Location/Qualifiers
REGION                1..39
                      note = Synthetic Construct
SITE                  2
                      note = MISC_FEATURE - Xaa at position 2 is Aib
SITE                  13
                      note = MISC_FEATURE - Xaa at position 13 is alpha-methyl-Leu
SITE                  16
                      note = MISC_FEATURE - Xaa at position 16 is Orn
SITE                  20
                      note = MISC_FEATURE - Xaa at position 20 is Aib
SITE                  24
                      note = MISC_FEATURE - Xaa at position 24 is D-Glu
MOD_RES               26
                      note = Lys at position 26 is chemically modified by
                       conjugation of the epsilon-amino group of the Lys side
                       chain with
```

-continued

```
                     (2-[2-(2-amino-ethoxy)-ethoxy]-acetyl)2-(gamma-Glu)-CO-(CH2
                     )16-CO 2H
MOD_RES             39
                    note = Ser at position 39 is amidated
source              1..39
                    mol_type = protein
                    organism = synthetic construct
SEQUENCE: 11
YXEGTFISDY SIXLDXIHQX EFVXYKLEGG PSSGAPPPS                         39

SEQ ID NO: 12       moltype = AA  length = 39
FEATURE             Location/Qualifiers
REGION              1..39
                    note = Synthetic Construct
SITE                2
                    note = MISC_FEATURE - Xaa at position 2 is Aib
MOD_RES             17
                    note = Lys at position 17 is chemically modified by
                     conjugation of the epsilon-amino group of the Lys side
                     chain with
                     (2-[2-(2-amino-ethoxy)-ethoxy]-acetyl)2-(gamma-Glu)-CO-(CH2
                     )18-CO 2H
SITE                20
                    note = MISC_FEATURE - Xaa at position 20 is Aib
MOD_RES             39
                    note = Ser at position 39 is amidated
source              1..39
                    mol_type = protein
                    organism = synthetic construct
SEQUENCE: 12
YXEGTFISDY SILLDKKAQX DFVNWLLAQG PSSGAPPPS                         39

SEQ ID NO: 13       moltype = AA  length = 39
FEATURE             Location/Qualifiers
REGION              1..39
                    note = Synthetic Construct
SITE                2
                    note = MISC_FEATURE - Xaa at position 2 is D-Ala
MOD_RES             17
                    note = Lys at position 17 is chemically modified by
                     conjugation of the epsilon-amino group of the Lys side
                     chain with
                     (2-[2-(2-amino-ethoxy)-ethoxy]-acetyl)2-(gamma-Glu)-CO-(CH2
                     )18-CO 2H
SITE                20
                    note = MISC_FEATURE - Xaa at position 20 is Aib
MOD_RES             39
                    note = Ser at position 39 is amidated
source              1..39
                    mol_type = protein
                    organism = synthetic construct
SEQUENCE: 13
YXEGTFISDY SILLDKKHQX DFVNWLLAQG PSSGAPPPS                         39

SEQ ID NO: 14       moltype = AA  length = 39
FEATURE             Location/Qualifiers
REGION              1..39
                    note = Synthetic Construct
SITE                2
                    note = MISC_FEATURE - Xaa at position 2 is D-Ala
MOD_RES             17
                    note = Lys at position 17 is chemically modified by
                     conjugation of the epsilon-amino group of the Lys side
                     chain with
                     (2-[2-(2-amino-ethoxy)-ethoxy]-acetyl)2-(gamma-Glu)-CO-(CH2
                     )18-CO 2H
MOD_RES             39
                    note = Ser at position 39 is amidated
source              1..39
                    mol_type = protein
                    organism = synthetic construct
SEQUENCE: 14
YXEGTFISDY SILLDKKHQQ DFVNWLLAGG PSSGAPPPS                         39

SEQ ID NO: 15       moltype = AA  length = 39
FEATURE             Location/Qualifiers
REGION              1..39
                    note = Synthetic Construct
SITE                2
```

-continued

```
                        note = MISC_FEATURE - Xaa at position 2 is D-Ala
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 15
YXEGTFISDY SILLDKKAQQ DFVNWLLAQG PSSGAPPPS                         39

SEQ ID NO: 16           moltype = AA  length = 39
FEATURE                 Location/Qualifiers
REGION                  1..39
                        note = Synthetic Construct
SITE                    2
                        note = MISC_FEATURE - Xaa at position 2 is D-Ala
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 16
YXEGTFISDY SILLDKKAQQ DFVNWLLAGG PSSGAPPPS                         39

SEQ ID NO: 17           moltype = AA  length = 39
FEATURE                 Location/Qualifiers
REGION                  1..39
                        note = Synthetic Construct
SITE                    2
                        note = MISC_FEATURE - Xaa at position 2 is D-Ala
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 17
YXEGTFISDY SILLDKKHQQ EFVNWLLAQG PSSGAPPPS                         39

SEQ ID NO: 18           moltype = AA  length = 39
FEATURE                 Location/Qualifiers
REGION                  1..39
                        note = Synthetic Construct
SITE                    2
                        note = MISC_FEATURE - Xaa at position 2 is D-Ala
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 18
YXEGTFISDY SILLDKKHQQ DFVEWLLAQG PSSGAPPPS                         39

SEQ ID NO: 19           moltype = AA  length = 39
FEATURE                 Location/Qualifiers
REGION                  1..39
                        note = Synthetic Construct
```

-continued

```
SITE                  2
                      note = MISC_FEATURE - Xaa at position 2 is D-Ala
MOD_RES               17
                      note = Lys at position 17 is chemically modified by
                       conjugation of the epsilon-amino group of the Lys side
                       chain with
                       (2-[2-(2-amino-ethoxy)-ethoxy]-acetyl)2-(gamma-Glu)-CO-(CH2
                       )18-CO 2H
MOD_RES               39
                      note = Ser at position 39 is amidated
source                1..39
                      mol_type = protein
                      organism = synthetic construct
SEQUENCE: 19
YXEGTFISDY SILLDKKHQQ DFVNYLLAQG PSSGAPPPS                         39

SEQ ID NO: 20         moltype = AA  length = 39
FEATURE               Location/Qualifiers
REGION                1..39
                      note = Synthetic Construct
SITE                  2
                      note = MISC_FEATURE - Xaa at position 2 is D-Ala
MOD_RES               17
                      note = Lys at position 17 is chemically modified by
                       conjugation of the epsilon-amino group of the Lys side
                       chain with
                       (2-[2-(2-amino-ethoxy)-ethoxy]-acetyl)2-(gamma-Glu)-CO-(CH2
                       )16-CO 2H
SITE                  20
                      note = MISC_FEATURE - Xaa at position 20 is Aib
MOD_RES               39
                      note = Ser at position 39 is amidated
source                1..39
                      mol_type = protein
                      organism = synthetic construct
SEQUENCE: 20
YXEGTFISDY SILLDKKAQX DFVEWLLAQG PSSGAPPPS                         39

SEQ ID NO: 21         moltype = AA  length = 39
FEATURE               Location/Qualifiers
REGION                1..39
                      note = Synthetic Construct
SITE                  2
                      note = MISC_FEATURE - Xaa at position 2 is D-Ala
MOD_RES               17
                      note = Lys at position 17 is chemically modified by
                       conjugation of the epsilon-amino group of the Lys side
                       chain with
                       (2-[2-(2-amino-ethoxy)-ethoxy]-acetyl)2-(gamma-Glu)-CO-(CH2
                       )16-CO 2H
SITE                  20
                      note = MISC_FEATURE - Xaa at position 20 is Aib
MOD_RES               39
                      note = Ser at position 39 is amidated
source                1..39
                      mol_type = protein
                      organism = synthetic construct
SEQUENCE: 21
YXEGTFISDY SILLDKKAQX DFVNWLLEQG PSSGAPPPS                         39

SEQ ID NO: 22         moltype = AA  length = 39
FEATURE               Location/Qualifiers
REGION                1..39
                      note = Synthetic Construct
SITE                  2
                      note = MISC_FEATURE - Xaa at position 2 is D-Ala
MOD_RES               17
                      note = Lys at position 17 is chemically modified by
                       conjugation of the epsilon-amino group of the Lys side
                       chain with
                       (2-[2-(2-amino-ethoxy)-ethoxy]-acetyl)2-(gamma-Glu)-CO-(CH2
                       )16-CO 2H
SITE                  20
                      note = MISC_FEATURE - Xaa at position 20 is Aib
SITE                  25
                      note = MISC_FEATURE - Xaa at position 25 is 4-Pal
MOD_RES               39
                      note = Ser at position 39 is amidated
source                1..39
```

-continued

```
                        mol_type = protein
                        organism = synthetic construct
SEQUENCE: 22
YXEGTFISDY SILLDKKAQX DFVNXLLAQG PSSGAPPPS                          39

SEQ ID NO: 23           moltype = AA  length = 39
FEATURE                 Location/Qualifiers
REGION                  1..39
                        note = Synthetic Construct
SITE                    2
                        note = MISC_FEATURE - Xaa at position 2 is D-Ala
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )16-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 23
YXEGTFISDY SILLDKKAQX DFVNWLLAGG PSSGAPPPS                          39

SEQ ID NO: 24           moltype = AA  length = 39
FEATURE                 Location/Qualifiers
REGION                  1..39
                        note = Synthetic Construct
SITE                    2
                        note = MISC_FEATURE - Xaa at position 2 is D-Ala
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )16-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 24
YXEGTFISDY SILLDKKAQX EFVNWLLAQG PSSGAPPPS                          39

SEQ ID NO: 25           moltype = AA  length = 39
FEATURE                 Location/Qualifiers
REGION                  1..39
                        note = Synthetic Construct
SITE                    2
                        note = MISC_FEATURE - Xaa at position 2 is Aib
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )16-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 25
YXEGTFISDY SIALDKKHQX DFVEXLLAGG PSSGAPPPS                          39

SEQ ID NO: 26           moltype = AA  length = 39
FEATURE                 Location/Qualifiers
REGION                  1..39
                        note = Synthetic Construct
SITE                    2
                        note = MISC_FEATURE - Xaa at position 2 is Aib
```

-continued

```
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )16-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 26
YXEGTFISDY SILLDKKHQX DFVEXLLAGG PSSGAPPPS                         39

SEQ ID NO: 27           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is alpha-methyl-Phe
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )16-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 27
YXEGTXISDY SIALDKKHQX DFVEXLLAGG PSSGAPPPS                         39

SEQ ID NO: 28           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is Aib
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )16-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 28
YXEGTFISDY SIXLDKKHQX DFVEXLLAGG PSSGAPPPS                         39

SEQ ID NO: 29           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is alpha-methyl-Phe
MOD_RES                 17
```

-continued

```
                      note = Lys at position 17 is chemically modified by
                       conjugation of the epsilon-amino group of the Lys side
                       chain with
                       (2-[2-(2-amino-ethoxy)-ethoxy]-acetyl)2-(gamma-Glu)-CO-(CH2
                       )18-CO 2H
SITE                  20
                      note = MISC_FEATURE - Xaa at position 20 is Aib
MOD_RES               39
                      note = Ser at position 39 is amidated
source                1..39
                      mol_type = protein
                      organism = synthetic construct
SEQUENCE: 29
YXEGTXISDY SIALDKKHQX EFVNWLLAGG PSSGAPPPS                        39

SEQ ID NO: 30         moltype = AA  length = 39
FEATURE               Location/Qualifiers
REGION                1..39
                      note = Synthetic Construct
SITE                  2
                      note = MISC_FEATURE - Xaa at position 2 is Aib
SITE                  6
                      note = MISC_FEATURE - Xaa at position 6 is
                       alpha-methyl-Phe(2F)
MOD_RES               17
                      note = Lys at position 17 is chemically modified by
                       conjugation of the epsilon-amino group of the Lys side
                       chain with
                       (2-[2-(2-amino-ethoxy)-ethoxy]-acetyl)2-(gamma-Glu)-CO-(CH2
                       )18-CO 2H
SITE                  20
                      note = MISC_FEATURE - Xaa at position 20 is Aib
MOD_RES               39
                      note = Ser at position 39 is amidated
source                1..39
                      mol_type = protein
                      organism = synthetic construct
SEQUENCE: 30
YXEGTXISDY SIALDKKHQX EFVNWLLAGG PSSGAPPPS                        39

SEQ ID NO: 31         moltype = AA  length = 39
FEATURE               Location/Qualifiers
REGION                1..39
                      note = Synthetic Construct
SITE                  2
                      note = MISC_FEATURE - Xaa at position 2 is D-Ala
MOD_RES               17
                      note = Lys at position 17 is chemically modified by
                       conjugation of the epsilon-amino group of the Lys side
                       chain with
                       (2-[2-(2-amino-ethoxy)-ethoxy]-acetyl)2-(gamma-Glu)-CO-(CH2
                       )16-CO 2H
SITE                  20
                      note = MISC_FEATURE - Xaa at position 20 is Aib
MOD_RES               39
                      note = Ser at position 39 is amidated
source                1..39
                      mol_type = protein
                      organism = synthetic construct
SEQUENCE: 31
YXEGTFISDY SILLDKKAQX EFVQWLLAGG PSSGAPPPS                        39

SEQ ID NO: 32         moltype = AA  length = 39
FEATURE               Location/Qualifiers
REGION                1..39
                      note = Synthetic Construct
SITE                  2
                      note = MISC_FEATURE - Xaa at position 2 is D-Ala
MOD_RES               17
                      note = Lys at position 17 is chemically modified by
                       conjugation of the epsilon-amino group of the Lys side
                       chain with
                       (2-[2-(2-amino-ethoxy)-ethoxy]-acetyl)2-(gamma-Glu)-CO-(CH2
                       )16-CO 2H
SITE                  20
                      note = MISC_FEATURE - Xaa at position 20 is Aib
MOD_RES               39
                      note = Ser at position 39 is amidated
source                1..39
```

-continued

```
                        mol_type = protein
                        organism = synthetic construct
SEQUENCE: 32
YXEGTFISDY SILLDKKAQX EFVNWLLEGG PSSGAPPPS                          39

SEQ ID NO: 33           moltype = AA  length = 39
FEATURE                 Location/Qualifiers
REGION                  1..39
                        note = Synthetic Construct
SITE                    2
                        note = MISC_FEATURE - Xaa at position 2 is D-Ala
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )16-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 33
YXEGTFISDY SILLDKKAQX EFVEWLLAGG PSSGAPPPS                          39

SEQ ID NO: 34           moltype = AA  length = 39
FEATURE                 Location/Qualifiers
REGION                  1..39
                        note = Synthetic Construct
SITE                    1
                        note = MISC_FEATURE - Xaa at position 1 is D-Tyr
MOD_RES                 1
                        note = The N-terminus of Xaa at position 1 is acetylated
SITE                    6
                        note = MISC_FEATURE - Xaa at position 6 is
                         alpha-methyl-Phe(2F)
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )16-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 34
XAEGTXISDY SIALDKKHQX EFVNYLLAGG PSSGAPPPS                          39

SEQ ID NO: 35           moltype = AA  length = 39
FEATURE                 Location/Qualifiers
REGION                  1..39
                        note = Synthetic Construct
SITE                    2
                        note = MISC_FEATURE - Xaa at position 2 is Aib
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )16-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 35
YXEGTFISDY SILLDKKHQX DFVNYLLAAG PSSGAPPPS                          39

SEQ ID NO: 36           moltype = AA  length = 39
FEATURE                 Location/Qualifiers
REGION                  1..39
```

-continued

```
                         note = Synthetic Construct
SITE                     2
                         note = MISC_FEATURE - Xaa at position 2 is D-Ala
MOD_RES                  17
                         note = Lys at position 17 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
                          )16-CO 2H
SITE                     20
                         note = MISC_FEATURE - Xaa at position 20 is Aib
MOD_RES                  39
                         note = Ser at position 39 is amidated
source                   1..39
                         mol_type = protein
                         organism = synthetic construct
SEQUENCE: 36
YXEGTLISDY SILLDKKAQX DFVNWLLAQG PSSGAPPPS                              39

SEQ ID NO: 37            moltype = AA  length = 39
FEATURE                  Location/Qualifiers
REGION                   1..39
                         note = Synthetic Construct
SITE                     1
                         note = MISC_FEATURE - Xaa at position 1 is D-Tyr
MOD_RES                  1
                         note = The N-terminus of Xaa at position 1 is acetylated
SITE                     6
                         note = MISC_FEATURE - Xaa at position 6 is
                          alpha-methyl-Phe(2F)
MOD_RES                  17
                         note = Lys at position 17 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
                          )18-CO 2H
SITE                     20
                         note = MISC_FEATURE - Xaa at position 20 is Aib
MOD_RES                  39
                         note = Ser at position 39 is amidated
source                   1..39
                         mol_type = protein
                         organism = synthetic construct
SEQUENCE: 37
XAEGTXISDY SIALDKKHQX EFVNYLLEGG PSSGAPPPS                              39

SEQ ID NO: 38            moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     6
                         note = MISC_FEATURE - Xaa at position 6 is
                          alpha-methyl-Phe(2F)
MOD_RES                  17
                         note = Lys at position 17 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
                          )18-CO 2H
SITE                     20
                         note = MISC_FEATURE - Xaa at position 20 is Aib
MOD_RES                  39
                         note = Ser at position 39 is amidated
source                   1..39
                         mol_type = protein
                         organism = synthetic construct
SEQUENCE: 38
YXEGTXISDY SIALDKKHQX EFVNYLLATG PSSGAPPPS                              39

SEQ ID NO: 39            moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     6
                         note = MISC_FEATURE - Xaa at position 6 is alpha-methyl-Leu
```

-continued

```
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 39
YXEGTXISDY SIALDKKHQX EFVNYLLATG PSSGAPPPS                         39

SEQ ID NO: 40           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is
                         alpha-methyl-Phe(2F)
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 40
YXEGTXISDY SIALDKKHQX DFVEYLLETG PSSGAPPPS                         39

SEQ ID NO: 41           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is
                         alpha-methyl-Phe(2F)
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 41
YXEGTXISDY SIALDKKHQX DFVEYLLEGG PSSGAPPPS                         39

SEQ ID NO: 42           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is
                         alpha-methyl-Phe(2F)
MOD_RES                 17
                        note = Lys at position 17 is chemically modified by
                         conjugation of the epsilon-amino group of the Lys side
                         chain with
```

-continued

```
                         (2-[2-(2-amino-ethoxy)-ethoxy]-acetyl)2-(gamma-Glu)-CO-(CH2
                         )18-CO 2H
SITE                     20
                         note = MISC_FEATURE - Xaa at position 20 is Aib
SITE                     25
                         note = MISC_FEATURE - Xaa at position 25 is 4-Pal
MOD_RES                  39
                         note = Ser at position 39 is amidated
source                   1..39
                         mol_type = protein
                         organism = synthetic construct
SEQUENCE: 42
YXEGTXISDY SIALDKKHQX DFVEXLLETG PSSGAPPPS                        39

SEQ ID NO: 43            moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     6
                         note = MISC_FEATURE - Xaa at position 6 is
                          alpha-methyl-Phe(2F)
MOD_RES                  17
                         note = Lys at position 17 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
                          )18-CO 2H
SITE                     20
                         note = MISC_FEATURE - Xaa at position 20 is Aib
SITE                     25
                         note = MISC_FEATURE - Xaa at position 25 is 4-Pal
MOD_RES                  39
                         note = Ser at position 39 is amidated
source                   1..39
                         mol_type = protein
                         organism = synthetic construct
SEQUENCE: 43
YXEGTXISDY SIALDKKHQX DFVEXLLEGG PSSGAPPPS                        39

SEQ ID NO: 44            moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     6
                         note = MISC_FEATURE - Xaa at position 6 is
                          alpha-methyl-Phe(2F)
MOD_RES                  17
                         note = Lys at position 17 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
                          )18-CO 2H
SITE                     20
                         note = MISC_FEATURE - Xaa at position 20 is Aib
MOD_RES                  39
                         note = Ser at position 39 is amidated
source                   1..39
                         mol_type = protein
                         organism = synthetic construct
SEQUENCE: 44
YXEGTXISDY SIALDKKHQX DFVEWLLETG PSSGAPPPS                        39

SEQ ID NO: 45            moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     6
                         note = MISC_FEATURE - Xaa at position 6 is alpha-methyl-Phe
MOD_RES                  17
                         note = Lys at position 17 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
```

```
                        )18-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 45
YXEGTXISDY SIALDKKHQX DFVEXLLETG PSSGAPPPS                       39

SEQ ID NO: 46           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is alpha-methyl-Phe
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 46
YXEGTXISDY SIALDKKHQX DFVEXLLEQG PSSGAPPPS                       39

SEQ ID NO: 47           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is alpha-methyl-Phe
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 47
YXEGTXISDY SIALDKKHQX DFVEXLLEAG PSSGAPPPS                       39

SEQ ID NO: 48           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is alpha-methyl-Phe
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
```

```
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 48
YXEGTXISDY SIALDKKHQX DFVEXLLEGG PSSGAPPPS                          39

SEQ ID NO: 49           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 49
YXEGTFISDY SIXLDKKHQX DFVEXLLETG PSSGAPPPS                          39

SEQ ID NO: 50           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 50
YXEGTFISDY SIXLDKKHQX DFVEXLLEQG PSSGAPPPS                          39

SEQ ID NO: 51           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
```

-continued

```
                         note = MISC_FEATURE - Xaa at position 20 is Aib
SITE                     25
                         note = MISC_FEATURE - Xaa at position 25 is 4-Pal
MOD_RES                  39
                         note = Ser at position 39 is amidated
source                   1..39
                         mol_type = protein
                         organism = synthetic construct
SEQUENCE: 51
YXEGTFISDY SIXLDKKHQX DFVEXLLEGG PSSGAPPPS                          39

SEQ ID NO: 52            moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     13
                         note = MISC_FEATURE - Xaa at position 13 is alpha-methyl-Leu
MOD_RES                  17
                         note = Lys at position 17 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
                          )18-CO 2H
SITE                     20
                         note = MISC_FEATURE - Xaa at position 20 is Aib
SITE                     25
                         note = MISC_FEATURE - Xaa at position 25 is 4-Pal
MOD_RES                  39
                         note = Ser at position 39 is amidated
source                   1..39
                         mol_type = protein
                         organism = synthetic construct
SEQUENCE: 52
YXEGTFISDY SIXLDKKHQX DFVEXLLAGG PSSGAPPPS                          39

SEQ ID NO: 53            moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     13
                         note = MISC_FEATURE - Xaa at position 13 is alpha-methyl-Leu
MOD_RES                  17
                         note = Lys at position 17 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
                          )16-CO 2H
SITE                     20
                         note = MISC_FEATURE - Xaa at position 20 is Aib
SITE                     25
                         note = MISC_FEATURE - Xaa at position 25 is 4-Pal
MOD_RES                  39
                         note = Ser at position 39 is amidated
source                   1..39
                         mol_type = protein
                         organism = synthetic construct
SEQUENCE: 53
YXEGTFISDY SIXLDKKHQX DFVEXLLAGG PSSGAPPPS                          39

SEQ ID NO: 54            moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     6
                         note = MISC_FEATURE - Xaa at position 6 is alpha-methyl-Phe
SITE                     13
                         note = MISC_FEATURE - Xaa at position 13 is alpha-methyl-Leu
MOD_RES                  17
                         note = Lys at position 17 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
                          )18-CO 2H
```

-continued

```
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 54
YXEGTXISDY SIXLDKKHQX DFVEXLLAGG PSSGAPPPS                          39

SEQ ID NO: 55           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is
                         alpha-methyl-Phe(2F)
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 55
YXEGTXISDY SIXLDKKHQX DFVEXLLAGG PSSGAPPPS                          39

SEQ ID NO: 56           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 56
YXEGTFISDY SIXLDKKHQX EFVEXLLAGG PSSGAPPPS                          39

SEQ ID NO: 57           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
```

```
                         (2-[2-(2-amino-ethoxy)-ethoxy]-acetyl)2-(gamma-Glu)-CO-(CH2
                         )18-CO 2H
SITE                     20
                         note = MISC_FEATURE - Xaa at position 20 is Aib
MOD_RES                  39
                         note = Ser at position 39 is amidated
source                   1..39
                         mol_type = protein
                         organism = synthetic construct
SEQUENCE: 57
YXEGTFISDY SIXLDKKHQX DFVEYLLAGG PSSGAPPPS                         39

SEQ ID NO: 58            moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     13
                         note = MISC_FEATURE - Xaa at position 13 is alpha-methyl-Leu
MOD_RES                  17
                         note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                     20
                         note = MISC_FEATURE - Xaa at position 20 is Aib
MOD_RES                  39
                         note = Ser at position 39 is amidated
source                   1..39
                         mol_type = protein
                         organism = synthetic construct
SEQUENCE: 58
YXEGTFISDY SIXLDKKHQX DFVEWLLAGG PSSGAPPPS                         39

SEQ ID NO: 59            moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     6
                         note = MISC_FEATURE - Xaa at position 6 is Iva
SITE                     13
                         note = MISC_FEATURE - Xaa at position 13 is alpha-methyl-Leu
MOD_RES                  17
                         note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                     20
                         note = MISC_FEATURE - Xaa at position 20 is Aib
SITE                     25
                         note = MISC_FEATURE - Xaa at position 25 is 4-Pal
MOD_RES                  39
                         note = Ser at position 39 is amidated
source                   1..39
                         mol_type = protein
                         organism = synthetic construct
SEQUENCE: 59
YXEGTXISDY SIXLDKKHQX DFVEXLLAGG PSSGAPPPS                         39

SEQ ID NO: 60            moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     13
                         note = MISC_FEATURE - Xaa at position 13 is alpha-methyl-Leu
MOD_RES                  17
                         note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                     20
```

-continued

```
                        note = MISC_FEATURE - Xaa at position 20 is Aib
SITE                    22
                        note = MISC_FEATURE - Xaa at position 22 is alpha-methyl-Phe
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 60
YXEGTFISDY SIXLDKKHQX DXVEXLLAGG PSSGAPPPS                          39

SEQ ID NO: 61           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 61
YXEGTFISDY SIXLDKKHQX EFVEXLLAQG PSSGAPPPS                          39

SEQ ID NO: 62           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 62
YXEGTFISDY SIXLDKKHQX EFVEXLLATG PSSGAPPPS                          39

SEQ ID NO: 63           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
```

```
SITE                  20
                      note = MISC_FEATURE - Xaa at position 20 is Aib
SITE                  25
                      note = MISC_FEATURE - Xaa at position 25 is 4-Pal
MOD_RES               39
                      note = Ser at position 39 is amidated
source                1..39
                      mol_type = protein
                      organism = synthetic construct
SEQUENCE: 63
YXEGTFISDY SIXLDKKHQX EFVEXLLAAG PSSGAPPPS                        39

SEQ ID NO: 64         moltype = AA  length = 39
FEATURE               Location/Qualifiers
REGION                1..39
                      note = Synthetic Construct
SITE                  2
                      note = MISC_FEATURE - Xaa at position 2 is Aib
SITE                  6
                      note = MISC_FEATURE - Xaa at position 6 is alpha-methyl-Phe
SITE                  13
                      note = MISC_FEATURE - Xaa at position 13 is alpha-methyl-Leu
MOD_RES               17
                      note = Lys at position 17 is chemically modified by
                       conjugation of the epsilon-amino group of the Lys side
                       chain with
                       (2-[2-(2-amino-ethoxy)-ethoxy]-acetyl)2-(gamma-Glu)-CO-(CH2
                       )18-CO 2H
SITE                  20
                      note = MISC_FEATURE - Xaa at position 20 is Aib
SITE                  25
                      note = MISC_FEATURE - Xaa at position 25 is 4-Pal
MOD_RES               39
                      note = Ser at position 39 is amidated
source                1..39
                      mol_type = protein
                      organism = synthetic construct
SEQUENCE: 64
YXEGTXISDY SIXLDKKHQX EFVEXLLAQG PSSGAPPPS                        39

SEQ ID NO: 65         moltype = AA  length = 39
FEATURE               Location/Qualifiers
REGION                1..39
                      note = Synthetic Construct
SITE                  2
                      note = MISC_FEATURE - Xaa at position 2 is Aib
SITE                  6
                      note = MISC_FEATURE - Xaa at position 6 is alpha-methyl-Phe
SITE                  13
                      note = MISC_FEATURE - Xaa at position 13 is alpha-methyl-Leu
MOD_RES               17
                      note = Lys at position 17 is chemically modified by
                       conjugation of the epsilon-amino group of the Lys side
                       chain with
                       (2-[2-(2-amino-ethoxy)-ethoxy]-acetyl)2-(gamma-Glu)-CO-(CH2
                       )18-CO 2H
SITE                  20
                      note = MISC_FEATURE - Xaa at position 20 is Aib
SITE                  25
                      note = MISC_FEATURE - Xaa at position 25 is 4-Pal
MOD_RES               39
                      note = Ser at position 39 is amidated
source                1..39
                      mol_type = protein
                      organism = synthetic construct
SEQUENCE: 65
YXEGTXISDY SIXLDKKHQX EFVEXLLATG PSSGAPPPS                        39

SEQ ID NO: 66         moltype = AA  length = 39
FEATURE               Location/Qualifiers
REGION                1..39
                      note = Synthetic Construct
SITE                  2
                      note = MISC_FEATURE - Xaa at position 2 is Aib
SITE                  6
                      note = MISC_FEATURE - Xaa at position 6 is alpha-methyl-Phe
SITE                  13
                      note = MISC_FEATURE - Xaa at position 13 is alpha-methyl-Leu
MOD_RES               17
```

```
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 66
YXEGTXISDY SIXLDKKHQX EFVEXLLAAG PSSGAPPPS                           39

SEQ ID NO: 67           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 67
YXEGTFISDY SIXLDKKHQX EFVEYLLEQG PSSGAPPPS                           39

SEQ ID NO: 68           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 68
YXEGTFISDY SIXLDKKHQX EFVEYLLETG PSSGAPPPS                           39

SEQ ID NO: 69           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
```

-continued

```
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 69
YXEGTFISDY SIXLDKKHQX EFVEYLLEAG PSSGAPPPS                              39

SEQ ID NO: 70           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 70
YXEGTFISDY SIXLDKKHQX DFVEYLLETG PSSGAPPPS                              39

SEQ ID NO: 71           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 71
YXEGTFISDY SIXLDKKHQX DFVEYLLEQG PSSGAPPPS                              39

SEQ ID NO: 72           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
```

-continued

```
SEQUENCE: 72
YXEGTFISDY SIXLDKKHQX DFVEYLLEAG PSSGAPPPS                       39

SEQ ID NO: 73           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 73
YXEGTFISDY SIXLDKKHQX DFVEYLLEGG PSSGAPPPS                       39

SEQ ID NO: 74           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 74
YXEGTFISDY SIXLDKKHQX DFVEXLLATG PSSGAPPPS                       39

SEQ ID NO: 75           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 75
YXEGTFISDY SIXLDKKHQX DFVEWLLETG PSSGAPPPS                       39

SEQ ID NO: 76           moltype = AA  length = 39
FEATURE                 Location/Qualifiers
```

-continued

```
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 76
YXEGTLISDY SIXLDKKHQX EFVEYLLETG PSSGAPPPS                        39

SEQ ID NO: 77           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
MOD_RES                 39
                        note = Ser at position 39 is amidated
source                  1..39
                        mol_type = protein
                        organism = synthetic construct
SEQUENCE: 77
YXEGTLISDY SIXLDKKHQX EFVEYLLEGG PSSGAPPPS                        39

SEQ ID NO: 78           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is Iva
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 78
YXEGTXISDY SIXLDKKHQX DFVEXLLEGG PSSGAPPPS                        39

SEQ ID NO: 79           moltype = AA  length = 39
FEATURE                 Location/Qualifiers
REGION                  1..39
                        note = Synthetic Construct
SITE                    2
```

-continued

```
                         note = MISC_FEATURE - Xaa at position 2 is Aib
SITE                     6
                         note = MISC_FEATURE - Xaa at position 6 is Iva
SITE                     13
                         note = MISC_FEATURE - Xaa at position 13 is alpha-methyl-Leu
MOD_RES                  17
                         note = Lys at position 17 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
                          )18-CO 2H
SITE                     20
                         note = MISC_FEATURE - Xaa at position 20 is Aib
SITE                     25
                         note = MISC_FEATURE - Xaa at position 25 is 4-Pal
MOD_RES                  39
                         note = Ser at position 39 is amidated
source                   1..39
                         mol_type = protein
                         organism = synthetic construct
SEQUENCE: 79
YXEGTXISDY SIXLDKKHQX DFVEXLLETG PSSGAPPPS                        39

SEQ ID NO: 80            moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     6
                         note = MISC_FEATURE - Xaa at position 6 is Iva
SITE                     13
                         note = MISC_FEATURE - Xaa at position 13 is alpha-methyl-Leu
SITE                     16
                         note = MISC_FEATURE - Xaa at position 16 is Orn
MOD_RES                  17
                         note = Lys at position 17 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
                          )18-CO 2H
SITE                     20
                         note = MISC_FEATURE - Xaa at position 20 is Aib
SITE                     25
                         note = MISC_FEATURE - Xaa at position 25 is 4-Pal
MOD_RES                  39
                         note = Ser at position 39 is amidated
source                   1..39
                         mol_type = protein
                         organism = synthetic construct
SEQUENCE: 80
YXEGTXISDY SIXLDXKHQX DFVEXLLEGG PSSGAPPPS                        39

SEQ ID NO: 81            moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     6
                         note = MISC_FEATURE - Xaa at position 6 is Iva
SITE                     13
                         note = MISC_FEATURE - Xaa at position 13 is alpha-methyl-Leu
SITE                     16
                         note = MISC_FEATURE - Xaa at position 16 is Orn
MOD_RES                  17
                         note = Lys at position 17 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
                          )18-CO 2H
SITE                     20
                         note = MISC_FEATURE - Xaa at position 20 is Aib
SITE                     25
                         note = MISC_FEATURE - Xaa at position 25 is 4-Pal
MOD_RES                  39
                         note = Ser at position 39 is amidated
source                   1..39
                         mol_type = protein
```

-continued

```
                         organism = synthetic construct
SEQUENCE: 81
YXEGTXISDY SIXLDXKHQX DFVEXLLETG PSSGAPPPS                      39

SEQ ID NO: 82            moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     13
                         note = MISC_FEATURE - Xaa at position 13 is alpha-methyl-Leu
MOD_RES                  17
                         note = Lys at position 17 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
                          )18-CO 2H
SITE                     20
                         note = MISC_FEATURE - Xaa at position 20 is Aib
SITE                     25
                         note = MISC_FEATURE - Xaa at position 25 is 4-Pal
MOD_RES                  39
                         note = Ser at position 39 is amidated
source                   1..39
                         mol_type = protein
                         organism = synthetic construct
SEQUENCE: 82
YXEGTFISDY SIXLDKKHQX DFVEXLLAAG PSSGAPPPS                      39

SEQ ID NO: 83            moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     13
                         note = MISC_FEATURE - Xaa at position 13 is alpha-methyl-Leu
MOD_RES                  17
                         note = Lys at position 17 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
                          )18-CO 2H
SITE                     20
                         note = MISC_FEATURE - Xaa at position 20 is Aib
SITE                     25
                         note = MISC_FEATURE - Xaa at position 25 is 4-Pal
MOD_RES                  39
                         note = Ser at position 39 is amidated
source                   1..39
                         mol_type = protein
                         organism = synthetic construct
SEQUENCE: 83
YXEGTFISDY SIXLDKKHQX DFVEXLLAQG PSSGAPPPS                      39

SEQ ID NO: 84            moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     13
                         note = MISC_FEATURE - Xaa at position 13 is alpha-methyl-Leu
SITE                     16
                         note = MISC_FEATURE - Xaa at position 16 is Orn
MOD_RES                  17
                         note = Lys at position 17 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
                          )18-CO 2H
SITE                     20
                         note = MISC_FEATURE - Xaa at position 20 is Aib
SITE                     25
                         note = MISC_FEATURE - Xaa at position 25 is 4-Pal
MOD_RES                  39
                         note = Ser at position 39 is amidated
source                   1..39
```

-continued

```
                       mol_type = protein
                       organism = synthetic construct
SEQUENCE: 84
YXEGTFISDY SIXLDXKHQX DFVEXLLETG PSSGAPPPS                         39

SEQ ID NO: 85          moltype = AA  length = 39
FEATURE                Location/Qualifiers
REGION                 1..39
                       note = Synthetic Construct
SITE                   2
                       note = MISC_FEATURE - Xaa at position 2 is Aib
SITE                   13
                       note = MISC_FEATURE - Xaa at position 13 is alpha-methyl-Leu
SITE                   16
                       note = MISC_FEATURE - Xaa at position 16 is Orn
MOD_RES                17
                       note = Lys at position 17 is chemically modified by
                        conjugation of the epsilon-amino group of the Lys side
                        chain with
                        (2-[2-(2-amino-ethoxy)-ethoxy]-acetyl)2-(gamma-Glu)-CO-(CH2
                        )18-CO 2H
SITE                   20
                       note = MISC_FEATURE - Xaa at position 20 is Aib
SITE                   25
                       note = MISC_FEATURE - Xaa at position 25 is 4-Pal
MOD_RES                39
                       note = Ser at position 39 is amidated
source                 1..39
                       mol_type = protein
                       organism = synthetic construct
SEQUENCE: 85
YXEGTFISDY SIXLDXKHQX DFVEXLLEQG PSSGAPPPS                         39

SEQ ID NO: 86          moltype = AA  length = 39
FEATURE                Location/Qualifiers
REGION                 1..39
                       note = Synthetic Construct
SITE                   2
                       note = MISC_FEATURE - Xaa at position 2 is Aib
SITE                   13
                       note = MISC_FEATURE - Xaa at position 13 is alpha-methyl-Leu
SITE                   16
                       note = MISC_FEATURE - Xaa at position 16 is Orn
MOD_RES                17
                       note = Lys at position 17 is chemically modified by
                        conjugation of the epsilon-amino group of the Lys side
                        chain with
                        (2-[2-(2-amino-ethoxy)-ethoxy]-acetyl)2-(gamma-Glu)-CO-(CH2
                        )18-CO 2H
SITE                   20
                       note = MISC_FEATURE - Xaa at position 20 is Aib
SITE                   25
                       note = MISC_FEATURE - Xaa at position 25 is 4-Pal
MOD_RES                39
                       note = Ser at position 39 is amidated
source                 1..39
                       mol_type = protein
                       organism = synthetic construct
SEQUENCE: 86
YXEGTFISDY SIXLDXKHQX DFVEXLLEGG PSSGAPPPS                         39

SEQ ID NO: 87          moltype = AA  length = 39
FEATURE                Location/Qualifiers
REGION                 1..39
                       note = Synthetic Construct
SITE                   2
                       note = MISC_FEATURE - Xaa at position 2 is Aib
SITE                   13
                       note = MISC_FEATURE - Xaa at position 13 is alpha-methyl-Leu
MOD_RES                17
                       note = Lys at position 17 is chemically modified by
                        conjugation of the epsilon-amino group of the Lys side
                        chain with
                        (2-[2-(2-amino-ethoxy)-ethoxy]-acetyl)2-(gamma-Glu)-CO-(CH2
                        )18-CO 2H
SITE                   20
                       note = MISC_FEATURE - Xaa at position 20 is Aib
SITE                   25
                       note = MISC_FEATURE - Xaa at position 25 is 4-Pal
```

```
MOD_RES                39
                       note = Ser at position 39 is amidated
source                 1..39
                       mol_type = protein
                       organism = synthetic construct
SEQUENCE: 87
YXEGTFISDY SIXLDEKHQX DFVEXLLATG PSSGAPPPS                           39

SEQ ID NO: 88          moltype = AA  length = 39
FEATURE                Location/Qualifiers
REGION                 1..39
                       note = Synthetic Construct
SITE                   2
                       note = MISC_FEATURE - Xaa at position 2 is Aib
SITE                   13
                       note = MISC_FEATURE - Xaa at position 13 is alpha-methyl-Leu
MOD_RES                17
                       note = Lys at position 17 is chemically modified by
                        conjugation of the epsilon-amino group of the Lys side
                        chain with
                        (2-[2-(2-amino-ethoxy)-ethoxy]-acetyl)2-(gamma-Glu)-CO-(CH2
                        )18-CO 2H
SITE                   20
                       note = MISC_FEATURE - Xaa at position 20 is Aib
SITE                   25
                       note = MISC_FEATURE - Xaa at position 25 is 4-Pal
MOD_RES                39
                       note = Ser at position 39 is amidated
source                 1..39
                       mol_type = protein
                       organism = synthetic construct
SEQUENCE: 88
YXEGTFISDY SIXLDEKHQX DFVEXLLAQG PSSGAPPPS                           39

SEQ ID NO: 89          moltype = AA  length = 39
FEATURE                Location/Qualifiers
REGION                 1..39
                       note = Synthetic Construct
SITE                   2
                       note = MISC_FEATURE - Xaa at position 2 is Aib
SITE                   13
                       note = MISC_FEATURE - Xaa at position 13 is alpha-methyl-Leu
MOD_RES                17
                       note = Lys at position 17 is chemically modified by
                        conjugation of the epsilon-amino group of the Lys side
                        chain with
                        (2-[2-(2-amino-ethoxy)-ethoxy]-acetyl)2-(gamma-Glu)-CO-(CH2
                        )18-CO 2H
SITE                   20
                       note = MISC_FEATURE - Xaa at position 20 is Aib
SITE                   25
                       note = MISC_FEATURE - Xaa at position 25 is 4-Pal
MOD_RES                39
                       note = Ser at position 39 is amidated
source                 1..39
                       mol_type = protein
                       organism = synthetic construct
SEQUENCE: 89
YXEGTFISDY SIXLDEKHQX DFVEXLLAAG PSSGAPPPS                           39

SEQ ID NO: 90          moltype = AA  length = 39
FEATURE                Location/Qualifiers
REGION                 1..39
                       note = Synthetic Construct
SITE                   2
                       note = MISC_FEATURE - Xaa at position 2 is Aib
SITE                   13
                       note = MISC_FEATURE - Xaa at position 13 is alpha-methyl-Leu
MOD_RES                17
                       note = Lys at position 17 is chemically modified by
                        conjugation of the epsilon-amino group of the Lys side
                        chain with
                        (2-[2-(2-amino-ethoxy)-ethoxy]-acetyl)2-(gamma-Glu)-CO-(CH2
                        )18-CO 2H
SITE                   20
                       note = MISC_FEATURE - Xaa at position 20 is Aib
SITE                   25
                       note = MISC_FEATURE - Xaa at position 25 is 4-Pal
MOD_RES                39
```

```
                        note = Ser at position 39 is amidated
source                  1..39
                        mol_type = protein
                        organism = synthetic construct
SEQUENCE: 90
YXEGTFISDY SIXLDEKHQX DFVEXLLAGG PSSGAPPPS                          39

SEQ ID NO: 91           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
SITE                    16
                        note = MISC_FEATURE - Xaa at position 16 is Orn
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )16-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 91
YXEGTFISDY SIXLDXKHQX DFVEXLLEAG PSSGAPPPS                          39

SEQ ID NO: 92           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is Iva
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 92
YXEGTXISDY SIXLDKKHQX DFVEXLLEAG PSSGAPPPS                          39

SEQ ID NO: 93           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
```

-continued

```
SITE                    25
                        note = MISC_FEATURE - Xaa at position 25 is 4-Pal
MOD_RES                 39
                        note = Ser at position 39 is amidated
source                  1..39
                        mol_type = protein
                        organism = synthetic construct
SEQUENCE: 93
YXEGTLISDY SIXLDKKHQX DFVEXLLEAG PSSGAPPPS                        39

SEQ ID NO: 94           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
SITE                    25
                        note = MISC_FEATURE - Xaa at position 25 is alpha-methyl-Tyr
MOD_RES                 39
                        note = Ser at position 39 is amidated
source                  1..39
                        mol_type = protein
                        organism = synthetic construct
SEQUENCE: 94
YXEGTFISDY SIXLDKKHQX DFVEXLLEAG PSSGAPPPS                        39

SEQ ID NO: 95           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
MOD_RES                 17
                        note = Lys at position 17 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
SITE                    20
                        note = MISC_FEATURE - Xaa at position 20 is Aib
SITE                    25
                        note = MISC_FEATURE - Xaa at position 25 is alpha-methyl-Tyr
MOD_RES                 39
                        note = Ser at position 39 is amidated
source                  1..39
                        mol_type = protein
                        organism = synthetic construct
SEQUENCE: 95
YXEGTFISDY SIXLDKKHQX DFVEXLLEGG PSSGAPPPS                        39

SEQ ID NO: 96           moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
SITE                    20
                        note = MISC_FEATURE - Xaa at position 20 is Aib
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
```

-continued

```
                      note = Ser at position 39 is amidated
source                1..39
                      mol_type = protein
                      organism = synthetic construct
SEQUENCE: 96
YXEGTFISDY SIXLDKIHQX DFVEYKLEQG PSSGAPPPS                        39

SEQ ID NO: 97         moltype = AA  length = 39
FEATURE               Location/Qualifiers
REGION                1..39
                      note = Synthetic Construct
SITE                  2
                      note = MISC_FEATURE - Xaa at position 2 is D-Ala
SITE                  20
                      note = MISC_FEATURE - Xaa at position 20 is Aib
MOD_RES               26
                      note = Lys at position 26 is chemically modified by
                       conjugation of the epsilon-amino group of the Lys side
                       chain with
                       (2-[2-(2-amino-ethoxy)-ethoxy]-acetyl)2-(gamma-Glu)-CO-(CH2
                       )16-CO 2H
MOD_RES               39
                      note = Ser at position 39 is amidated
source                1..39
                      mol_type = protein
                      organism = synthetic construct
SEQUENCE: 97
YXEGTFISDY SILLDKIAQX DFVNWKLAQG PSSGAPPPS                        39

SEQ ID NO: 98         moltype = AA  length = 39
FEATURE               Location/Qualifiers
REGION                1..39
                      note = Synthetic Construct
SITE                  2
                      note = MISC_FEATURE - Xaa at position 2 is Aib
SITE                  6
                      note = MISC_FEATURE - Xaa at position 6 is
                       alpha-methyl-Phe(2F)
SITE                  20
                      note = MISC_FEATURE - Xaa at position 20 is Aib
MOD_RES               26
                      note = Lys at position 26 is chemically modified by
                       conjugation of the epsilon-amino group of the Lys side
                       chain with
                       (2-[2-(2-amino-ethoxy)-ethoxy]-acetyl)2-(gamma-Glu)-CO-(CH2
                       )16-CO 2H
MOD_RES               39
                      note = Ser at position 39 is amidated
source                1..39
                      mol_type = protein
                      organism = synthetic construct
SEQUENCE: 98
YXEGTXISDY SIALDKIHQX EFVNYKLAGG PSSGAPPPS                        39

SEQ ID NO: 99         moltype = AA  length = 39
FEATURE               Location/Qualifiers
REGION                1..39
                      note = Synthetic Construct
SITE                  2
                      note = MISC_FEATURE - Xaa at position 2 is Aib
SITE                  6
                      note = MISC_FEATURE - Xaa at position 6 is
                       alpha-methyl-Phe(2F)
SITE                  20
                      note = MISC_FEATURE - Xaa at position 20 is Aib
MOD_RES               26
                      note = Lys at position 26 is chemically modified by
                       conjugation of the epsilon-amino group of the Lys side
                       chain with
                       (2-[2-(2-amino-ethoxy)-ethoxy]-acetyl)2-(gamma-Glu)-CO-(CH2
                       )18-CO 2H
MOD_RES               39
                      note = Ser at position 39 is amidated
source                1..39
                      mol_type = protein
                      organism = synthetic construct
SEQUENCE: 99
YXEGTXISDY SIALDKIHQX EFVNYKLEGG PSSGAPPPS                        39
```

```
SEQ ID NO: 100          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    20
                        note = MISC_FEATURE - Xaa at position 20 is Aib
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 100
YXEGTFISDY SIALDKIHQX EFVNYKLAGG PSSGAPPPS                         39

SEQ ID NO: 101          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is alpha-methyl-Phe
SITE                    20
                        note = MISC_FEATURE - Xaa at position 20 is Aib
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 101
YXEGTXISDY SIALDKIHQX EFVNYKLAGG PSSGAPPPS                         39

SEQ ID NO: 102          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is
                         alpha-methyl-Phe(2F)
SITE                    20
                        note = MISC_FEATURE - Xaa at position 20 is Aib
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 102
YXEGTXISDY SIALDKIHQX EFVNYKLAGG PSSGAPPPS                         39

SEQ ID NO: 103          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is
```

```
                        alpha-methyl-Phe(2F)
SITE                    20
                        note = MISC_FEATURE - Xaa at position 20 is Aib
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 103
YXEGTXISDY SIALDKIHQX DFVEYKLEGG PSSGAPPPS                        39

SEQ ID NO: 104          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
SITE                    20
                        note = MISC_FEATURE - Xaa at position 20 is Aib
SITE                    25
                        note = MISC_FEATURE - Xaa at position 25 is 4-Pal
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 104
YXEGTFISDY SIXLDKIHQX EFVEXKLEGG PSSGAPPPS                        39

SEQ ID NO: 105          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
SITE                    16
                        note = MISC_FEATURE - Xaa at position 16 is Orn
SITE                    20
                        note = MISC_FEATURE - Xaa at position 20 is Aib
SITE                    24
                        note = MISC_FEATURE - Xaa at position 24 is D-Glu
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 105
YXEGTFISDY SIXLDXIHQX DFVXYKLEGG PSSGAPPPS                        39

SEQ ID NO: 106          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
```

-continued

```
SITE                    16
                        note = MISC_FEATURE - Xaa at position 16 is Orn
SITE                    20
                        note = MISC_FEATURE - Xaa at position 20 is Aib
SITE                    24
                        note = MISC_FEATURE - Xaa at position 24 is D-Glu
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 106
YXEGTFISDY SIXLDXIHQX EFVXYKLEGG PSSGAPPPS                        39

SEQ ID NO: 107          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
SITE                    16
                        note = MISC_FEATURE - Xaa at position 16 is Orn
SITE                    20
                        note = MISC_FEATURE - Xaa at position 20 is Aib
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )16-CO 2H
MOD_RES                 39
                        note = Ser at position 39 is amidated
source                  1..39
                        mol_type = protein
                        organism = synthetic construct
SEQUENCE: 107
YXEGTFISDY SIXLDXIHQX DFVEYKLEGG PSSGAPPPS                        39

SEQ ID NO: 108          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
SITE                    16
                        note = MISC_FEATURE - Xaa at position 16 is Orn
SITE                    20
                        note = MISC_FEATURE - Xaa at position 20 is Aib
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 108
YXEGTFISDY SIXLDXIHQX EFVEYKLEAG PSSGAPPPS                        39

SEQ ID NO: 109          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
```

-continued

```
                       note = MISC_FEATURE - Xaa at position 13 is alpha-methyl-Leu
SITE                   16
                       note = MISC_FEATURE - Xaa at position 16 is Orn
SITE                   20
                       note = MISC_FEATURE - Xaa at position 20 is Aib
MOD_RES                26
                       note = Lys at position 26 is chemically modified by
                        conjugation of the epsilon-amino group of the Lys side
                        chain with
                        (2-[2-(2-amino-ethoxy)-ethoxy]-acetyl)2-(gamma-Glu)-CO-(CH2
                        )18-CO 2H
MOD_RES                39
                       note = Ser at position 39 is amidated
source                 1..39
                       mol_type = protein
                       organism = synthetic construct
SEQUENCE: 109
YXEGTFISDY SIXLDXIHQX EFVEYKLETG PSSGAPPPS                         39

SEQ ID NO: 110         moltype = AA  length = 39
FEATURE                Location/Qualifiers
REGION                 1..39
                       note = Synthetic Construct
SITE                   2
                       note = MISC_FEATURE - Xaa at position 2 is Aib
SITE                   13
                       note = MISC_FEATURE - Xaa at position 13 is alpha-methyl-Leu
SITE                   16
                       note = MISC_FEATURE - Xaa at position 16 is Orn
SITE                   20
                       note = MISC_FEATURE - Xaa at position 20 is Aib
MOD_RES                26
                       note = Lys at position 26 is chemically modified by
                        conjugation of the epsilon-amino group of the Lys side
                        chain with
                        (2-[2-(2-amino-ethoxy)-ethoxy]-acetyl)2-(gamma-Glu)-CO-(CH2
                        )18-CO 2H
MOD_RES                39
                       note = Ser at position 39 is amidated
source                 1..39
                       mol_type = protein
                       organism = synthetic construct
SEQUENCE: 110
YXEGTFISDY SIXLDXIHQX EFVEYKLEQG PSSGAPPPS                         39

SEQ ID NO: 111         moltype = AA  length = 39
FEATURE                Location/Qualifiers
REGION                 1..39
                       note = Synthetic Construct
SITE                   2
                       note = MISC_FEATURE - Xaa at position 2 is Aib
SITE                   13
                       note = MISC_FEATURE - Xaa at position 13 is alpha-methyl-Leu
SITE                   16
                       note = MISC_FEATURE - Xaa at position 16 is Orn
SITE                   20
                       note = MISC_FEATURE - Xaa at position 20 is Aib
MOD_RES                26
                       note = Lys at position 26 is chemically modified by
                        conjugation of the epsilon-amino group of the Lys side
                        chain with
                        (2-[2-(2-amino-ethoxy)-ethoxy]-acetyl)2-(gamma-Glu)-CO-(CH2
                        )18-CO 2H
MOD_RES                39
                       note = Ser at position 39 is amidated
source                 1..39
                       mol_type = protein
                       organism = synthetic construct
SEQUENCE: 111
YXEGTFISDY SIXLDXIHQX EFVEYKLEGG PSSGAPPPS                         39

SEQ ID NO: 112         moltype = AA  length = 39
FEATURE                Location/Qualifiers
REGION                 1..39
                       note = Synthetic Construct
SITE                   2
                       note = MISC_FEATURE - Xaa at position 2 is Aib
SITE                   13
                       note = MISC_FEATURE - Xaa at position 13 is alpha-methyl-Leu
```

```
SITE                    16
                        note = MISC_FEATURE - Xaa at position 16 is Orn
SITE                    20
                        note = MISC_FEATURE - Xaa at position 20 is Aib
SITE                    25
                        note = MISC_FEATURE - Xaa at position 25 is 4-Pal
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 112
YXEGTFISDY SIXLDXIHQX DFVEXKLEGG PSSGAPPPS                       39

SEQ ID NO: 113          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
SITE                    20
                        note = MISC_FEATURE - Xaa at position 20 is Aib
SITE                    25
                        note = MISC_FEATURE - Xaa at position 25 is 4-Pal
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 113
YXEGTFISDY SIXLDKIHQX DFVEXKLEGG PSSGAPPPS                       39

SEQ ID NO: 114          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
SITE                    20
                        note = MISC_FEATURE - Xaa at position 20 is Aib
SITE                    25
                        note = MISC_FEATURE - Xaa at position 25 is 4-Pal
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )16-CO 2H
MOD_RES                 39
                        note = Ser at position 39 is amidated
source                  1..39
                        mol_type = protein
                        organism = synthetic construct
SEQUENCE: 114
YXEGTFISDY SIXLDKIHQX DFVEXKLEGG PSSGAPPPS                       39

SEQ ID NO: 115          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
```

```
                        note = MISC_FEATURE - Xaa at position 13 is alpha-methyl-Leu
SITE                    16
                        note = MISC_FEATURE - Xaa at position 16 is Orn
SITE                    20
                        note = MISC_FEATURE - Xaa at position 20 is Aib
SITE                    25
                        note = MISC_FEATURE - Xaa at position 25 is 4-Pal
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )16-CO 2H
MOD_RES                 39
                        note = Ser at position 39 is amidated
source                  1..39
                        mol_type = protein
                        organism = synthetic construct
SEQUENCE: 115
YXEGTFISDY SIXLDXIHQX DFVEXKLEGG PSSGAPPPS                            39

SEQ ID NO: 116          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is
                         alpha-methyl-Phe(2F)
SITE                    20
                        note = MISC_FEATURE - Xaa at position 20 is Aib
SITE                    25
                        note = MISC_FEATURE - Xaa at position 25 is 4-Pal
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 116
YXEGTXISDY SIALDKIHQX DFVEXKLEGG PSSGAPPPS                            39

SEQ ID NO: 117          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is
                         alpha-methyl-Phe(2F)
SITE                    20
                        note = MISC_FEATURE - Xaa at position 20 is Aib
SITE                    25
                        note = MISC_FEATURE - Xaa at position 25 is 4-Pal
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 117
YXEGTXISDY SIALDKIHQX DFVEXKLEAG PSSGAPPPS                            39

SEQ ID NO: 118          moltype = AA  length = 39
FEATURE                 Location/Qualifiers
REGION                  1..39
                        note = Synthetic Construct
```

-continued

```
SITE                    2
                        note = MISC_FEATURE - Xaa at position 2 is Aib
SITE                    6
                        note = MISC_FEATURE - Xaa at position 6 is
                         alpha-methyl-Phe(2F)
SITE                    20
                        note = MISC_FEATURE - Xaa at position 20 is Aib
SITE                    25
                        note = MISC_FEATURE - Xaa at position 25 IS 4-Pal
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 118
YXEGTXISDY SIALDKIHQX DFVEXKLEQG PSSGAPPPS                          39

SEQ ID NO: 119          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
SITE                    20
                        note = MISC_FEATURE - Xaa at position 20 is Aib
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 119
YXEGTFISDY SIXLDKIRQX DFVEYKLEGG PSSGAPPPS                          39

SEQ ID NO: 120          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
SITE                    16
                        note = MISC_FEATURE - Xaa at position 16 is Orn
SITE                    20
                        note = MISC_FEATURE - Xaa at position 20 is Aib
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 120
YXEGTFISDY SIXLDXIRQX DFVEYKLEGG PSSGAPPPS                          39

SEQ ID NO: 121          moltype = AA  length = 39
FEATURE                 Location/Qualifiers
REGION                  1..39
                        note = Synthetic Construct
SITE                    2
                        note = MISC_FEATURE - Xaa at position 2 is Aib
```

```
SITE                    13
                        note = MISC_FEATURE - Xaa at position 13 is alpha-methyl-Leu
SITE                    20
                        note = MISC_FEATURE - Xaa at position 20 is Aib
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 121
YXEGTFISDY SIXLDKIHQX DFVEYKLEAG PSSGAPPPS                         39

SEQ ID NO: 122          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    13
                        note = MISC_FEATURE - Xaa at position 13 is alpha-methyl-Leu
SITE                    20
                        note = MISC_FEATURE - Xaa at position 20 is Aib
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 122
YXEGTFISDY SIXLDKIRQX DFVEYKLEAG PSSGAPPPS                         39

SEQ ID NO: 123          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is
                         alpha-methyl-F(2F)
SITE                    20
                        note = MISC_FEATURE - Xaa at position 29 is Aib
SITE                    25
                        note = MISC_FEATURE - Xaa at position 25 is 4-Pal
MOD_RES                 26
                        note = Lys at position 26 is chemically modified by
                         conjugation of the epsilon-amino group of the Lys side
                         chain with
                         (2-[2-(2-amino-ethoxy)-ethoxy]-acetyl)2-(gamma-Glu)-CO-(CH2
                         )18-CO 2H
MOD_RES                 39
                        note = Ser at position 39 is amidated
source                  1..39
                        mol_type = protein
                        organism = synthetic construct
SEQUENCE: 123
YXEGTXISDY SILLDKIHQX DFVEXKLEGG PSSGAPPPS                         39

SEQ ID NO: 124          moltype = AA  length = 39
FEATURE                 Location/Qualifiers
REGION                  1..39
                        note = Synthetic Construct
SITE                    2
                        note = MISC_FEATURE - Xaa at position 2 is Aib
SITE                    6
                        note = MISC_FEATURE - Xaa at position 6 is
                         alpha-methyl-Phe(2F)
SITE                    20
```

-continued

```
                         note = MISC_FEATURE - Xaa at position 20 is Aib
SITE                     25
                         note = MISC_FEATURE - Xaa at position 25 is 4-Pal
MOD_RES                  26
                         note = Lys at position 26 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
                          )18-CO 2H
MOD_RES                  39
                         note = Ser at position 39 is amidated
source                   1..39
                         mol_type = protein
                         organism = synthetic construct
SEQUENCE: 124
YXEGTXISDY SILLDKIHQX DFVEXKLEAG PSSGAPPPS                         39

SEQ ID NO: 125           moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     6
                         note = MISC_FEATURE - Xaa at position 6 is
                          alpha-methyl-Phe(2F)
SITE                     20
                         note = MISC_FEATURE - Xaa at position 20 is Aib
SITE                     25
                         note = MISC_FEATURE - Xaa at position 25 is 4-Pal
MOD_RES                  26
                         note = Lys at position 26 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
                          )18-CO 2H
MOD_RES                  39
                         note = Ser at position 39 is amidated
source                   1..39
                         mol_type = protein
                         organism = synthetic construct
SEQUENCE: 125
YXEGTXISDY SILLDKIHQX DFVEXKLEQG PSSGAPPPS                         39

SEQ ID NO: 126           moltype = AA  length = 39
FEATURE                  Location/Qualifiers
REGION                   1..39
                         note = Synthetic Construct
SITE                     2
                         note = MISC_FEATURE - Xaa at position 2 is Aib
SITE                     13
                         note = MISC_FEATURE - Xaa at position 13 is alpha-methyl-Leu
SITE                     16
                         note = MISC_FEATURE - Xaa at position 16 is Orn
SITE                     20
                         note = MISC_FEATURE - Xaa at position 20 is Aib
SITE                     25
                         note = MISC_FEATURE - Xaa at position 25 is 4-Pal
MOD_RES                  26
                         note = Lys at position 26 is chemically modified by
                          conjugation of the epsilon-amino group of the Lys side
                          chain with
                          (2-[2-(2-amino-ethoxy)-ethoxy]-acetyl)2-(gamma-Glu)-CO-(CH2
                          )18-CO 2H
MOD_RES                  39
                         note = Ser at position 39 is amidated
source                   1..39
                         mol_type = protein
                         organism = synthetic construct
SEQUENCE: 126
YXEGTFISDY SIXLDXIHQX EFVEXKLEAG PSSGAPPPS                         39
```

GIPR-AGONIST COMPOUNDS

CROSS REFERENCE TO RELATED APPLICATIONS

This application claims priority to U.S. Non-Provisional application Ser. No. 17/573,317 filed Jan. 11, 2022, which is a continuation of U.S. Non-Provisional application Ser. No. 16/941,990 filed Jul. 29, 2020, which claims priority to U.S. Provisional Ser. No. 62/881,685 filed Aug. 1, 2019, the entire contents of which are herein incorporated by reference.

REFERENCE TO SEQUENCE LISTING SUBMITTED ELECTRONICALLY

The disclosure is being filed along with a Sequence Listing in ST.26 XML format. The Sequence Listing is provided as a file titled "X21836B.xml" created 19 Dec. 2023 and is 454.924 bytes in size. The Sequence Listing information in the ST.26 XML format is incorporated herein by reference in its entirety.

The present invention relates to compounds having activity at the human glucose-dependent insulinotropic polypeptide (GIP) receptor. The present invention also relates to compounds having an extended duration of action at the GIP receptor. Compounds may be useful in the treatment of type 2 diabetes mellitus ("T2DM"). Also, the compounds may be useful in the treatment of obesity.

Over the past several decades, the prevalence of diabetes has continued to rise. T2DM is the most common form of diabetes, accounting for approximately 90% of all diabetes. T2DM is characterized by high blood glucose levels associated mainly with insulin resistance. The current standard of care for T2DM includes diet and exercise, treatment with oral medications, and injectable glucose-lowering drugs, including incretin-based therapies such as GLP-1 receptor agonists. A variety of GLP-1 receptor agonists are currently available for treatment of T2DM, although currently marketed GLP-1 receptor agonists are generally dose-limited by gastrointestinal side effects such as nausea and vomiting.

Subcutaneous injection is the typical route of administration for the available GLP-1 receptor agonists. When treatment with oral medications and incretin-based therapies are insufficient, insulin treatment is considered. Despite the advances in treatment available today, many patients with T2DM are unable to reach their glycemic control goals. Uncontrolled diabetes leads to several conditions associated with increased morbidity and mortality of patients.

There is a need for a treatment to enable more patients with T2DM to reach their glycemic treatment goals.

Obesity is a complex medical disorder resulting in excessive accumulation of adipose tissue mass. Today obesity is a global public health concern that is associated with undesired health outcomes and morbidities. Desired treatments for patients with obesity should reduce excess body weight, improve obesity-related co-morbidities, and maintain long-term weight reduction. Available treatments for obesity are particularly unsatisfactory for patients with severe obesity. There is a need for alternative treatment options to induce therapeutic weight loss in patients in need of such treatment.

WO2016/111971 describes peptides stated to have GLP-1R and GIPR agonist activities. WO2013/164483 also discloses compounds stated to have GLP-1R and GIPR activities.

WO2018/181864 discloses compounds stated to have GIPR agonist activity.

There is a need for T2DM treatments capable of providing effective glucose control for a larger portion of the patients in need of such treatment. There is a further need for T2DM treatments capable of providing effective glucose control and with a favorable side effect profile. There is a need for alternate treatment options to provide therapeutic weight loss in a patient in need of such treatment, such as a patient with severe obesity. There is a desire for diabetes treatment options that may be combined with insulin therapy and/or incretin therapy to provide the patient with superior glycemic outcomes and/or more desirable side effect profiles.

Compounds with extended duration of action at the GIP receptor are desirable to allow for less frequent dosing of the compound.

Accordingly, embodiment 1 is a compound of Formula I $Z_1X_1X_2EGTX_6ISDYSIX_{13}LDX_{16}X_{17}X_{18}QX_{20}X_{21}X_{22}VX_{24}X_{25}X_{26}L\ X_{28}X_{29}GPSSGAPPPSZ_2$ (SEQ ID NO:4) wherein:

$Z_1$ is a modification of the N-terminal amino group wherein the modification is selected from the group consisting of acetyl and absent;

$X_1$ is selected from the group consisting of Y and D-Tyr;

$X_2$ is selected from the group consisting of Aib, A, and D-Ala;

$X_6$ is selected from the group consisting of F, αMeF, Iva, L, αMeL, and αMeF(2F);

$X_{13}$ is selected from the group consisting of αMeL, A, L, and Aib;

$X_{16}$ is selected from the group consisting of K, E, and Orn;

$X_{17}$ is selected from the group consisting of I and K(2-[2-(2-amino-ethoxy)-ethoxy]-acetyl)$_2$-(γ-Glu)-CO—$(CH_2)_q$—$CO_2H$;

$X_{18}$ is selected from the group consisting of H, A, and R;

$X_{20}$ is selected from the group consisting of Aib and Q;

$X_{21}$ is selected from the group consisting of D and E;

$X_{22}$ is selected from the group consisting of F and αMeF;

$X_{24}$ is selected from the group consisting of E, N, Q, and D-Glu;

$X_{25}$ is selected from the group consisting of Y, 4-Pal, W, and αMeY;

$X_{26}$ is selected from the group consisting of L and K(2-[2-(2-amino-ethoxy)-ethoxy]-acetyl)$_2$-(γ-Glu)-CO—$(CH_2)_q$—$CO_2H$;

$X_{28}$ is selected from the group consisting of E and A;

$X_{29}$ is selected from the group consisting of G, A, Q, and T; q is selected from the group consisting of 16 and 18; and $Z_2$ is absent or a modification of the C-terminal group, wherein the modification is amidation;

wherein one and only one selected from $X_{17}$ and $X_{26}$ is K(2-[2-(2-amino-ethoxy)-ethoxy]-acetyl)$_2$-(γ-Glu)-CO—$(CH_2)_q$—$CO_2H$;

or a pharmaceutically acceptable salt thereof.

An embodiment 2 provides a compound, or a pharmaceutically acceptable salt thereof, of embodiment 1 wherein $Z_1$ is absent and $X_1$ is Y.

An embodiment 3 provides a compound, or pharmaceutically acceptable salt thereof, of embodiment 1 or embodiment 2 wherein $X_2$ is Aib.

An embodiment 4 provides a compound, or a pharmaceutically acceptable salt thereof, of any one of embodiments 1 to 3 wherein:

$X_6$ is selected from the group consisting of F and αMeF (2F).

An embodiment 5 provides a compound, or a pharmaceutically acceptable salt thereof, of any one of embodiments 1 to 4 wherein:

$X_{13}$ is selected from the group consisting of L and αMeL.

An embodiment 6 provides a compound, or a pharmaceutically acceptable salt thereof, of any one of embodiments 1 to 5 wherein $X_{16}$ is K or Orn An embodiment 7 provides a compound, or a pharmaceutically acceptable salt thereof, of embodiment 6 wherein $X_{16}$ is K.

An embodiment 8 provides a compound, or a pharmaceutically acceptable salt thereof, of any one of embodiments 1 to 7 wherein $X_{18}$ is H.

An embodiment 9 provides a compound, or a pharmaceutically acceptable salt thereof, of any one of embodiments 1 to 8 wherein $X_{20}$ is Aib; and $X_{22}$ is F.

An embodiment 10 provides a compound, or a pharmaceutically acceptable salt thereof, as claimed of any one of embodiments 1 to 9 wherein $X_{21}$ is D.

An embodiment 11 provides a compound, or a pharmaceutically acceptable salt thereof, of any one of embodiments 1 to 10 wherein $X_{25}$ is 4-Pal or Y.

An embodiment 12 provides a compound, or a pharmaceutically acceptable salt thereof, of any one of embodiments 1 to 11 wherein:

$X_{17}$ is K(2-[2-(2-amino-ethoxy)-ethoxy]-acetyl)$_2$-(γ-Glu)-CO—$(CH_2)_q$—$CO_2H$; and $X_{26}$ is L.

An embodiment 13 provides a compound, or a pharmaceutically acceptable salt thereof, of any one of embodiments 1 to 11 wherein:

$X_{17}$ is I; and $X_{26}$ is K(2-[2-(2-amino-ethoxy)-ethoxy]-acetyl)$_2$-(γ-Glu)-CO—$(CH_2)_q$—$CO_2H$.

An embodiment 14 provides a compound, or a pharmaceutically acceptable salt thereof, of any one of embodiments 1 to 13 wherein q is 16.

An embodiment 15 provides a compound, or a pharmaceutically acceptable salt thereof, of any one of embodiments 1 to 13 wherein q is 18.

An embodiment 16 provides a compound, or a pharmaceutically acceptable salt thereof, of embodiment 1 wherein:
$Z_1$ is absent;

$X_1$ is Y;

$X_2$ is selected from the group consisting of Aib and D-Ala $X_6$ is F;

$X_{13}$ is selected from the group consisting of αMeL and L;

$X_{16}$ is selected from the group consisting of K and Orn;

$X_{18}$ is selected from the group consisting of H and A;

$X_{20}$ is Aib;

$X_{22}$ is F;

$X_{24}$ is selected from the group consisting of E, N, and D-Glu;

$X_{25}$ is selected from the group consisting of Y, 4-Pal, and W;

$X_{28}$ is selected from the group consisting of E and A;

$X_{29}$ is selected from the group consisting of G, A, and Q; and q is selected from the group consisting of 16 and 18.

An embodiment 17 provides a compound, or a pharmaceutically acceptable salt thereof, of embodiment 16 wherein:

$Z_1$ is absent;

$X_2$ is Aib;

$X_{13}$ is αMeL;

$X_{18}$ is H;

$X_{24}$ is selected from the group consisting of E and D-Glu;

$X_{25}$ is selected from the group consisting of Y and 4-Pal;

$X_{28}$ is E;

$X_{29}$ is selected from the group consisting of G and A.

An embodiment 18 provides a compound, or a pharmaceutically acceptable salt thereof, of embodiment 17 wherein: $X_{17}$ is K(2-[2-(2-amino-ethoxy)-ethoxy]-acetyl)$_2$-(γ-Glu)-CO—$(CH_2)_q$—$CO_2H$; and $X_{26}$ is L.

An embodiment 19 provides a compound, or a pharmaceutically acceptable salt thereof, of embodiment 17 wherein: $X_{17}$ is I; and $X_{26}$ is K(2-[2-(2-amino-ethoxy)-ethoxy]-acetyl)$_2$-(γ-Glu)-CO—$(CH_2)_q$—$CO_2H$.

An embodiment 20 provides a compound, or a pharmaceutically acceptable salt thereof, of embodiment 1 wherein the compound is selected from the group consisting of SEQ ID NO:5, SEQ ID NO:6, SEQ ID NO:7. SEQ ID NO:8, SEQ ID NO:9, SEQ ID NO: 10, and SEQ ID NO: 11.

An embodiment 21 provides a compound or pharmaceutically acceptable salt thereof, of embodiment 1 wherein the compound is SEQ ID NO:5. An embodiment 22 provides a compound or pharmaceutically acceptable salt thereof, of embodiment 1 wherein the compound is SEQ ID NO:6. An embodiment 23 provides a compound or pharmaceutically acceptable salt thereof, of embodiment 1 wherein the compound is SEQ ID NO:7. An embodiment 24 provides a compound or pharmaceutically acceptable salt thereof, of embodiment 1 wherein the compound is SEQ ID NO:8. An embodiment 25 provides a compound or pharmaceutically acceptable salt thereof, of embodiment 1 wherein the compound is SEQ ID NO:9. An embodiment 26 provides a compound or pharmaceutically acceptable salt thereof, of embodiment 1 wherein the compound is SEQ ID NO:10. An embodiment 27 provides a compound or pharmaceutically acceptable salt thereof, of embodiment 1 wherein the compound is SEQ ID NO: 11.

An embodiment provides a method of treating a condition selected from the group consisting of diabetes, obesity, and metabolic syndrome, comprising administering to a subject in need thereof, an effective amount of a compound of any one of embodiments 1 to 27, or a pharmaceutically acceptable salt thereof. An embodiment provides a method of treating a condition selected from the group consisting of T2DM, obesity, and metabolic syndrome, comprising administering to a subject in need thereof, an effective amount of a compound of Formula I or a pharmaceutically acceptable salt thereof. An embodiment provides a method for providing therapeutic weight loss comprising administering to a subject in need thereof, an effective amount of a compound of Formula I, or a pharmaceutically acceptable salt thereof. An embodiment is a method of treating T2DM comprising administering to a subject in need thereof, and effective amount of a compound of any one of embodiments 1 to 27, or a pharmaceutically acceptable salt thereof.

An embodiment provides a compound of Formula I, or a pharmaceutically acceptable salt thereof, for use in therapy. An embodiment provides a compound of any one of embodiments 1 to 27, or a pharmaceutically acceptable salt thereof, for use in therapy to treat a condition selected from the group consisting of diabetes, obesity, and metabolic syndrome. An embodiment provides a compound of Formula I, or a pharmaceutically acceptable salt thereof, for use in therapy to treat a condition selected from the group consisting of T2DM, obesity, and metabolic syndrome. In an embodiment, the condition is T2DM. In an embodiment, the condition is obesity. In an embodiment, the condition is type 1 diabetes (T1DM). In an embodiment, the condition is diabetes in a patient receiving insulin therapy. In an embodiment, the condition is metabolic syndrome.

The compounds of Formula I, or a pharmaceutically acceptable salt thereof, may be useful in the treatment of a variety of symptoms or disorders. For example, certain embodiments provide a method for treatment of T2DM in a patient comprising administering to a subject in need of such treatment an effective amount of a compound of Formula I, or a pharmaceutically acceptable salt thereof. In an embodiment is a method for treatment of obesity in a patient comprising administering to a subject in need of such treatment an effective amount of a compound of Formula I, or a pharmaceutically acceptable salt thereof. In an embodiment, the method is inducing non-therapeutic weight loss in a subject, comprising administering to a subject in need of such treatment an effective amount of a compound of Formula I. or a pharmaceutically acceptable salt thereof.

In certain embodiments, the present invention provides a method for treatment of metabolic syndrome in a patient comprising administering to a subject in need of such treatment an effective amount of a compound of Formula I, or a pharmaceutically acceptable salt thereof. In an embodiment, the method is treatment of diabetes in a patient receiving insulin treatment, comprising administering to a subject in need of such treatment an effective amount of a compound of Formula I, or a pharmaceutically acceptable salt thereof. Also provided herein is a compound of the present invention for use in simultaneous, separate and sequential combinations with one or more agents selected from metformin, a thiazolidinedione, a sulfonylurea, a dipeptidyl peptidase 4 inhibitor, a sodium-glucose cotransporter-2 (SGLT-2) inhibitor, a growth differentiation factor 15 modulator ("GDF15"), a peptide tyrosine tyrosine modulator ("PYY"), a modified insulin, amylin, a dual amylin-calcitonin receptor agonist, and an oxyntomodulin agonist ("OXM") in the treatment of a condition selected from the group consisting of T2DM, obesity, and metabolic syndrome. Also provided herein is a compound of the present invention for use in simultaneous, separate, and sequential combinations with one or more agents selected from metformin, a thiazolidinedione, a sulfonylurea, a dipeptidyl peptidase 4 inhibitor, a sodium-glucose cotransporter-2 (SGLT-2) inhibitor, a growth differentiation factor 15 modulator ("GDF15"), a peptide tyrosine tyrosine analog ("PYY"), a modified insulin, an amylin receptor agonist, a dual amylin-calcitonin receptor agonist, a modified urocortin-2 (UCN-2) analog, a glucagon-like-peptide-1 (GLP-1) receptor agonist, a glucagon receptor agonist, and a dual GLP-1-glucagon receptor agonist including oxyntomodulin and analogs thereof, in the treatment of a condition selected from the group consisting of T2DM, obesity, and metabolic syndrome. In an embodiment, a compound of the present invention is provided in a fixed dose combination with one or more agents selected from metformin, a thiazolidinedione, a sulfonylurea, a dipeptidyl peptidase 4 inhibitor, a SGLT-2 inhibitor, GDF15. PYY, a modified insulin, amylin, a dual amylin-calcitonin receptor agonist, and OXM. In an embodiment, a compound of the present invention is provided in a fixed dose combination with one or more agents selected from metformin, a thiazolidinedione, a sulfonylurea, a dipeptidyl peptidase 4 inhibitor, a SGLT-2 inhibitor, GDF 15, a PYY analog, a modified insulin, an amylin receptor agonist, a dual amylin-calcitonin receptor agonist, a modified urocortin-2 (UCN-2) analog, a glucagon-like-peptide-1 (GLP-1) receptor agonist, a glucagon receptor agonist, and a dual GLP-1-glucagon receptor agonist including OXM and analogs thereof. In an embodiment is a compound of the present invention for use in simultaneous, separate and sequential combinations with one or more agents selected from metformin, a thiazolidinedione, a sulfonylurea, a dipeptidyl peptidase 4 inhibitor, a SGLT-2 inhibitor. GDF15, PYY, a modified insulin, amylin, a dual amylin-calcitonin receptor agonist, and OXM in the treatment of a condition selected from the group consisting of T2DM and obesity. In an embodiment is a compound of the present invention for use in simultaneous, separate and sequential combinations with one or more agents selected from metformin, a thiazolidinedione, a sulfonylurea, a dipeptidyl peptidase 4 inhibitor, a SGLT-2 inhibitor, GDF15, a PYY analog, a modified insulin, an amylin receptor agonist, a dual amylin-calcitonin receptor agonist, a modified urocortin-2 (UCN-2) analog, a glucagon-like-peptide-1 (GLP-1) receptor agonist, a glucagon receptor agonist, and a dual GLP-1 glucagon receptor agonist including OXM and analogs of, in the treatment of a condition selected from the group consisting of T2DM and obesity. In an embodiment is a compound of the present invention for use in simultaneous, separate and sequential combinations with one or more agents selected from metformin, a thiazolidinedione, a sulfonylurea, a dipeptidyl peptidase 4 inhibitor, and a SGLT-2 inhibitor in the treatment of a condition selected from the group consisting of T2DM and obesity.

In an embodiment is a method for treating diabetes in a patient receiving insulin therapy, comprising administering an effective amount of a Compound of Formula I or a pharmaceutically acceptable salt thereof, to a patient in need thereof. An embodiment is treatment to a patient administered insulin therapy for TIDM. An embodiment is treatment to patient administered insulin therapy for T2DM. An embodiment is once weekly dosing. An embodiment is subcutaneous treatment once weekly to a patient administered insulin therapy. An embodiment exists wherein the insulin therapy comprises basal insulin therapy. An embodiment exists wherein the insulin therapy comprises mealtime insulin therapy. An embodiment exists wherein the insulin therapy comprises ultra-rapid insulin therapy. Insulin therapy administered with acute infusions of a compound of Formula I, or a pharmaceutically acceptable salt thereof, may enhance glucagon excursion in patients undergoing hypoglycemic clamp, thus enhancing the body's natural defense against hypoglycemia. A compound of Formula I, or a pharmaceutically acceptable salt thereof, can be dosed once weekly independent of the type of insulin used or doses of insulin used. An embodiment is a compound of any one of embodiments 1 to 27, or a pharmaceutically acceptable salt thereof, administered as an effective amount to a patient receiving insulin therapy, independent of the type of insulin used or doses of insulin used. An embodiment is a compound of any one of embodiments 1 to 27, or a pharmaceutically acceptable salt thereof, dosed once weekly as an effective amount to a patient receiving insulin therapy independent of the type of insulin used or doses of insulin used. As used herein "insulin therapy" means treatment of a patient with diabetes using an approved insulin treatment. Such insulin therapy is known to the skilled artisan and/or clinical health care professional. For example, insulin therapy may comprise treatment using basal insulin. Such basal insulin "insulin therapy" may be used in a dosing regimen with mealtime insulin and/or ultra-rapid insulin. As used herein, "mealtime insulin" means insulin and/or modified insulin to be administered with meals, for example, but not limited to, insulin lispro. As used herein, "basal insulin"

means modified insulin with a longer duration of action, such as, for example, but not limited to, insulin glargine.

Another embodiment provides the use of a compound of Formula I, or a pharmaceutically acceptable salt thereof, in the manufacture of a medicament for the treatment of a condition selected from the group consisting of T2DM, obesity, and metabolic syndrome. An embodiment provides the use of a compound of any one of embodiments 1 to 27, or a pharmaceutically acceptable salt thereof, in the manufacture of a medicament for the treatment of a condition selected from the group consisting of diabetes, obesity, and metabolic syndrome. In an embodiment, the medicament is for the treatment of T2DM. In an embodiment, the medicament is for the treatment of obesity. In an embodiment, the medicament is for use in the treatment of diabetes in a patient receiving insulin therapy.

Another embodiment provides a pharmaceutical composition comprising a compound of Formula I, or a pharmaceutically acceptable salt thereof, and at least one selected from the group consisting of a carrier, diluent, and excipient. In an embodiment, a pharmaceutical composition for subcutaneous administration is provided.

As used herein, the term "treating" or "to treat" includes restraining, slowing, stopping, or reversing the progression or severity of a symptom, condition, or disorder.

Certain compounds of the present invention are generally effective over a wide dosage range. For example, dosages for once weekly parenteral dosing may fall within the range of 0.05 mg to about 60 mg per person per week.

The compounds of Formula I, or a pharmaceutically acceptable salt thereof, include novel amino acid sequences having affinity for the GIP receptor, with desired potency at the receptor. GIP is a 42 amino acid peptide (SEQ ID NO:1), which, like GLP-1, is known as an incretin, and it plays a physiological role in glucose homeostasis by stimulating insulin secretion from pancreatic beta cells in the presence of glucose.

GLP-1 is a 36 amino acid peptide, the major biologically active fragment of which is produced as a 30-amino acid, C-terminal amidated peptide (GLP-17-36) (SEQ ID NO:2).

Glucagon is a 29-amino acid peptide hormone (SEQ ID NO:3) secreted by a-cells of the islet of Langerhans in the pancreas and is involved in glucose homeostasis.

The compounds of present invention provide desired potency at the GIP receptor with high degree of selectivity against the GLP-1R and the Glucagon receptor. In an embodiment, compounds have desired GIP receptor activity with extended duration of action.

As used herein the term "amino acid" means both naturally occurring amino acids and unnatural amino acids. The amino acids are typically depicted using standard one letter codes (e.g., L=leucine), as well as alpha-methyl substituted residues of natural amino acids (e.g., α-methyl leucine, or αMeL, and α-methyl phenylalanine, or αMeF) and certain other unnatural amino acids, such as alpha-amino isobutyric acid, or "Aib," "4Pal," "Orn," and the like. The structures of these amino acids appear below:

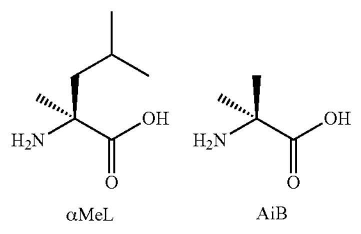

αMeL AiB

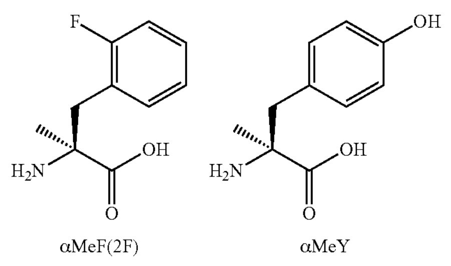

αMeF(2F) αMeY

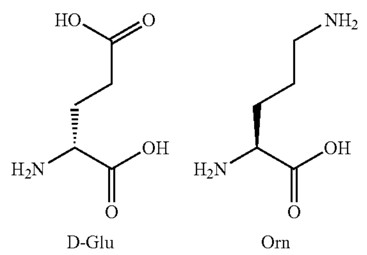

D-Glu Orn

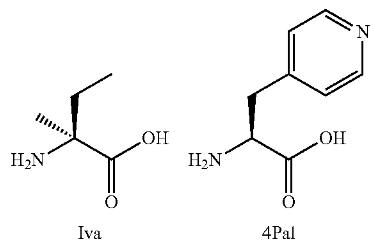

Iva 4Pal

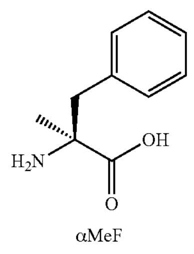

αMeF

As used herein. “Orn” means L-ornithine. As used herein. “4Pal” means 3-(4-Pyridyl)-L-alanine. As used herein, “αMeF(2F)” means alpha-methyl 2-fluoro-L-phenylalanine. As used herein, “αMeY” and “αMeL” mean alpha-methyl-L-tyrosine and alpha-methyl-L-leucine, respectively. As used herein, “e” and “D-Glu” mean D-glutamic acid. As used herein, “D-Tyr” and “y” each mean D-tyrosine. As used herein, “D-Ala” and “a” each mean D-alanine. As used herein, “αMeF” means alpha-methyl-F and alpha-methyl-Phe. As used herein “Iva” means L-isovaline.

In an embodiment, the conjugation is an acylation. In an embodiment, the conjugation is to the epsilon-amino group of the K side-chain. In an embodiment of the compounds of the present invention, a fatty acid moiety is conjugated, via a linker, to a K at position 17. In an embodiment of the compounds of the present invention, a fatty acid moiety is conjugated, via a linker, to a K at position 26.

In an embodiment, q is selected from the group consisting of 16 and 18. In an embodiment, q is 16. In an embodiment, q is 18.

When used herein in reference to the GIP receptor the terms “activity.” “activate[s]” “activat[ing]” and the like refers to the capacity of a compound, or a pharmaceutically acceptable salt thereof, to bind to and induce a response at the receptor, as measured using assays known in the art, such as the in vitro assays described below.

The affinity of compounds of Formula I, or a pharmaceutically acceptable salt thereof, for the GIP receptor may be measured using techniques known for measuring receptor binding levels in the art, including, for example, those described in the examples below, and is commonly expressed as a $K_i$ value. The activity of the compounds of the present invention at the GIP receptor may also be measured using techniques known in the art, including for example the in vitro activity assays described below, and is commonly expressed as an $EC_{50}$ value, which is the concentration of compound causing half-maximal simulation in a dose response curve.

In addition, data is provided for each compound for activity and affinity at the GLP-1 and glucagon receptors, to demonstrate the degree of selectivity of the compounds of the present invention for the GIPR.

In an embodiment, a pharmaceutical composition of a compound of Formula I is suitable for administration by a parenteral route (e.g., subcutaneous, intravenous, intraperitoneal, intramuscular, or transdermal). Some pharmaceutical compositions and processes for preparing same are well known in the art. (See. e.g., Remington: The Science and Practice of Pharmacy (D. B. Troy, Editor, 21st Edition. Lippincott, Williams & Wilkins. 2006)).

Compounds of the present invention may react with any of a number of inorganic and organic acids/bases to form pharmaceutically acceptable acid/base addition salts. Pharmaceutically acceptable salts and common methodology for preparing them are well known in the art. (Sec, e.g., P. Stahl, et al. Handbook of Pharmaceutical Salts: Properties, Selection and Use, 2nd Revised Edition (Wiley-VCH, 2011)). Pharmaceutically acceptable salts of the present invention include, but are not limited to, sodium, trifluoroacetate, hydrochloride, ammonium, and acetate salts. In an embodiment, a pharmaceutically acceptable salt is selected from the group consisting of sodium, hydrochloride, and acetate salts.

The present invention also encompasses novel intermediates and processes useful for the synthesis of compounds of the present invention, or a pharmaceutically acceptable salt thereof. The intermediates and compounds of the present invention may be prepared by a variety of procedures known in the art. In particular, the Examples below describe a process using chemical synthesis. The specific synthetic steps for each of the routes described may be combined in different ways to prepare compounds of the present invention. The reagents and starting materials are readily available to one of ordinary skill in the art.

When used herein, the term “effective amount” refers to the amount or dose of a compound of the present invention, or a pharmaceutically acceptable salt thereof, which, upon single or multiple dose administration to the patient, provides the desired effect in the patient under diagnosis or treatment. An effective amount can be determined by a person of skill in the art using known techniques and by observing results obtained under analogous circumstances. In determining the effective amount for a subject, a number of factors are considered, including, but not limited to; the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication, and other relevant circumstances.

When used herein, the term “subject in need thereof” refers to a mammal, preferably a human, with a disease or condition requiring treatment or therapy, including for example those listed in the preceding paragraphs.

As used herein. “EDTA” means ethylenediaminetetraacetic acid. As used herein, “DMSO” means dimethyl sulfoxide. As used herein. “CPM” means counts per minute. As used herein, “IBMX” means 3-isobutyl-1-methylxanthine. As used herein, “LC/MS” means liquid chromatography/mass spectrometry. As used herein, “HTRF” means homogeneous time-resolved fluorescence. As used herein, “DMF” refers to N,N-dimethylformamide. As used herein, “DCM” refers to dichloromethane. As used herein, “TFA” refers to trifluoroacetic acid. As used herein, “TFA salt” refers to trifluoroacetate salt. As used herein, “RP-HPLC” means reversed-phase high performance liquid chromatography.

The invention is further illustrated by the following examples, which are not to be construed as limiting.

Peptide Synthesis

EXAMPLE 1

Y-(D-Ala)-EGTFISDYSILLDKK((2-[2-(2-Amino-ethoxy)-ethoxy]-acetyl)$_2$-(γ-Glu)-CO—$(CH_2)_{18}$—$CO_2H$)AQ-Aib-DFVNWLLAQGPSSGAPPPS-$NH_2$ (SEQ ID NO:5)

The structure of SEQ ID NO:5 is depicted below using the standard single letter amino acid codes with the exceptions of residues D-Ala2, K17, Aib20, and Ser39, where the structures of these amino acid residues have been expanded:

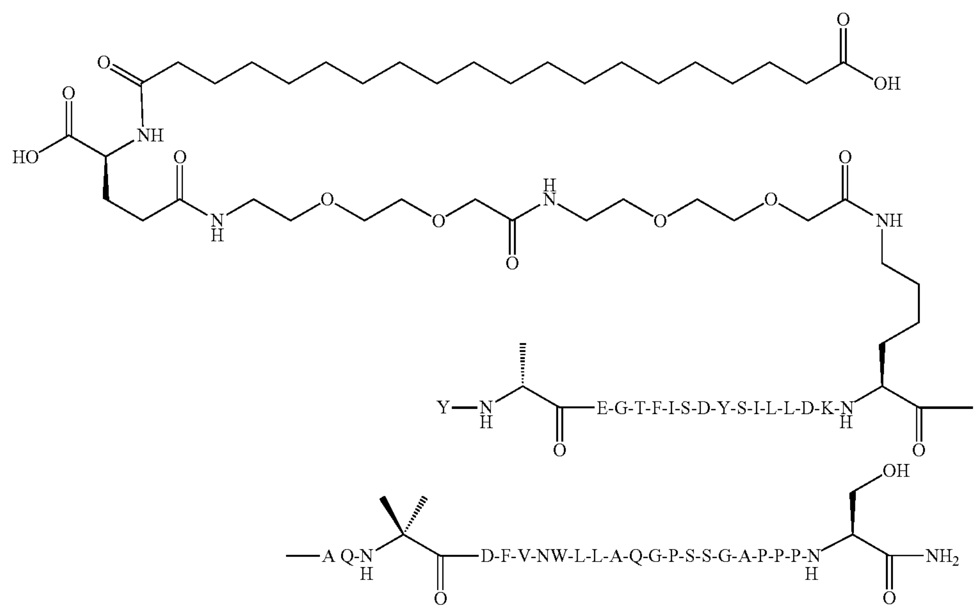

The peptide backbone of Example 1 is synthesized using fluorenylmethyloxycarbonyl (Fmoc)/tert-butyl (t-Bu) chemistry on a Symphony multiplex peptide synthesizer (Gyros Protein Technologies. Tucson, AZ; 3.3.0.1), software version 3.3.0.

The resin consists of aminomethyl polystyrene functionalized with a Rink Amide linker (polystyrene AM RAM, RAPP polymeric GmbH, H40023, 200-400 mesh) at a substitution of 0.8 mmol/g Standard side-chain protecting groups are used with the following exceptions: Fmoc-Lys (Mtt)-OH, where Mtt is 4-methyltrityl, is used for the lysine at position 17 and Boc-Tyr(t-Bu)-OH is used for the tyrosine at position 1. Fmoc groups are removed prior to each coupling step (2×10 minutes) using 20% piperidine in DMF. All standard amino acid couplings are performed using an equal molar ratio of Fmoc amino acid (0.3 M in DMF), diisopropylcarbodiimide (0.9 M in DCM) and Oxyma (0.9 M in DMF) at a 9-fold molar excess over the theoretical peptide loading. Couplings are allowed to proceed for 1.5 hours, with the following exceptions: coupling of valine, 3 hours; coupling of Ca-methylated amino acids, 6 hours; coupling to Cα-methylated amino acids, 6-10 hours. After completion of the synthesis of the peptide backbone, the resin is thoroughly washed with DCM to remove residual DMF. The Mtt protecting group on the lysine at position 17 is selectively removed from the peptide resin using three treatments of 30% hexafluoroisopropanol (Oakwood Chemicals) in DCM (3×20-minute treatment), and the resin is thoroughly washed with DCM and DMF.

Subsequent attachment of the fatty acid-linker moiety is accomplished by coupling of 2-[2-(2-Fmoc-amino-ethoxy)-ethoxy]-acetic acid (Fmoc-AEEA-OH, ChemPep. Inc.) and Fmoc-glutamic acid α-t-butyl ester (Fmoc-Glu-OtBu. Ark Pharm. Inc.) following the procedures described above for standard coupling and deprotection reactions. After removal of the final Fmoc protecting group, mono-OtBu-eicosanedioic acid (WuXi AppTec, Shanghai, China) is coupled for 1 hour using a 4-fold excess of the diacid, PyBOP, and diisopropylethylamine (1:1:1 mol/mol/mol) in 1:1 DCM/DMF.

After the synthesis is complete, the peptide-resin is washed with DCM and then thoroughly dried over vacuum. The dry peptide-resin is treated with cleavage cocktail (10 mL TFA, 0.5 mL triisopropylsilane. 0.5 mL water, and 0.5 mL 1,2-ethanedithiol) for 2 hours at room temperature. The peptide resin solution is filtered into a 50-mL conical centrifuge tube and treated with 5-fold excess volume of cold diethyl ether (−20° C.) to precipitate the crude peptide. The peptide/ether suspension is centrifuged at 3000 rcf for 1.5 min, to form a solid pellet and the supernatant is decanted. The pellet is washed further two times with cold diethyl ether, centrifuging for 1 min. each time, then dried in vacuo. The crude peptide is solubilized in 20% acetic acid/80% water and purified by RP-HPLC on a Symmetry Prep 7 μm C18 preparative column (18×300 mm, Waters) with linear gradients of 100% acetonitrile and 0.1% TFA/water buffer system (25-45% acetonitrile in 65 min). The purity of peptide is assessed using analytical RP-HPLC and pooling criteria is >95%. The main pool purity of compound of example I is found to be 96.8%. Subsequent lyophilization of the final main product pool yielded the lyophilized peptide TFA salt. The molecular weight is determined by LC/MS (Found: $[M+3H]^{3+}$=1638.4; Calculated $[M+3H]^{3+}$ =1638.53; Found MW (avg)=4912.2. Calc. MW (avg): 4912.58).

EXAMPLE 2

Y-(D-Ala)-EGTFISDYSILLDKK((2-[2-(2-Amino-ethoxy)-ethoxy]-acetyl)$_2$-(γ-Glu)-CO—$(CH_2)_{16}$—$CO_2H$)AQ-Aib-DFVNWLLAQGPSSGAPPPS-$NH_2$ (SEQ ID NO:6)

The structure of SEQ ID NO:6 is depicted below using the standard single letter amino acid codes with the exceptions of residues D-Ala2, K17, Aib20, and Ser39, where the structures of these amino acid residues have been expanded:

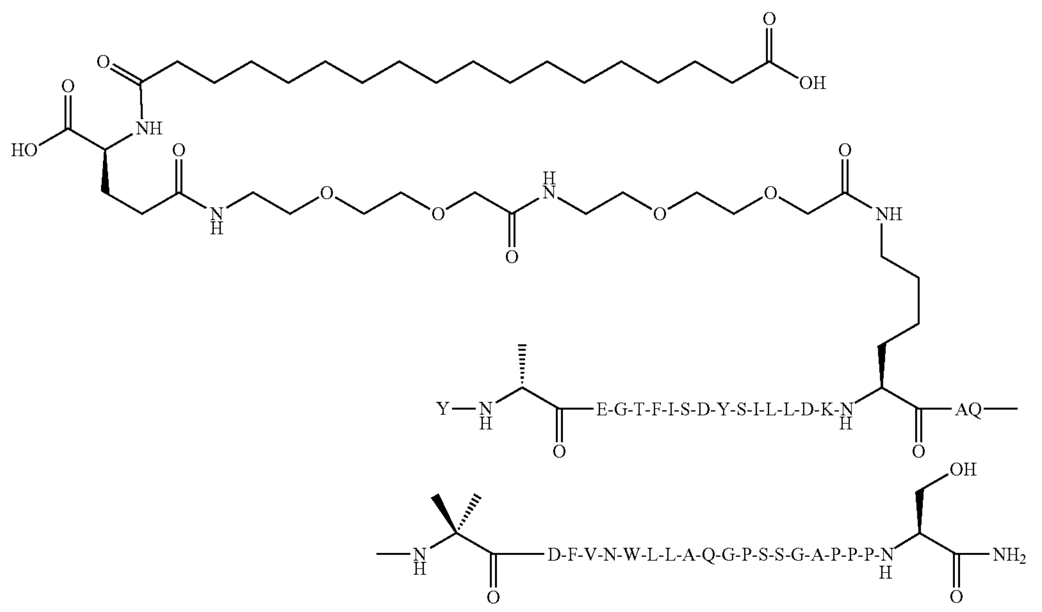

The compound according to SEQ ID NO:6 is prepared substantially as described by the procedures of Example 1, where instead the protected diacid is mono-OtBu-octadecanedioic acid (WuXi AppTec, Shanghai, China). The molecular weight is determined by LC/MS (Found: $[M+3H]^{3+}$=1629.15; Calc. $[M+3H]^{3+}$=1629.18; Found MW (avg)= 4884.45; Calc. MW (avg)=4884.53).

EXAMPLE 3

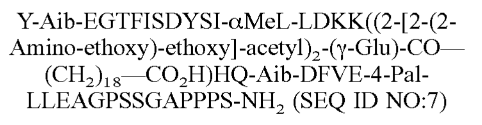

Y-Aib-EGTFISDYSI-αMeL-LDKK((2-[2-(2-Amino-ethoxy)-ethoxy]-acetyl)$_2$-(γ-Glu)-CO—$(CH_2)_{18}$—$CO_2$H)HQ-Aib-DFVE-4-Pal-LLEAGPSSGAPPPS-$NH_2$ (SEQ ID NO:7)

The structure of SEQ ID NO:7 is depicted below using the standard single letter amino acid codes with the exceptions of residues Aib2, αMeL13, K17, Aib20, 4-Pal25, and Ser39, where the structures of these amino acid residues have been expanded:

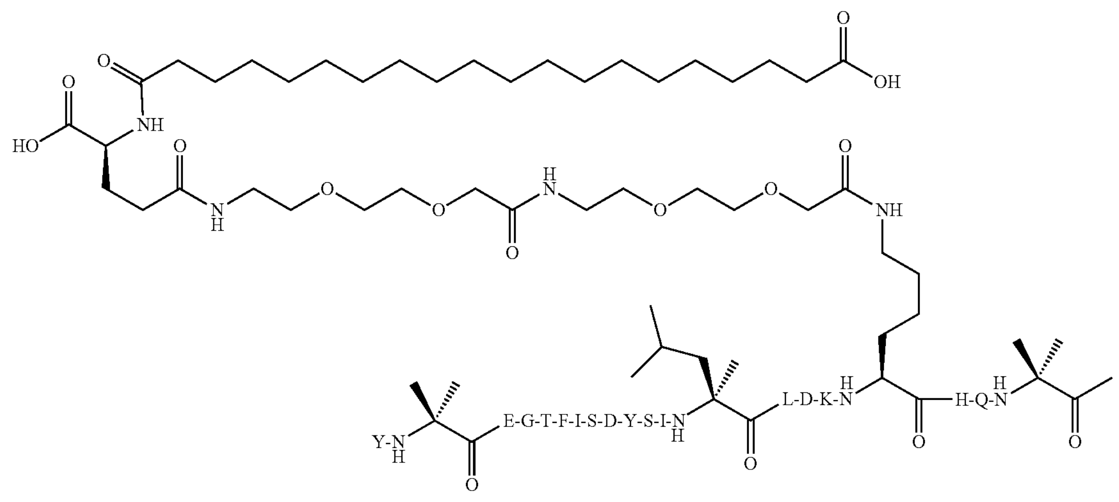

-continued

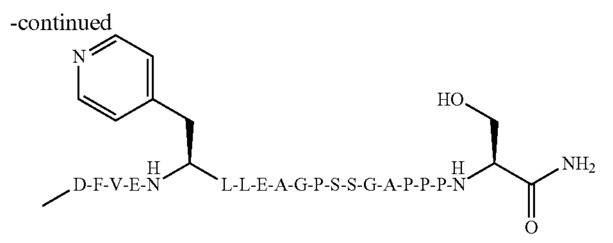

The compound according to SEQ ID NO:7 is prepared substantially as described by the procedures of Example 1. The molecular weight is determined by LC/MS (Found: $[M+3H]^{3+}$=1662.52; Calc. $[M+3H]^{3+}$=1662.55; Found MW (avg)=4984.55; Calc. MW (avg)-4984.64).

EXAMPLE 4

Y-Aib-EGTFISDYSI-αMeL-LD-Orn-K((2-[2-(2-Amino-ethoxy)-ethoxy]-acetyl)$_2$-(γ-Glu)-CO—$(CH_2)_{18}$—$CO_2$H)HQ-Aib-DFVE-4-Pal-LLEAGPSSGAPPPS-$NH_2$ (SEQ ID NO:8)

The structure of SEQ ID NO:8 is depicted below using the standard single letter amino acid codes with the exceptions of residues Aib2, αMeL13, Orn16, K17, Aib20, 4-Pal25, and Ser39, where the structures of these amino acid residues have been expanded:

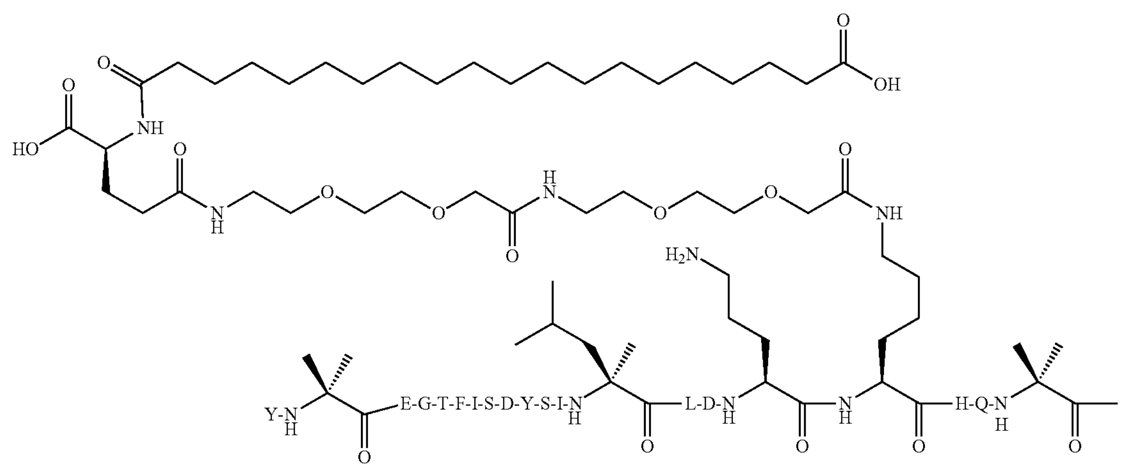

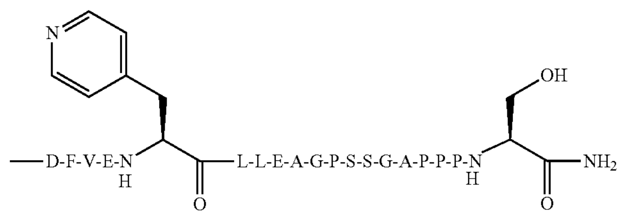

The compound according to SEQ ID NO:8 is prepared substantially as described by the procedures of Example 1. The molecular weight is determined by LC/MS (Found: $[M+3H]^{3+}$=1657.82; Calc. $[M+3H]^{3+}$=1657.87; Found MW (avg)=4970.46; Calc. MW (avg)=4970.62).

EXAMPLE 5

Y-Aib-EGTFISDYSI-αMeL-LDKIHQ-Aib-DFVEYK((2-[2-(2-Amino-ethoxy)-ethoxy]-acetyl)$_2$-(γ-Glu)-CO—$(CH_2)_{18}$—$CO_2$H)LEGGPSSGAPPPS-$NH_2$ (SEQ ID NO:9)

The structure of SEQ ID NO:9 is depicted below using the standard single letter amino acid codes with the exceptions of residues Aib2, αMeL13, Aib20, K26, and Ser39, where the structures of these amino acid residues have been expanded:

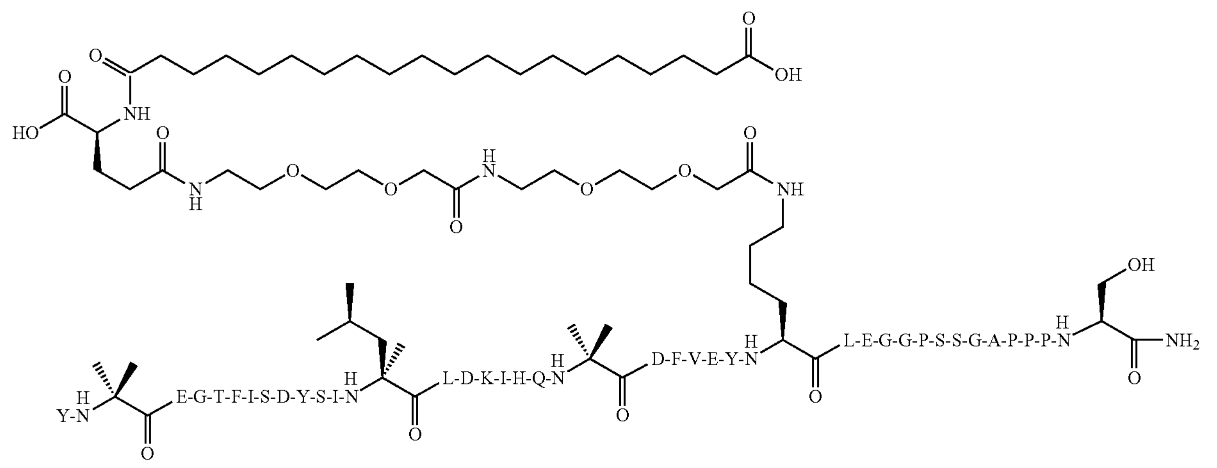

The compound according to SEQ ID NO:9 is prepared substantially as described by the procedures of Example 1, where Fmoc-Lys(Mtt)-OH is used for the lysine at position 26 rather than at position 17. The molecular weight is determined by LC/MS (Found: $[M+3H]^{3+}$=1662.8; Calc. $[M+3H]^{3+}$=1662.88; Found MW (avg)-4985.4; Calc. MW (avg)=4985.63).

EXAMPLE 6

Y-Aib-EGTFISDYSI-αMeL-LD-Orn-IHQ-Aib-DFVEYK((2-[2-(2-Amino-ethoxy)-ethoxy]-acetyl)$_2$-(γ-Glu)-CO—$(CH_2)_{18}$—$CO_2$H)LEGGPSSGAPPPS-$NH_2$ (SEQ ID NO:10)

The structure of SEQ ID NO:10 is depicted below using the standard single letter amino acid codes with the exceptions of residues Aib2, αMeL13, Orn16, Aib20, K26, and Ser39, where the structures of these amino acid residues have been expanded:

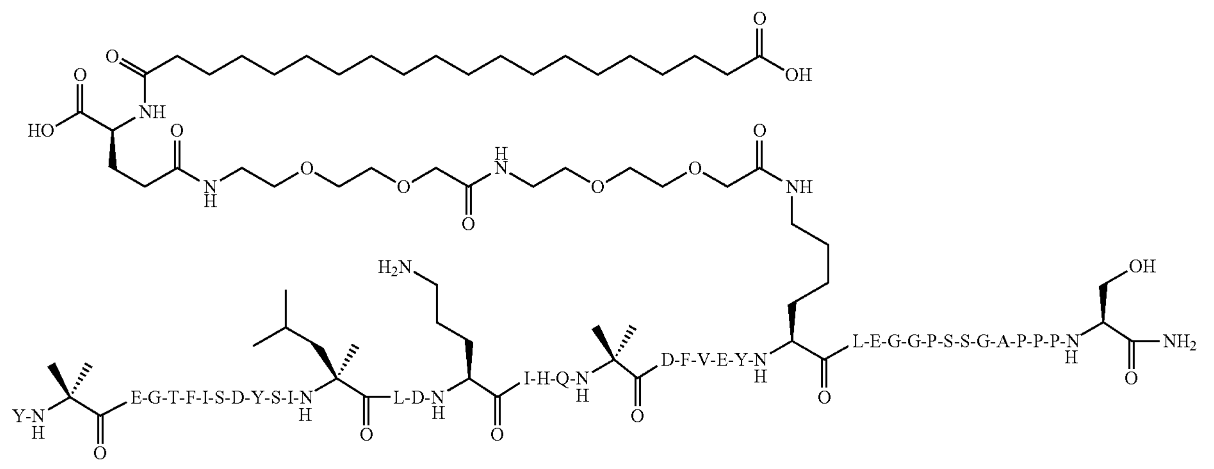

The compound according to SEQ ID NO:10 is prepared substantially as described by the procedures of Example 1, where Fmoc-Lys(Mtt)-OH is used for the lysine at position 26 rather than at position 17. The molecular weight is determined by LC/MS (Found: $[M+3H]^{3+}$=1658.1; Calc. $[M+3H]^{3+}$=1658.20; Found MW (avg)=4971.3; Calc. MW (avg)=4971.6).

EXAMPLE 7

Y-Aib-EGTFISDYSI-αMeL-LD-Orn-IHQ-Aib-EFV-(D-Glu)-YK((2-[2-(2-Amino-ethoxy)-ethoxy]-acetyl)$_2$-(γ-Glu)-CO—$(CH_2)_{16}$—$CO_2$H)LEGGPSSGAPPPS-$NH_2$ (SEQ ID NO:11)

The structure of SEQ ID NO:11 is depicted below using the standard single letter amino acid codes with the exceptions of residues Aib2, αMeL13, Orn16, Aib20, D-Glu24, K26, and Ser39, where the structures of these amino acid residues have been expanded:

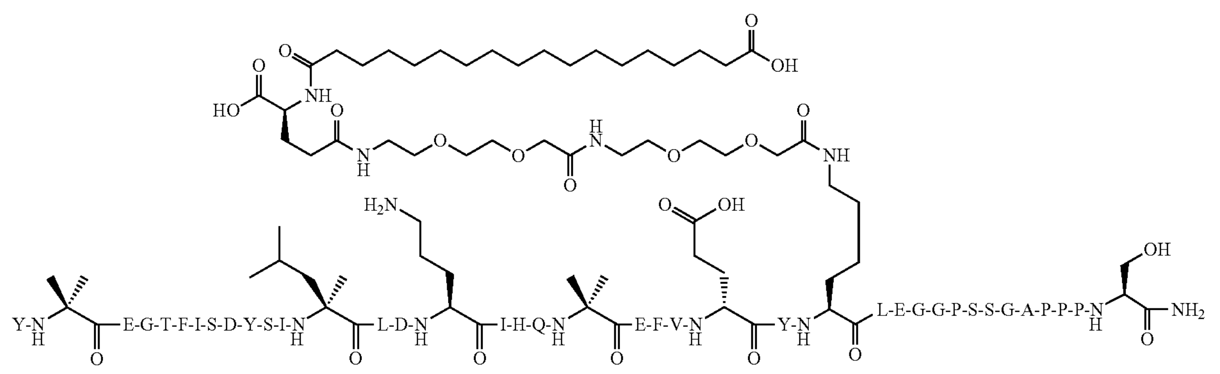

The compound according to SEQ ID NO:11 is prepared substantially as described by the procedures of Example 1, where Fmoc-Lys(Mtt)-OH is used for the lysine at position 26 rather than at position 17 and the protected diacid is mono-OtBu-octadecanedioic acid (WuXi AppTec, Shanghai, China). The molecular weight is determined by LC/MS (Found: $[M+3H]^{3+}$=1653.4; Calc. $[M+3H]^{3+}$=1653.52; Found MW (avg)=4957.2; Calc. MW (avg)-4957.57).

The compounds according to Example 8 (SEQ ID NO:12) through Example 122 (SEQ ID NO:126) are prepared substantially as described by the procedures of Example 1.

| Example | SEQ ID NO | Compound Name | Calculated (avg) MW | Found (avg) MW |
|---|---|---|---|---|
| 8 | 12 | Y-(Aib)-EGTFISDYSILLDKK((2-[2-(2-Amino-ethoxy)-ethoxy]-acetyl)$_2$-(γ-Glu)-CO-$(CH_2)_{18}$-$CO_2$H)AQ-(Aib)-DFVNWLLAQGPSSGAPPPS-$NH_2$ | 4926.61 | 4926.6 |
| 9 | 13 | Y-(D-Ala)-EGTFISDYSILLDKK((2-[2-(2-Amino-ethoxy)-ethoxy]-acetyl)$_2$-(γ-Glu-CO-$(CH_2)_{18}$-$CO_2$H)HQ-(Aib)-DFVNWLLAQGPSSGAPPPS-$NH_2$ | 4978.64 | 4978.4 |
| 10 | 14 | Y-(D-Ala)-EGTFISDYSILLDKK((2-[2-(2-Amino-ethoxy)-ethoxy]-acetyl)$_2$-(γ-Glu)-CO-$(CH_2)_{18}$-$CO_2$H)HQQDFVNWLLAGGPSSGAPPPS-$NH_2$ | 4950.59 | 4950.4 |
| 11 | 15 | Y-(D-Ala)-EGTFISDYSILLDKK((2-[2-(2-Amino-ethoxy)-ethoxy]-acetyl)$_2$-(γ-Glu)-CO-$(CH_2)_{18}$-$CO_2$H)AQQDFVNWLLAQGPSSGAPPPS-$NH_2$ | 4955.61 | 4955.2 |

-continued

| Example | SEQ ID NO | Compound Name | Calculated (avg) MW | Found (avg) MW |
|---|---|---|---|---|
| 12 | 16 | Y-(D-Ala)-EGTFISDYSILLDKK((2-[2-(2-Amino-ethoxy)-ethoxy]-acetyl)$_2$-(γ-Glu)-CO-$(CH_2)_{18}$-$CO_2H$)AQQDFVNWLLAGGPSSGAPPPS-$NH_2$ | 4884.53 | 4884.4 |
| 13 | 17 | Y-(D-Ala)-EGTFISDYSILLDKK((2-[2-(2-Amino-ethoxy)-ethoxy]-acetyl)$_2$-(γ-Glu)-CO-$(CH_2)_{18}$-$CO_2H$)HQQEFVNWLLAQGPSSGAPPPS-$NH_2$ | 5035.7 | 5035.2 |
| 14 | 18 | Y-(D-Ala)-EGTFISDYSILLDKK((2-[2-(2-Amino-ethoxy)-ethoxy]-acetyl)$_2$-(γ-Glu)-CO-$(CH_2)_{18}$-$CO_2H$)HQQDFVEWLLAQGPSSGAPPPS-$NH_2$ | 5036.68 | 5036.8 |
| 15 | 19 | Y-(D-Ala)-EGTFISDYSILLDKK((2-[2-(2-Amino-ethoxy)-ethoxy]-acetyl)$_2$-(γ-Glu)-CO-$(CH_2)_{18}$-$CO_2H$)HQQDFVNYLLAQGPSSGAPPPS-$NH_2$ | 4998.63 | 4998.4 |
| 16 | 20 | Y-(D-Ala)-EGTFISDYSILLDKK((2-[2-(2-Amino-ethoxy)-ethoxy]-acetyl)$_2$-(γ-Glu)-CO-$(CH_2)_{16}$-$CO_2H$)AQ-(Aib)-DFVEWLLAQGPSSGAPPPS-$NH_2$ | 4899.54 | 4899.3 |
| 17 | 21 | Y-(D-Ala)-EGTFISDYSILLDKK((2-[2-(2-Amino-ethoxy)-ethoxy]-acetyl)$_2$-(γ-Glu)-CO-$(CH_2)_{16}$-$CO_2H$)AQ-(Aib)-DFVNWLLEQGPSSGAPPPS-$NH_2$ | 4942.56 | 4941.9 |
| 18 | 22 | Y-(D-Ala)-EGTFISDYSILLDKK((2-[2-(2-Amino-ethoxy)-ethoxy]-acetyl)$_2$-(γ-Glu)-CO-$(CH_2)_{16}$-$CO_2H$)AQ-(Aib)-DFVN-(4-Pal)-LLAQGPSSGAPPPS-$NH_2$ | 4846.48 | 4846.5 |
| 19 | 23 | Y-(D-Ala)-EGTFISDYSILLDKK((2-[2-(2-Amino-ethoxy)-ethoxy]-acetyl)$_2$-(γ-Glu)-CO-$(CH_2)_{16}$-$CO_2H$)AQ-(Aib)-DFVNWLLAGGPSSGAPPPS-$NH_2$ | 4813.45 | 4813.2 |
| 20 | 24 | Y-(D-Ala)-EGTFISDYSILLDKK((2-[2-(2-Amino-ethoxy)-ethoxy]-acetyl)$_2$-(γ-Glu)-CO-$(CH_2)_{16}$-$CO_2H$)AQ-(Aib)-EFVNWLLAQGPSSGAPPPS-$NH_2$ | 4898.55 | 4898.4 |
| 21 | 25 | Y-(Aib)-EGTFISDYSIALDKK((2-[2-(2-Amino-ethoxy)-ethoxy]-acetyl)$_2$-(γ-Glu)-CO-$(CH_2)_{16}$-$CO_2H$)HQ-(Aib)-DFVE-(4-Pal)-LLAGGPSSGAPPPS-$NH_2$ | 4828.42 | 4827.9 |
| 22 | 26 | Y-(Aib)-EGTFISDYSILLDKK((2-[2-(2-Amino-ethoxy)-ethoxy]-acetyl)$_2$-(γ-Glu)-CO-$(CH_2)_{16}$-$CO_2H$)HQ-(Aib)-DFVE-(4-Pal)-LLAGGPSSGAPPPS-$NH_2$ | 4870.5 | 4870.5 |
| 23 | 27 | Y-(Aib)-EGT-(αMeF)-ISDYSIALDKK((2-[2-(2-Amino-ethoxy)-ethoxy]-acetyl)$_2$-(γ-Glu)-CO-$(CH_2)_{16}$-$CO_2H$)HQ-(Aib)-DFVE-(4-Pal)-LLAGGPSSGAPPPS-$NH_2$ | 4842.45 | 4842.3 |
| 24 | 28 | Y-(Aib)-EGTFISDYSI-(Aib)-LDKK((2-[2-(2-Amino-ethoxy)-ethoxy]-acetyl)$_2$-(γ-Glu)-CO-$(CH_2)_{16}$-$CO_2H$)HQ-(Aib)-DFVE-(4-Pal)-LLAGGPSSGAPPPS-$NH_2$ | 4842.45 | 4842.3 |
| 25 | 29 | Y-(Aib)-EGT-(αMeF)-ISDYSIALDKK((2-[2-(2-Amino-ethoxy)-ethoxy]-acetyl)$_2$-(γ-Glu)-CO-$(CH_2)_{18}$-$CO_2H$)HQ-(Aib)-EFVNAVLLAGGPSSGAPPPS-$NH_2$ | 4907.56 | 4907.1 |

-continued

| Example | SEQ ID NO | Compound Name | Calculated (avg) MW | Found (avg) MW |
|---|---|---|---|---|
| 26 | 30 | Y-(Aib)-EGT-αMeF(2F)-ISDYSIALDKK((2-[2-(2-Amino-ethoxy)-ethoxy]-acetyl)$_2$-(γ-Glu)-CO-(CH$_2$)$_{18}$-CO2H)HQ-(Aib)-EFVNWLLAGGPSSGAPPPS-NH$_2$ | 4925.56 | 4925.4 |
| 27 | 31 | Y-(D-Ala)-EGTFISDYSILLDKK((2-[2-(2-Amino-ethoxy)-ethoxy]-acetyl)$_2$-(γ-Glu)-CO-(CH$_2$)$_{16}$-CO$_2$H)AQ-(Aib)-EFVQWLLAGGPSSGAPPPS-NH$_2$ | 4841.5 | 4841.4 |
| 28 | 32 | Y-(D-Ala)-EGTFISDYSILLDKK((2-[2-(2-Amino-ethoxy)-ethoxy]-acetyl)$_2$-(γ-Glu)-CO-(CH$_2$)$_{16}$-CO$_2$H)AQ-(Aib)-EFVNWLLEGGPSSGAPPPS-NH$_2$ | 4885.51 | 4885.2 |
| 29 | 33 | Y-(D-Ala)-EGTFISDYSILLDKK((2-[2-(2-Amino-ethoxy)-ethoxy]-acetyl)$_2$-(γ-Glu)-CO-(CH$_2$)$_{16}$-CO$_2$H)AQ-(Aib)-EFVEWLLAGGPSSGAPPPS-NH$_2$ | 4842.49 | 4842.45 |
| 30 | 34 | Acetyl-(D-Tyr)-AEGT-αMeF(2F)-ISDYSIALDKK((2-[2-(2-Amino-ethoxy)-ethoxy]-acetyl)$_2$-(γ-Glu)-CO-(CH$_2$)$_{16}$-CO$_2$H)HQ-(Aib)-EFVNYLLAGGPSSGAPPPS-NH$_2$ | 4902.47 | 4902.0 |
| 31 | 35 | Y-(Aib)-EGTFISDYSILLDKK((2-[2-(2-Amino-ethoxy)-ethoxy]-acetyl)$_2$-(γ-Glu)-CO-(CH$_2$)$_{16}$-CO$_2$H)HQ-(Aib)-DFVNYLLAAGPSSGAPPPS-NH$_2$ | 4884.53 | 4884.6 |
| 32 | 36 | Y-(D-Ala)-EGTLISDYSILLDKK((2-[2-(2-Amino-ethoxy)-ethoxy]-acetyl)$_2$-(γ-Glu)-CO-(CH$_2$)$_{16}$-CO$_2$H)AQ-(Aib)-DFVNWLLAQGPSSGAPPPS-NH$_2$ | 4850.51 | 4850.4 |
| 33 | 37 | Acetyl-(D-Tyr)-AEGT-αMeF(2F)-ISDYSIALDKK((2-[2-(2-Amino-ethoxy)-ethoxy]-acetyl)$_2$-(γ-Glu)-CO-(CH$_2$)$_{18}$-CO$_2$H)HQ-(Aib)-EFVNYLLEGGPSSGAPPPS-NH$_2$ | 4988.56 | 4988.1 |
| 34 | 38 | Y-(Aib)-EGT-αMeF(2F)-ISDYSIALDKK((2-[2-(2-Amino-ethoxy)-ethoxy]-acetyl)$_2$-(γ-Glu)-CO-(CH$_2$)$_{18}$-CO$_2$H)HQ-(Aib)-EFVNYLLATGPSSGAPPPS-NH$_2$ | 4946.57 | 4946.4 |
| 35 | 39 | Y-(Aib)-EGT-(αMeL)-ISDYSIALDKK((2-[2-(2-Amino-ethoxy)-ethoxy]-acetyl)$_2$-(γ-Glu)-CO-(CH$_2$)$_{18}$-CO$_2$H)HQ-(Aib)-EFVNYLLATGPSSGAPPPS-NH$_2$ | 4894.56 | 4894.2 |
| 36 | 40 | Y-(Aib)-EGT-αMeF(2F)-ISDYSIALDKK((2-[2-(2-Amino-ethoxy)-ethoxy]-acetyl)$_2$-(γ-Glu)-CO-(CH$_2$)$_{18}$-CO$_2$H)HQ-(Aib)-DFVEYLLETGPSSGAPPPS-NH$_2$ | 5005.59 | 5005.8 |
| 37 | 41 | Y-(Aib)-EGT-αMeF(2F)-ISDYSIALDKK((2-[2-(2-Amino-ethoxy)-ethoxy]-acetyl)$_2$-(γ-Glu)-CO-(CH$_2$)$_{18}$-CO$_2$H)HQ-(Aib)-DFVEYLLEGGPSSGAPPPS-NH$_2$ | 4961.54 | 4961.4 |
| 38 | 42 | Y-(Aib)-EGT-αMeF(2F)-ISDYSIALDKK((2-[2-(2-Amino-ethoxy)-ethoxy]-acetyl)$_2$-(γ-Glu)-CO-(CH$_2$)$_{18}$-CO$_2$H)HQ-(Aib)-DFVE-(4-Pal)-LLETGPSSGAPPPS-NH$_2$ | 4990.58 | 4990.2 |
| 39 | 43 | Y-(Aib)-EGT-αMeF(2F)-ISDYSIALDKK((2-[2-(2-Amino-ethoxy)-ethoxy]-acetyl)$_2$-(γ-Glu)-CO-(CH$_2$)$_{18}$- | 4946.53 | 4946.4 |

-continued

| Example | SEQ ID NO | Compound Name | Calculated (avg) MW | Found (avg) MW |
|---|---|---|---|---|
| | | $CO_2H$)HQ-(Aib)-DFVE-(4-Pal)-LLEGGPSSGAPPPS-$NH_2$ | | |
| 40 | 44 | Y-(Aib)-EGT-αMeF(2F)-ISDYSIALDKK((2-[2-(2-Amino-ethoxy)-ethoxy]-acetyl)$_2$-(γ-Glu)-CO-$(CH_2)_{18}$-$CO_2H$)HQ-(Aib)-DFVEWLLETGPSSGAPPPS-$NH_2$ | 5028.63 | 5028.6 |
| 41 | 45 | Y-(Aib)-EGT-(αMeF)-ISDYSIALDKK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLETGPSSGAPPPS-$NH_2$ | 4972.59 | 4972.5 |
| 42 | 46 | Y-(Aib)-EGT-(αMeF)-ISDYSIALDKK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLEQGPSSGAPPPS-$NH_2$ | 4999.61 | 4999.8 |
| 43 | 47 | Y-(Aib)-EGT-(αMeF)-ISDYSIALDKK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLEAGPSSGAPPPS-$NH_2$ | 4942.56 | 4942.2 |
| 44 | 48 | Y-(Aib)-EGT-(αMeF)-ISDYSIALDKK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLEGGPSSGAPPPS-$NH_2$ | 4928.54 | 4928.1 |
| 45 | 49 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLETGPSSGAPPPS-$NH_2$ | 5014.67 | 5014.65 |
| 46 | 50 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLEQGPSSGAPPPS-$NH_2$ | 5041.69 | 5041.35 |
| 47 | 51 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLEGGPSSGAPPPS-$NH_2$ | 4970.62 | 4970.4 |
| 48 | 52 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLAGGPSSGAPPPS-$NH_2$ | 4912.58 | 4912.8 |
| 49 | 53 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{16}$-$CO_2H$)HQ-(Aib)-DFVE-(4-Pal)-LLAGGPSSGAPPPS-$NH_2$ | 4884.51 | 4884.6 |
| 50 | 54 | Y-(Aib)-EGT-(αMeF)-ISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLAGGPSSGAPPPS-$NH_2$ | 4926.61 | 4926.9 |
| 51 | 55 | Y-(Aib)-EGT-αMeF(2F)-ISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLAGGPSSGAPPP5-$NH_2$ | 4944.6 | 4944.6 |
| 52 | 56 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-EFVE-(4-Pal)-LLAGGPSSGAPPPS-$NH_2$ | 4926.61 | 4926.3 |
| 53 | 57 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVEYLLAGGPSSGAPPPS-$NH_2$ | 4927.59 | 4927.5 |

-continued

| Example | SEQ ID NO | Compound Name | Calculated (avg) MW | Found (avg) MW |
|---|---|---|---|---|
| 54 | 58 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2$H)HQ-(Aib)-DFVEWLLAGGPSSGAPPPS-$NH_2$ | 4950.63 | 4950.6 |
| 55 | 59 | Y-(Aib)-EGT-(Iva)-ISDYSI-(αMeL)-LDKK((2-[2-(2-Amino-ethoxy)-ethoxy]-acetyl)$_2$-(γ-Glu)-CO-$(CH_2)_{18}$-$CO_2$H)HQ-(Aib)-DFVE-(4-Pal)-LLAGGPSSGAPPPS-$NH_2$ | 4864.54 | 4864.8 |
| 56 | 60 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2$H)HQ-(Aib)-D-(αMeF)-VE-(4-Pal)-LLAGGPSSGAPPPS-$NH_2$ | 4926.61 | 4926.6 |
| 57 | 61 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2$H)HQ-(Aib)-EFVE-(4-Pal)-LLAQGPSSGAPPPS-$NH_2$ | 4997.69 | 4997.5 |
| 58 | 62 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2$H)HQ-(Aib)-EFVE-(4-Pal)-LLATGPSSGAPPPS-$NH_2$ | 4970.66 | 4970.4 |
| 59 | 63 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2$H)HQ-(Aib)-EFVE-(4-Pal)-LLAAGPSSGAPPPS-$NH_2$ | 4940.63 | 4940.4 |
| 60 | 64 | Y-(Aib)-EGT-(αMeF)-ISDYSI-(αMeL)-LDKK((2-[2-(2-Amino-ethoxy)-ethoxy]-acetyl)$_2$-(γ-Glu)-CO-$(CH_2)_{18}$-$CO_2$H)HQ-(Aib)-EFVE-(4-Pal)-LLAQGPSSGAPPPS-$NH_2$ | 5011.71 | 5011.5 |
| 61 | 65 | Y-(Aib)-EGT-(αMeF)-ISDYSI-(αMeL)-LDKK((2-[2-(2-Amino-ethoxy)-ethoxy]-acetyl)$_2$-(γ-Glu)-CO-$(CH_2)_{18}$-$CO_2$H)HQ-(Aib)-EFVE-(4-Pal)-LLATGPSSGAPPP5-$NH_2$ | 4984.69 | 4984.8 |
| 62 | 66 | Y-(Aib)-EGT-(αMeF)-ISDYSI-(αMeL)-LDKK((2-[2-(2-Amino-ethoxy)-ethoxy]-acetyl)$_2$-(γ-Glu)-CO-$(CH_2)_{18}$-$CO_2$H)HQ-(Aib)-EFVE-(4-Pal)-LLAAGPSSGAPPPS-$NH_2$ | 4954.66 | 4954.2 |
| 63 | 67 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2$H)HQ-(Aib)-EFVEYLLEQGPSSGAPPPS-$NH_2$ | 5070.73 | 5070.9 |
| 64 | 68 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2$H)HQ-(Aib)-EFVEYLLETGPSSGAPPPS-$NH_2$ | 5043.71 | 5043.9 |
| 65 | 69 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2$H)HQ-(Aib)-EFVEYLLEAGPSSGAPPPS-$NH_2$ | 5013.68 | 5013.9 |
| 66 | 70 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2$H)HQ-(Aib)-DFVEYLLETGPSSGAPPPS-$NH_2$ | 5029.68 | 5029.2 |
| 67 | 71 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2$H)HQ-(Aib)-DFVEYLLEQGPSSGAPPPS-$NH_2$ | 5056.71 | 5056.8 |

-continued

| Example | SEQ ID NO | Compound Name | Calculated (avg) MW | Found (avg) MW |
|---|---|---|---|---|
| 68 | 72 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVEYLLEAGPSSGAPPPS-$NH_2$ | 4999.65 | 4999.2 |
| 69 | 73 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVEYLLEGGPSSGAPPPS-$NH_2$ | 4985.63 | 4985.7 |
| 70 | 74 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLATGPSSGAPPPS-$NH_2$ | 4956.63 | 4956.3 |
| 71 | 75 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVEWLLETGPSSGAPPPS-$NH_2$ | 5052.72 | 5052.6 |
| 72 | 76 | Y-(Aib)-EGTLISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-EFVEYLLETGPSSGAPPPS-$NH_2$ | 5009.69 | 5009.7 |
| 73 | 77 | Y-(Aib)-EGTLISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-EFVEYLLEGGPSSGAPPPS-$NH_2$ | 4965.64 | 4965.3 |
| 74 | 78 | Y-(Aib)-EGT-(Iva)-ISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLEGGPSSGAPPPS-$NH_2$ | 4922.57 | 4922.4 |
| 75 | 79 | Y-(Aib)-EGT-(Iva)-ISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLETGPSSGAPPPS-$NH_2$ | 4966.63 | 4966.8 |
| 76 | 80 | Y-(Aib)-EGT-(Iva)-ISDYSI-(αMeL)-LD-(Orn)-K((2-[2-(2-Amino-ethoxy)-ethoxy]-acetyl)2-(γ-Glu)-CO-$(CH_2)_{18}$-$CO_2H$)HQ-(Aib)-DFVE-(4-Pal)-LLEGGPSSGAPPPS-$NH_2$ | 4908.55 | 4908.6 |
| 77 | 81 | Y-(Aib)-EGT-(Iva)-ISDYSI-(αMeL)-LD-(Orn)-K((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLETGPSSGAPPPS-$NH_2$ | 4952.6 | 4952.4 |
| 78 | 82 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLAAGPSSGAPPPS-$NH_2$ | 4926.61 | 4926.3 |
| 79 | 83 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLAQGPSSGAPPPS-$NH_2$ | 4983.66 | 4983.3 |
| 80 | 84 | Y-(Aib)-EGTFISDYSI-(αMeL)-LD-(Orn)-K((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLETGPSSGAPPPS-$NH_2$ | 5000.64 | 5000.4 |

-continued

| Example | SEQ ID NO | Compound Name | Calculated (avg) MW | Found (avg) MW |
|---|---|---|---|---|
| 81 | 85 | Y-(Aib)-EGTFISDYSI-(αMeL)-LD-(Orn)-K((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLEQGPSSGAPPPS-$NH_2$ | 5027.67 | 5027.7 |
| 82 | 86 | Y-(Aib)-EGTFISDYSI-(αMeL)-LD-(Orn)-K((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLEGGPSSGAPPPS-$NH_2$ | 4956.59 | 4956.45 |
| 83 | 87 | Y-(Aib)-EGTFISDYSI-(αMeL)-LDEK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLATGPSSGAPPPS-$NH_2$ | 4957.57 | 4957.8 |
| 84 | 88 | Y-(Aib)-EGTFISDYSI-(αMeL)-LDEK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLAQGPSSGAPPPS-$NH_2$ | 4984.6 | 4984.2 |
| 85 | 89 | Y-(Aib)-EGTFISDYSI-(αMeL)-LDEK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLAAGPSSGAPPPS-$NH_2$ | 4927.55 | 4927.2 |
| 86 | 90 | Y-(Aib)-EGTFISDYSI-(αMeL)-LDEK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLAGGPSSGAPPPS-$NH_2$ | 4913.52 | 4913.1 |
| 87 | 91 | Y-(Aib)-EGTFISDYSI-(αMeL)-LD-(Orn)-K((2-[2-(2-Amino-ethoxy)-ethoxy]-acetyl)2-(γ-Glu)-CO-$(CH_2)_{16}$-$CO_2H$)HQ-(Aib)-DFVE-(4-Pal)-LLEAGPSSGAPPPS-$NH_2$ | 4942.56 | 4942.8 |
| 88 | 92 | Y-(Aib)-EGT-(Iva)-ISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLEAGPSSGAPPPS-$NH_2$ | 4936.6 | 4936.2 |
| 89 | 93 | Y-(Aib)-EGTLISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVE-(4-Pal)-LLEAGPSSGAPPPS-$NH_2$ | 4950.63 | 4950.6 |
| 90 | 94 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVE-(αMeY)-LLEAGPSSGAPPPS-$NH_2$ | 5013.64 | 5013.6 |
| 91 | 95 | Y-(Aib)-EGTFISDYSI-(αMeL)-LDKK((2-[2-(2-Amino-ethoxy)-ethoxy]-acetyl)$_2$-(γ-Glu)-CO-$(CH_2)_{18}$-$CO_2H$)HQ-(Aib)-DFVE-(αMeY)-LLEGGPSSGAPPPS-$NH_2$ | 4999.61 | 4999.5 |
| 92 | 96 | Y-(Aib)-EGTFISDYSI-(αMeL)-LDKIHQ-(Aib)-DFVEYK((2-[2-(2-Amino-ethoxy)-ethoxy]-acetyl)$_2$-(γ-Glu)-CO-$(CH_2)_{18}$-$CO_2H$)LEQGPSSGAPPPS-$NH_2$ | 5056.71 | 5057.1 |
| 93 | 97 | Y-(D-Ala)-EGTFISDYSILLDKIAQ-(Aib)-DF VNWK((2-[2-(2-Amino-ethoxy)-ethoxy]-acetyl)$_2$-(γ-Glu)-CO-$(CH_2)_{16}$-$CO_2H$)LAQGPSSGAPPPS-$NH_2$ | 4884.53 | 4884.3 |
| 94 | 98 | Y-(Aib)-EGT-αMeF(2F)-ISDYSIALDKIHQ-(Aib)-EFVNYK((2-[2-(2-Amino-ethoxy)-ethoxy]-acetyl)$_2$-(γ-Glu)-CO-$(CH_2)_{16}$-$CO_2H$)LAGGPSSGAPPPS-$NH_2$ | 4874.46 | 4874.4 |

-continued

| Example | SEQ ID NO | Compound Name | Calculated (avg) MW | Found (avg) MW |
|---|---|---|---|---|
| 95 | 99 | Y-(Aib)-EGT-αMeF(2F)-ISDYSIALDKIHQ-(Aib)-EFVNYK((2-[2-(2-Amino-ethoxy)-ethoxy]-acetyl)$_2$-(γ-Glu)-CO-$(CH_2)_{18}$-$CO_2H$)LEGGPSSGAPPPS-$NH_2$ | 4960.55 | 4960.8 |
| 96 | 100 | Y-(Aib)-EGTFISDYSIALDKIHQ-(Aib)-EFVNYK((2-[2-(2-Amino-ethoxy)-ethoxy]-acetyl)$_2$-(γ-Glu)-CO-$(CH_2)_{18}$-$CO_2H$)LAGGPSSGAPPPS-$NH_2$ | 4870.5 | 4870.2 |
| 97 | 101 | Y-(Aib)-EGT-(αMeF)-ISDYSIALDKIHQ-(Aib)-EFVNYK((2-[2-(2-Amino-ethoxy)-ethoxy]-acetyl)$_2$-(γ-Glu)-CO-$(CH_2)_{18}$-$CO_2H$)LAGGPSSGAPPPS-$NH_2$ | 4884.53 | 4884.6 |
| 98 | 102 | Y-(Aib)-EGT-αMeF(2F)-ISDYSIALDKIHQ-(Aib)-EFVNYK((2-[2-(2-Amino-ethoxy)-ethoxy]-acetyl)$_2$-(γ-Glu)-CO-$(CH_2)_{18}$-$CO_2H$)LAGGPSSGAPPPS-$NH_2$ | 4902.52 | 4902.15 |
| 99 | 103 | Y-(Aib)-EGT-αMeF(2F)-ISDYSIALDKIHQ-(Aib)-DFVEYK((2-[2-(2-Amino-ethoxy)-ethoxy]-acetyl)$_2$(γ-Glu)-CO-$(CH_2)_{18}$-$CO_2H$)LEGGPSSGAPPPS-$NH_2$ | 4961.54 | 4961.4 |
| 100 | 104 | Y-(Aib)-EGTFISDYSI-(αMeL)-LDKIHQ-(Aib)-EFVE-(4-Pal)-K((2-[2-(2-Amino-ethoxy)-ethoxy]-acetyl)$_2$-(γ-Glu)-CO-$(CH_2)_{18}$-$CO_2H$)LEGGPSSGAPPPS-$NH_2$ | 4984.64 | 4984.2 |
| 101 | 105 | Y-(Aib)-EGTFISDYSI-(αMeL)-LD-(Orn)-IHQ-(Aib)-DFV-(D-Glu)-YK((2-[2-(2-Amino-ethoxy)-ethoxy]-acetyl)$_2$-(γ-Glu)-CO-$(CH_2)_{18}$-$CO_2H$)LEGGPSSGAPPPS-$NH_2$ | 4971.6 | 4971.75 |
| 102 | 106 | Y-(Aib)-EGTFISDYSI-(αMeL)-LD-(Orn)-IHQ-(Aib )-EFV-(D-Glu)-YK((2-[2-(2-Amino-ethoxy)-ethoxy]-acetyl)$_2$-(γ-Glu)-CO-$(CH_2)_{18}$-$CO_2H$)LEGGPSSGAPPPS-$NH_2$ | 4985.63 | 4985.1 |
| 103 | 107 | Y-(Aib)-EGTFISDYSI-(αMeL)-LD-(Orn)-IHQ-(Aib)-DFVEYK((2-[2-(2-Amino-ethoxy)-ethoxy]-acetyl)$_2$-(γ-Glu)-CO-$(CH_2)_{16}$-$CO_2H$)LEGGPSSGAPPPS-$NH_2$ | 4943.55 | 4943.4 |
| 104 | 108 | Y-(Aib)-EGTFISDYSI-(αMeL)-LD-(Orn)-IHQ-(Aib)-EFVEYK((2-[2-(2-Amino-ethoxy)-ethoxy]-acetyl)$_2$-(γ-Glu)-CO-$(CH_2)_{18}$-$CO_2H$)LEAGPSSGAPPPS-$NH_2$ | 4999.65 | 4999.2 |
| 105 | 109 | Y-(Aib)-EGTFISDYSI-(αMeL)-LD-(Orn)-IHQ-(Aib)-EFVEYK((2-[2-(2-Amino-ethoxy)-ethoxy]-acetyl)$_2$-(γ-Glu)-CO-$(CH_2)_{18}$-$CO_2H$)LETGPSSGAPPPS-$NH_2$ | 5029.68 | 5029.2 |
| 106 | 110 | Y-(Aib)-EGTFISDYSI-(αMeL)-LD-(Orn)-IHQ-(Aib)-EFVEYK((2-[2-(2-Amino-ethoxy)-ethoxy]-acetyl)$_2$-(γ-Glu)-CO-$(CH_2)_{18}$-$CO_2H$)LEQGPSSGAPPPS-$NH_2$ | 5056.71 | 5056.8 |
| 107 | 111 | Y-(Aib)-EGTFISDYSI-(αMeL)-LD-(Orn)-IHQ-(Aib)-EFVEYK((2-[2-(2-Amino-ethoxy)-ethoxy]-acetyl)$_2$-(γ-Glu)-CO-$(CH_2)_{18}$-$CO_2H$)LEGGPSSGAPPPS-$NH_2$ | 4985.63 | 4985.4 |

-continued

| Example | SEQ ID NO | Compound Name | Calculated (avg) MW | Found (avg) MW |
|---|---|---|---|---|
| 108 | 112 | Y-(Aib)-EGTFISDYSI-(αMeL)-LD-(Orn)-IHQ-(Aib)-DFVE-(4-Pal)-K((2-[2-(2-Amino-ethoxy)-ethoxy]-acetyl)$_2$-(γ-Glu)-CO-$(CH_2)_{18}$-$CO_2$H)LEGGPSSGAPPPS-$NH_2$ | 4956.59 | 4956.3 |
| 109 | 113 | Y-(Aib)-EGTFISDYSI-(αMeL)-LDKIHQ-(Aib)-DFVE-(4-Pal)-K((2-[2-(2-Amino-ethoxy)-ethoxy]-acetyl)$_2$-(γ-Glu)-CO-$(CH_2)_{18}$-$CO_2$H)LEGGPSSGAPPPS-$NH_2$ | 4970.62 | 4970.4 |
| 110 | 114 | Y-(Aib)-EGTFISDYSI-(αMeL)-LDKIHQ-(Aib)-DFVE-(4-Pal)-K((2-[2-(2-Amino-ethoxy)-ethoxy]-acetyl)$_2$-(γ-Glu)-CO-$(CH_2)_{16}$-$CO_2$H)LEGGPSSGAPPPS-$NH_2$ | 4942.56 | 4942.2 |
| 111 | 115 | Y-(Aib)-EGTFISDYSI-(αMeL)-LD-(Orn)-IHQ-(Aib)-DFVE-(4-Pal)-K((2-[2-(2-Amino-ethoxy)-ethoxy]-acetyl)$_2$-(γ-Glu)-CO-$(CH_2)_{16}$-$CO_2$H)LEGGPSSGAPPPS-$NH_2$ | 4928.54 | 4928.4 |
| 112 | 116 | Y-(Aib)-EGT-αMeF(2F)-ISDYSIALDKIHQ-(Aib)-DFVE-(4-Pal)-K((2-[2-(2-Amino-ethoxy)-ethoxy]-acetyl)$_2$-(γ-Glu)-CO-$(CH_2)_{18}$-$CO_2$H)LEGGPSSGAPPPS-$NH_2$ | 4946.53 | 4946.4 |
| 113 | 117 | Y-(Aib)-EGT-αMeF(2F)-ISDYSIALDKIHQ-(Aib)-DFVE-(4-Pal)-K((2-[2-(2-Amino-ethoxy)-ethoxy]-acetyl)$_2$-(γ-Glu)-CO-$(CH_2)_{18}$-COH) LEAGPSSGAPPPS-$NH_2$ | 4960.55 | 4960.8 |
| 114 | 118 | Y-(Aib)-EGT-αMeF(2F)-ISDYSIALDKIHQ-(Aib)-DFVE-(4-Pal)-K((2-[2-(2-Amino-ethoxy)-ethoxy]-acetyl)$_2$-(γ-Glu)-CO-$(CH_2)_{18}$-$CO_2$H) LEQGPSSGAPPPS-$NH_2$ | 5017.6 | 5017.2 |
| 115 | 119 | Y-(Aib)-EGTFISDYSI-(αMeL)-LDKIRQ-(Aib)-DFVEYK((2-[2-(2-Amino-ethoxy)-ethoxy]-acetyl)$_2$-(γ-Glu)-CO-$(CH_2)_{18}$-$CO_2$H)LEGGPSSGAPPPS-$NH_2$ | 5004.63 | 5004.6 |
| 116 | 120 | Y-(Aib)-EGTFISDYSI-(αMeL)-LD-(Orn)-IRQ-(Aib)-DFVEYK((2-[2-(2-Amino-ethoxy)-ethoxy]-acetyl)$_2$-(γ-Glu)-CO-$(CH_2)_{18}$-$CO_2$H)LEGGPSSGAPPPS-$NH_2$ | 4990.61 | 4990.2 |
| 117 | 121 | Y-(Aib)-EGTFISDYSI-(αMeL)-LDKIHQ-(Aib)-DFVEYK((2-[2-(2-Amino-ethoxy)-ethoxy]-acetyl)$_2$-(γ-Glu)-CO-$(CH_2)_{18}$-$CO_2$H)LEAGPSSGAPPPS-$NH_2$ | 4999.65 | 4999.8 |
| 118 | 122 | Y-(Aib)-EGTFISDYSI-(αMeL)-LDKIRQ-(Aib)-DFVEYK((2-[2-(2-Amino-ethoxy)-ethoxy]-acetyl)$_2$-(γ-Glu)-CO-$(CH_2)$18-$CO_2$H)LEAGPSSGAPPPS-$NH_2$ | 5018.66 | 5018.4 |
| 119 | 123 | Y-(Aib)-EGT-αMeF(2F)-ISDYSILLDKIHQ-(Aib)-DFVE-(4-Pal)-K((2-[2-(2-Amino-ethoxy)-ethoxy]-acetyl)$_2$-(γ-Glu)-CO-$(CH_2)_{18}$-$CO_2$H)LEGGPSSGAPPPS-$NH_2$ | 4988.57 | 4988.4 |
| 120 | 124 | Y-(Aib)-EGT-αMeF(2F)-ISDYSILLDKIHQ-(Aib)-DFVE-(4-Pal)-K((2-[2-(2-Amino-ethoxy)-ethoxy]-acetyl)$_2$-(γ-Glu)-CO-$(CH_2)_{18}$-$CO_2$H)LEAGPSSGAPPPS-$NH_2$ | 5002.59 | 5002.5 |

-continued

| Example | SEQ ID NO | Compound Name | Calculated (avg) MW | Found (avg) MW |
|---|---|---|---|---|
| 121 | 125 | Y-(Aib)-EGT-αMeF(2F)-ISDYSILLDKIHQ-(Aib)-DFVE-(4-Pal)-K((2-[2-(2-Amino-ethoxy)-ethoxy]-acetyl)$_2$-(γ-Glu)-CO-$(CH_2)_{18}$-$CO_2$H)LEQGPSSGAPPPS-$NH_2$ | 5059.64 | 5059.8 |
| 122 | 126 | Y-(Aib)-EGTFISDYSI-(αMeL)-LD-(Orn)-IHQ-(Aib)-EFVE-(4-Pal)-K((2-[2-(2-Amino-ethoxy)-ethoxy]-acetyl)$_2$-(γ-Glu)-CO-$(CH_2)_{18}$-$CO_2$H)LEAGPSSGAPPPS-$NH_2$ | 4984.64 | 4984.80 |

Binding Assays

Glucagon (referred to as Gcg or hGcg) is a Reference Standard prepared at Eli Lilly and Company. GLP-1(7-36)-$NH_2$ (referred to as GLP-1 or hGLP-1) is obtained from CPC Scientific (Sunnyvale, CA, 97.2% purity, 100 μM aliquots in 100% DMSO). GIP(1-42)-$NH_2$ (referred to as GIP) is prepared at Lilly Research Laboratories using peptide synthesis and HPLC chromatography as described above (>80% purity, 100 μM aliquots in 100% DMSO). [$^{125}$I]-radiolabeled Gcg, GLP-1, or GIP is prepared using [$^{125}$I]-lactoperoxidase and obtained from Perkin Elmer (Boston, MA).

Stably transfected cell lines are prepared by subcloning receptor cDNA into a pcDNA3 expression plasmid and transfected into human embryonic kidney (HEK) 293 (hGcgR and hGLP-1R) or Chinese Hamster Ovary (CHO) (hGIPR) cells followed by selection with Geneticin (hGLP-1R and hGIPR) or hygromycin B (hGcgR).

Two methods are used for the preparation of crude cell membranes.

Method 1: Frozen cell pellets are lysed on ice in hypotonic buffer containing 50 mM Tris HCl, pH 7.5, and Roche Complete™ Protease Inhibitors with EDTA. The cell suspension is disrupted using a glass Potter-Elvehjem homogenizer fitted with a Teflon® pestle for 25 strokes. The homogenate is centrifuged at 4° C. at 1100× g for 10 minutes. The supernatant is collected and stored on ice while the pellets are resuspended in homogenization buffer and rehomogenized as described above. The homogenate is centrifuged at 1100× g for 10 minutes. The second supernatant is combined with the first supernatant and centrifuged at 35000× g for 1 hour at 4° C. The resulting membrane pellet is resuspended in homogenization buffer containing protease inhibitors at approximately 1 to 3 mg/mL, quick frozen in liquid nitrogen and stored as aliquots in a −80° C. freezer until use.

Method 2: Frozen cell pellets are lysed on ice in hypotonic buffer containing 50 mM Tris HCl, pH 7.5, 1 mM $MgCl_2$, Roche Complete™ EDTA-free Protease Inhibitors and 25 units/mL DNAse I (Invitrogen). The cell suspension is disrupted using a glass Potter-Elvehjem homogenizer fitted with a Teflon® pestle for 20 to 25 strokes. The homogenate is centrifuged at 4° C. at 1800× g for 15 minutes. The supernatant is collected and stored on ice while the pellets are resuspended in homogenization buffer (without DNAse I) and rehomogenized as described above. The homogenate is centrifuged at 1800× g for 15 minutes. The second supernatant is combined with the first supernatant and centrifuged an additional time at 1800× g for 15 minutes. The overall supernatant is then centrifuged at 25000× g for 30 minutes at 4° C. The resulting membrane pellet is resuspended in homogenization buffer (without DNAse I) containing protease inhibitors at approximately 1 to 3 mg/mL and stored as aliquots in a −80° C. freezer until use.

Binding Determination Methods

The equilibrium binding dissociation constants ($K_d$) for the various receptor/radioligand interactions are determined from homologous competition binding analysis instead of saturation binding due to high propanol content in the [$^{125}$I] stock material. The $K_d$ values determined for the receptor preparations were as follows: hGcgR (3.9 nM), hGLP-1R (1.2 nM) and hGIPR (0.14 nM).

[$^{125}$I]-Glucagon Binding

The human Gcg receptor binding assays are performed using a Scintillation Proximity Assay (SPA) format with wheat germ agglutinin (WGA) beads (Perkin Elmer). The binding buffer contains 25 mM 4-(2-hydroxyethyl)-1-piperazineethanesulfonic acid (HEPES), pH 7.4, 2.5 mM $CaCl_2$), 1 mM $MgCl_2$, 0.1% (w/v) bacitracin (Research Products), 0.003% (w/v) Polyoxyethylenesorbitan monolaurate (TWEEN®-20), and Roche Complete™ Protease Inhibitors without EDTA. Peptides and Gcg are thawed and 3-fold serially diluted in 100% DMSO (10 point concentration response curves). Next, 5 μL serially diluted compound or DMSO is transferred into Corning® 3632 clear bottom assay plates containing 45 μL assay binding buffer or unlabeled Gcg control (non-specific binding or NSB, at 1 μM final). Then, 50 μL [$^{125}$I]-Gcg (0.15 nM final), 50 μL human GcgR membranes (1.5 μg/well) and 50 μL of WGA SPA beads (80 to 150 μg/well) are added with a Biotek Multiflo dispenser. Plates are sealed and mixed on a plate shaker (setting 6) for 1 minute and read with a PerkinElmer Trilux MicroBeta® scintillation counter after 12 hours of incubation/settling time at room temperature. Final assay concentration ranges for peptides tested in response curves is typically 1150 nM to 0.058 nM and for the control Gcg from 1000 nM to 0.05 nM.

[$^{125}$I]-GLP-1 Binding

The human GLP-1 receptor binding assay is performed using an SPA format with WGA beads. The binding buffer contains 25 mM HEPES, pH 7.4, 2.5 mM $CaCl_2$), 1 mM $MgCl_2$, 0.1% (w/v) bacitracin, 0.003% (w/v) TWEEN®-20, and Roche Complete™ Protease Inhibitors without EDTA. Peptides and GLP-1 are thawed and 3-fold serially diluted in 100% DMSO (10 point concentration response curves). Next, 5 μL serially diluted compound or DMSO is transferred into Corning® 3632 clear bottom assay plates containing 45 μL assay binding buffer or unlabeled GLP-1 control (non-specific binding or NSB, at 0.25 μM final).

Then, 50 μL $[^{125}I]$-GLP-1 (0.15 nM final), 50 μL human GLP-1R membranes (0.5 μg/well and 50 μL of WGA SPA beads (100 to 150 μg/well) are added with a Biotek Multiflo dispenser. Plates are sealed and mixed on a plate shaker (setting 6) for 1 minute and read with a PerkinElmer Trilux MicroBeta® scintillation counter after 5 to 12 hours of incubation/settling time at room temperature. Final assay concentration ranges for peptides tested in response curves are typically 1150 nM to 0.058 nM and for the control GLP-1, 250 nM to 0.013 nM.

$[^{125}I]$-GIP Binding

The human GIP receptor binding assay is performed using an SPA format with WGA beads. The binding buffer contains 25 mM HEPES, pH 7.4, 2.5 mM $CaCl_2$), 1 mM $MgCl_2$, 0.1% (w/v) bacitracin, 0.003% (w/v) TWEEN®-20, and Roche Complete™ Protease Inhibitors without EDTA. Peptides and GIP are thawed and 3-fold serially diluted in 100% DMSO (10 point concentration response curves). Next, 5 μL serially diluted compound or DMSO is transferred into Corning® 3632 clear bottom assay plates containing 45 μL assay binding buffer or unlabeled GIP control (non-specific binding or NSB, at 0.25 μM final). Then, 50 μL $[^{125}I]$-GIP (0.075-0.15 nM final), 50 μL human GIPR membranes (3 μg/well) and 50 μL of WGA SPA beads (100 to 150 μg/well) are added with a Biotek Multiflo dispenser. Plates are sealed and mixed on a plate shaker (setting 6) for 1 minute and read with a PerkinElmer Trilux MicroBeta® scintillation counter after 2.5 to 12 hours of incubation/settling time at room temperature. Final assay concentration ranges for peptides tested in response curves is typically 1150 to 0.058 nM or 115 nM to 0.0058 nM and for the control GIP, 250 nM to 0.013 nM.

Binding Assay Data Analysis

Raw CPM data for concentration curves of peptides, Gcg, GLP-1, or GIP are converted to percent inhibition by subtracting nonspecific binding (binding in the presence of excess unlabeled Geg, GLP-1, or GIP, respectively) from the individual CPM values and dividing by the total binding signal, also corrected by subtracting nonspecific binding. Data are analyzed using four-parameter (curve maximum, curve minimum, $IC_{50}$, Hill slope) nonlinear regression routines (Genedata Screener, version 12.0.4, Genedata AG, Basal, Switzerland). The affinity constant ($K_i$) is calculated from the absolute $IC_{50}$ value based upon the equation $K_i=IC_{50}/(1+D/K_d)$ where D is the concentration of radioligand used in the experiment, $IC_{50}$ is the concentration causing 50% inhibition of binding and $K_d$ is the equilibrium binding dissociation constant of the radioligand (described above). Values for $K_i$ are reported as the geometric mean, with error expressed as the standard error of the mean (SEM) and n is equal to the number of independent replicates (determined in assays performed on different days). Geometric Means are calculated as follows:

Geometric Mean=10(Arithmetic Mean of Log Ki Values))

n=y/x means that only a subset of replicates (v) out of the total number of replicates (x) is used to express the mean. SEM is only calculated when y=2 or greater. Means are expressed as geometric means with the standard error of the mean (SEM) and the number of replicates (n) indicated in parentheses.

TABLE 1

In vitro Binding Affinity ($K_i$) of indicated Examples and comparator molecules for human GcgR, GIPR, and GLP-1R in the presence of 0.1% bacitracin.

| Example or Comparator | hGcgR Ki (nM) (SEM, n) | hGIPR Ki (nM) (SEM, n) | hGLP1R Ki (nM) (SEM, n) |
|---|---|---|---|
| hGIP-$NH_2$ | 1150 (18.3, n = 4) | 0.125 (0.00511, n = 319) | 1100 (143, n = 4) |
| hGlucagon | 3.05 (0.120, n = 457) | >2420 (n = 3) | >4940 (n = 5) |
| hGLP-1 (7-36) $NH_2$ | >4590 (n = 5) | >2300 (n = 3) | 0.785 (0.0252, n = 489) |
| 1 | 228 (46.6, n = 5) | 0.0667 (0.0566, n = 5) | 57.8 (16.7, n = 5) |
| 2 | 379 (218, n = 3) | 0.0373 (0.000430, n = 3) | 77.9 (20.2, n = 3) |
| 3 | 338 (220, n = 8) | 0.0525 (0.0215, n = 8) | 381 (226, n = 8) |
| 4 | 431 (253, n = 6) | 0.0620 (0.0259, n = 6) | 423 (235, n = 6) |
| 5 | 619 (140, n = 9) | 0.0771 (0.0342, n = 9) | >913 (n = 9) |
| 6 | 453 (125, n = 7) | 0.104 (0.0866, n = 7) | 571 (368, n = 7) |
| 7 | >961 (n = 5) | 0.193 (0.157, n = 5) | >913 (n = 5) |
| 8 | 101 | 0.027 | 38.1 |
| 9 | >230 | 0.110 | 168 |
| 10 | >230 | 0.159 | 60.7 |
| 11 | 163 | 0.0584 | 85.9 |
| 12 | 134 | 0.0876 | 46.8 |
| 13 | >230 | 0.237 | >213 |
| 14 | >230 | 0.460 | >213 |
| 15 | >254 | 0.471 | >236 |
| 16 | 549 | 0.0438 | 99.2 |
| 17 | 274 | 0.0571 | 106 |
| 18 | 463 | 0.0331 | 158 |
| 19 | 335 | 0.0469 | 15.2 |
| 20 | 216 | 0.0477 | 79.8 |
| 21 | >1530 | 1.46 | 801 |
| 22 | >1380 | 0.219 | 388 |
| 23 | 323 | 0.0341 | 251 |
| 24 | >960 | 0.254 | 729 |
| 25 | 101 | 0.0417 | 15.8 |
| 26 | 74.1 | 0.045 | 16.5 |
| 27 | 401 | 0.0354 | 23.2 |
| 28 | 86.8 | 0.0732 | 6.46 |
| 29 | 133 | 0.0569 | 22.7 |
| 30 | 407 | 0.037 | 26.5 |
| 31 | >959 | 0.0473 | 266 |
| 32 | >959 | 0.0343 | 85.2 |
| 33 | 63.5 | 0.0369 | 31.2 |
| 34 | 143 | 0.034 | 201 |
| 35 | >960 | 0.0351 | 177 |
| 36 | 201 | 0.0683 | 393 |
| 37 | 51.4 | 0.026 | 83.9 |
| 38 | 182 (59.8, n = 2) | 0.0588 (0.0112, n = 2) | 776 (134, n = 2) |
| 39 | 76.0 (19.3, n = 2) | 0.0444 (0.00439, n = 2) | 235 (8.34, n = 2) |
| 40 | 50.9 | 0.0594 | 302 |
| 41 | 758 | 0.143 | >906 |
| 42 | 99.1 | 0.0392 | 563 |
| 43 | 285 (121, n = 2) | 0.0366 | 605 |
| 44 | 50 | 0.059 | 209 |
| 45 | 660 (257, n = 3) | 0.0663 (0.0241, n = 3) | >909 (n = 3) |
| 46 | 435 (89.6, n = 3) | 0.0319 (0.00724, n = 3) | 744 (58.2, n = 3) |
| 47 | 175 (69.7, n = 3) | 0.0452 (0.0127, n = 3) | 320 (77.8, n = 3) |
| 48 | 267 | 0.0498 | 211 |
| 49 | >960 | 0.0512 | 596 |
| 50 | 23.4 | 0.0501 | 34.9 |
| 51 | 26.7 | 0.0386 | 54.1 |
| 52 | 114 | 0.0372 | 128 |
| 53 | 152 | 0.0184 | 62.9 |

TABLE 1-continued

In vitro Binding Affinity ($K_i$) of indicated Examples and comparator molecules for human GcgR, GIPR, and GLP-1R in the presence of 0.1% bacitracin.

| Example or Comparator | hGcgR Ki (nM) (SEM, n) | hGIPR Ki (nM) (SEM, n) | hGLP1R Ki (nM) (SEM, n) |
|---|---|---|---|
| 54 | 386 | 0.0326 | 49.9 |
| 55 | >960 | 0.0331 | 262 |
| 56 | 193 | 0.0487 | 530 |
| 57 | 422 | 0.0154 | 280 |
| 58 | 418 | 0.0324 | 459 |
| | (1.17, n = 2) | (0.00694, n = 2) | (68.3, n = 2) |
| 59 | 230 | 0.0148 | 109 |
| 60 | 26.2 | 0.0390 | 51.4 |
| 61 | 80.4 | 0.0665 | 135 |
| 62 | 31.3 | 0.0414 | 47.6 |
| 63 | 185 | 0.0248 | 327 |
| 64 | 196 | 0.022 | 477 |
| 65 | 279 | 0.0316 | 305 |
| 66 | 279 | 0.0866 | 326 |
| 68 | 290 | 0.0948 | 421 |
| 69 | 114 | 0.0406 | 144 |
| 70 | 857 | 0.0421 | 570 |
| 71 | 102 | 0.0422 | 347 |
| 72 | 837 | 0.0594 | 437 |
| 73 | 292 | 0.036 | 117 |
| 74 | 511 | 0.0287 | 395 |
| 75 | >958 | 0.0626 | >902 |
| 76 | 358 | 0.0293 | 263 |
| 77 | >958 | 0.0841 | >905 |
| | (n = 2) | (0.0207, n = 2) | (n = 2) |
| 78 | 505 | 0.0236 | 394 |
| 79 | 888 | 0.0229 | 486 |
| 80 | >958 | 0.0828 | >906 |
| | (n = 2) | (0.0284, n = 2) | (n = 2) |
| 81 | 699 | 0.0374 | 714 |
| | (35.4, n = 2) | (0.0106, n = 2) | (39.8, n = 2) |
| 82 | 305 | 0.0617 | 388 |
| | (112, n = 2) | (0.00946, n = 2) | (140, n = 2) |
| 83 | >958 | 0.116 | 452 |
| 84 | >958 | 0.0584 | 325 |
| 85 | 800 | 0.0529 | 220 |
| 86 | 462 | 0.0533 | 108 |
| 87 | 576 | 0.0538 | 849 |
| 88 | 788 | 0.0830 | 261 |
| 89 | 611 | 0.0720 | 294 |
| | (n = 3) | (0.0169, n = 4) | (72.9, n = 4) |
| 90 | 112 | 0.129 | 102 |
| 91 | 54.4 | 0.122 | 37.4 |
| 92 | >958 | 0.0331 | >902 |
| 93 | >959 | 0.0430 | >909 |
| 94 | 114 | 0.0310 | >909 |
| 95 | 85.0 | 0.0255 | 832 |
| 96 | >960 | 0.232 | >908 |
| 97 | 77.5 | 0.0249 | 570 |
| 98 | 38.4 | 0.0195 | 311 |
| 99 | 174 | 0.0341 | >901 |
| 100 | 572 | 0.0674 | >913 |
| | (182, n = 4) | (0.0265, n = 3) | (n = 3) |
| 101 | >961 | 0.139 | >913 |
| | (n = 2) | (0.0585, n = 2) | (n = 2) |
| 102 | >961 | 0.164 | >913 |
| | (n = 3) | (0.113, n = 3) | (n = 3) |
| 103 | >960 | 0.0405 | >913 |
| 104 | >960 | 0.134 | >910 |
| 105 | >960 | 0.174 | >910 |
| 106 | 304 | 0.0918 | >910 |
| 107 | 347 | 0.0722 | >911 |
| 108 | >960 | 0.134 | >910 |
| 109 | >960 | 0.117 | >908 |
| 110 | >960 | 0.339 | >908 |
| 111 | >960 | 0.0871 | >908 |
| 112 | 257 | 0.0742 | >908 |
| 113 | 821 | 0.108 | >921 |
| | (3.12, n = 4) | (0.0287, n = 5) | (n = 5) |
| 114 | >971 | 0.121 | >921 |
| | (n = 3) | (0.0496, n = 4) | (n = 4) |
| 115 | 373 | 0.0997 | >912 |
| | (n = 2) | (0.0472, n = 2) | (n = 2) |
| 116 | 178 | 0.166 | >912 |
| | (n = 2) | (0.0753, n = 2) | (n = 2) |
| 117 | 685 | 0.0722 | 591 |
| 118 | NA | 0.0696 | >920 |
| 119 | 68.8 | 0.129 | 723 |
| | (n = 2) | (0.0552, n = 2) | (119, n = 2) |
| 120 | 575 | 0.171 | >912 |
| | (n = 2) | (0.231, n = 2) | (n = 2) |
| 121 | 94.9 | 0.103 | >912 |
| | (n = 2) | (0.0473, n = 2) | (n = 2) |
| 122 | 957 | 0.0311 | >913 |

As demonstrated in Table 1, examples of the present invention are very potent binders of the human GIPR, and have lower affinity for the GLP-1R and GcgR.

CAMP Pharmacological Functional Assay in Presence of 0.1% Casein

A set of cAMP assays are conducted in HEK293 cells expressing the human GLP-1 receptor (GLP-1R), glucose-dependent insulinotropic peptide receptor (GIPR), or glucagon receptor (GcgR). Each receptor over-expressing cell line (20 μl) is treated with the test peptide in DMEM (Gibco Cat #31053) supplemented with 0.1% Casein (Sigma Cat #C4765), 250 μM IBMX, 1× GlutaMAX™ (Gibco Cat #35050), and 20 mM HEPES (HyClone Cat #SH30237.01) in a 20 μl assay volume. After incubating for 60 minutes at room temperature, the resulting increase in intracellular CAMP is quantitatively determined using the CisBio CAMP Dynamic 2 HTRF Assay Kit (62AM4PEJ). The Lysis buffer containing cAMP-d2 conjugate (20 μl) and the antibody anti-cAMP-Eu3+-Cryptate (20 μl) are then added to determine the cAMP level. After incubating 60 minutes at room temperature, HTRF signal is detected with an Envision 2104 plate reader (PerkinElmer). Fluorescent emission at 620 nm and at 665 nm is measured and the ratio between 620 nm and at 665 nm is calculated and then are converted to nM cAMP per well using a cAMP standard curve. Dose response curves of compounds are plotted as the percentage of stimulation normalized to minimum (buffer only) and maximum (maximum concentration of each control ligand) values and analyzed using a four parameter non-linear regression fit with a variable slope (Genedata Screener 13). EC50 is the concentration of compound causing half-maximal simulation in a dose response curve. A relative $EC_{50}$ value is derived by non-linear regression analysis using the percent maximal response vs, the concentration of peptide added, fitted to a four-parameter logistic equation.

Using Homogeneous Time Resolved Fluorescence methods, assays are conducted to determine the intrinsic potency of Example and comparator molecules performed in the presence of casein (instead of serum albumin) as a nonspecific blocker, which does not interact with the fatty acid moieties of the analyzed molecules.

Intracellular cAMP levels are determined by extrapolation using a standard curve. Dose response curves of compounds are plotted as the percentage of stimulation normalized to minimum (buffer only) and maximum (maximum concentration of each control ligand) values and analyzed using a four-parameter non-linear regression fit with a variable slope (Genedata Screener 13). $EC_{50}$ is the concentration of compound causing half-maximal simulation in a dose response curve. Each relative EC50 value for the geometric mean calculation is determined from a curve fitting.

Concentration response curves of compounds are plotted as the percentage of stimulation normalized to minimum (buffer only) and maximum (maximum concentration of each control ligand) values and analyzed using a four-parameter non-linear regression fit with a variable slope (Genedata Screener 13). EC50 is the concentration of compound causing half-maximal simulation in a dose response curve. The $EC_{50}$ summary statistics are computed as follows: Geometric mean:

GM=10(arithmetic mean of $\log_{10}$ transformed $EC_{50}$ values). The standard error of the mean is reported:

$$SEM = \text{geometric mean} \times (\text{standard deviation of } \log_{10} \text{ transformed } EC_{50} \text{ values/square root of the \# of runs}) \times \log_e \text{ of } 10.$$

The log transform accounts for the $EC_{50}$ values falling on a multiplicative, rather than an arithmetic scale.

Each time the assay is performed, the test peptides are run plus the native ligands GIP, GLP-1, and glucagon, buffer only as baseline (minimum) and the highest concentration of the respective GIP, GLP-1, and glucagon standard is used as maximum for calculations. For illustration, as shown by Example 1, the peptide is tested in 8 runs of the hGIPR CAMP assay. For avoidance of doubt, hGIP amide, hGLP-1 amide, and glucagon EC50 in Table 2 are illustrative of geometric mean values from a series of 18 assay values, and values will vary each day compared to the zero buffer. Accordingly, each Example will use the geometric mean of those values to normalize the Example assay runs.

TABLE 2

Functional activation of hGcgR, hGIPR, and hGLP-1R in the presence of 0.1% Casein.

| Example or Comparator | hGcgR cAMP Rel EC50 nM (SEM, n) | hGIPR cAMP Rel $EC_{50}$ nM (SEM, n) | hGLP1R cAMP Rel $EC_{50}$ nM (SEM, n) |
|---|---|---|---|
| hGIP-$NH_2$ | >5000 (n = 5) | 0.122 (0.00449, n = 494) | >500 (n = 3) |
| hGlucagon | 0.0116 (0.000315, n = 306) | | 9.79 (1.83, n = 3) |
| hGLP-1 (7-36) $NH_2$ | >500 (n = 4) | | 0.0549 (0.00149, n = 490) |
| 1 | 575 (369, n = 4) | 0.0476 (0.0253, n = 8) | >5000 (n = 5) |
| 2 | 608 (n = 11) | 0.0123 (0.00751, n = 15) | >5000 (n = 11) |
| 3 | 1250 (398, n = 6) | 0.0178 (0.00680, n = 9) | >5000 (n = 6) |
| 4 | 1690 (n = 5) | 0.0182 (0.00783, n = 5) | >5000 (n = 5) |
| 5 | >5000 (n = 5) | 0.0148 (0.00434, n = 5) | >5000 (n = 5) |
| 6 | >5000 (n = 4) | 0.0176 (0.00714, n = 14) | >5000 (n = 4) |
| 7 | >5000 (n = 2) | 0.0219 (0.00294, n = 2) | >5000 (n = 2) |
| 8 | 295 (62.9, n = 2) | 0.0268 (0.000153, n = 3) | >5000 (n = 2) |
| 9 | >5000 | 0.165 | >100 |
| 10 | >5000 | 0.611 | >100 |
| 11 | 445 | 0.0738 | >100 |
| 12 | >5000 | 0.0911 | >100 |

TABLE 2-continued

Functional activation of hGcgR, hGIPR, and hGLP-1R in the presence of 0.1% Casein.

| Example or Comparator | hGcgR cAMP Rel EC50 nM (SEM, n) | hGIPR cAMP Rel $EC_{50}$ nM (SEM, n) | hGLP1R cAMP Rel $EC_{50}$ nM (SEM, n) |
|---|---|---|---|
| 13 | >5000 | 0.129 | >100 |
| 14 | >5000 | 0.340 | >100 |
| 15 | >5000 | 0.282 | >100 |
| 16 | >5000 (n = 2) | 0.00937 (0.00210, n = 2) | >5000 (n = 2) |
| 17 | >5000 (n = 2) | 0.0135 (0.00227, n = 2) | >5000 (n = 2) |
| 18 | >5000 (n = 2) | 0.00656 (0.00228, n = 2) | >5000 (n = 2) |
| 19 | >5000 (n = 2) | 0.00992 (0.00148, n = 3) | >5000 (n = 2) |
| 20 | >5000 (n = 2) | 0.00933 (0.00112, n = 3) | >5000 (n = 2) |
| 21 | >5000 (n = 3) | 0.291 (0.0766, n = 4) | >5000 (n = 3) |
| 22 | 1250 (487, n = 3) | 0.0345 (0.00839, n = 4) | >5000 (n = 3) |
| 23 | >5000 (n = 5) | 0.0192 (0.00529, n = 4) | 206 (13.8, n = 4) |
| 24 | >5000 (n = 2) | 0.0699 (0.0155, n = 3) | >5000 (n = 2) |
| 25 | >5000 (n = 2) | 0.0155 (0.00237, n = 3) | 8.39 (2.46, n = 4) |
| 26 | >5000 (n = 2) | 0.00991 (0.00277, n = 2) | 5.69 (2.48, n = 4) |
| 27 | >5000 (n = 2) | 0.0132 (0.000266, n = 2) | >5000 (n = 2) |
| 28 | >5000 (n = 2) | 0.0118 (0.00124, n = 2) | >5000 (n = 2) |
| 29 | >5000 (n = 4) | 0.00679 (0.00193, n = 4) | >5000 (n = 4) |
| 30 | >5000 (n = 4) | 0.00572 (0.00160, n = 4) | >5000 (n = 4) |
| 31 | 1750 (886, n = 3) | 0.0148 (0.00426, n = 3) | >5000 (n = 3) |
| 32 | >5000 (n = 2) | 0.00469 (0.00199, n = 3) | >5000 (n = 2) |
| 33 | >5000 | 0.0551 | >5000 |
| 34 | 913 (586, n = 2) | 0.0177 (0.00478, n = 2) | 462 (321, n = 2) |
| 35 | >5000 | 0.0125 | >5000 |
| 36 | >5000 | 0.0543 | 1080 |
| 37 | >5000 | 0.0360 | 61.1 |
| 38 | >5000 | 0.0368 | 1390 |
| 39 | >5000 | 0.0112 | 3330 |
| 40 | >5000 | 0.0330 | 2330 |
| 41 | >5000 | 0.0281 | 1800 |
| 42 | >5000 | 0.0091 | 815 |
| 43 | >5000 | 0.0154 | 1020 |
| 44 | >5000 | 0.0084 | 1180 |
| 45 | 1690 (n = 2) | 0.0490 (0.000420, n = 2) | >5000 (n = 2) |
| 46 | 863 (n = 2) | 0.0294 (0.0166, n = 2) | >5000 (n = 2) |
| 47 | 757 (492, n = 2) | 0.0234 (0.00230, n = 2) | >5000 (n = 2) |
| 48 | 1360 | 0.0166 | >5000 |
| 49 | 2860 (620, n = 6) | 0.0156 (0.00569, n = 7) | >5000 (n = 6) |
| 50 | 371.0 | 0.0212 | 41.0 |
| 51 | 308.0 | 0.0166 | 24.7 |
| 52 | 337.0 | 0.0194 | >5000 |
| 53 | 344 (136, n = 2) | 0.0194 (0.00603, n = 3) | >5000 (n = 2) |
| 54 | >5000 | 0.0540 | >5000 |
| 55 | >5000 | 0.0170 | >5000 (n = 2) |
| 56 | >5000 | 0.0169 | >5000 (n = 2) |
| 57 | 886 (430, n = 2) | 0.0177 (0.00819, n = 3) | >5000 (n = 2) |
| 58 | >5000 | 0.0183 (0.00544, n = 2) | >5000 |

TABLE 2-continued

Functional activation of hGcgR, hGIPR, and hGLP-1R in the presence of 0.1% Casein.

| Example or Comparator | hGcgR cAMP Rel EC50 nM (SEM, n) | hGIPR cAMP Rel $EC_{50}$ nM (SEM, n) | hGLP1R cAMP Rel $EC_{50}$ nM (SEM, n) |
|---|---|---|---|
| 59 | >5000 | 0.0202 | >5000 |
| 60 | >5000 | 0.0369 | 71 |
| 61 | >5000 | 0.0167 | 192 |
| 62 | >5000 | 0.0116 | 58.2 |
| 63 | 1170 | 0.0398 | >5000 |
| 64 | 3070 | 0.0448 | >5000 |
| 65 | 850 | 0.0346 | >5000 |
| 66 | >5000 | 0.0786 | >5000 |
| 67 | >5000 | 0.0627 | >5000 |
| 68 | 3030 (n = 2) | 0.0768 | >5000 (n = 2) |
| 69 | 803 (237, n = 2) | 0.0302 (0.00976, n = 2) | >5000 |
| 70 | 3560 | 0.0254 | >5000 |
| 71 | 581 | 0.0721 | >5000 |
| 72 | >5000 | 0.0182 | >5000 |
| 73 | >5000 | 0.0151 | >5000 |
| 74 | 627 | 0.0167 | >5000 |
| 75 | 2170 | 0.0182 | >5000 |
| 76 | 1200 | 0.0154 | >5000 |
| 77 | 2660 | 0.0265 | >5000 |
| 78 | 3000 (n = 2) | 0.0125 (0.00185, n = 2) | >5000 (n = 2) |
| 79 | >5000 | 0.0316 | >5000 |
| 80 | >5000 (n = 2) | 0.0777 (0.0223, n = 2) | >5000 (n = 2) |
| 81 | >5000 (n = 2) | 0.0282 (0.00791, n = 2) | >5000 (n = 2) |
| 82 | 3790 (n = 2) | 0.0391 (0.00658, n = 2) | >5000 (n = 2) |
| 83 | >5000 | 0.0432 | >5000 |
| 84 | >5000 | 0.0340 | >5000 |
| 85 | >5000 | 0.0359 | >5000 |
| 86 | >5000 | 0.0300 | >5000 |
| 87 | >5000 | 0.0107 | >5000 |
| 88 | 1670 | 0.0031 | >5000 |
| 89 | >5000 (n = 2) | 0.00687 (0.00245, n = 2) | >5000 (n = 2) |
| 90 | >5000 | 0.0272 | >5000 |
| 91 | 289 | 0.0321 | 530 |
| 92 | >5000 (n = 2) | 0.0191 (0.00110, n = 2) | >5000 (n = 2) |
| 93 | >5000 (n = 2) | 0.00482 (0.000315, n = 2) | 884 (n = 2) |
| 94 | >5000 (n = 4) | 0.00436 (0.00186, n = 4) | 1090 (442, n = 4) |
| 95 | >5000 | 0.0272 (0.0110, n = 2) | >5000 |
| 96 | >5000 | 0.0251 | >5000 |
| 97 | >5000 | 0.0090 | 2510 |
| 98 | >5000 (n = 2) | 0.00718 (0.00331, n = 3) | 649 (369, n = 2) |
| 99 | >5000 | 0.00454 (0.000120, n = 2) | >5000 |
| 100 | >5000 | 0.0224 | >5000 |
| 101 | >5000 (n = 2) | 0.0396 (0.00639, n = 2) | >5000 (n = 2) |
| 102 | >5000 (n = 2) | 0.0166 (0.00337, n = 2) | >5000 (n = 2) |
| 103 | >5000 (n = 2) | 0.0129 (0.00901, n = 2) | >5000 (n = 2) |
| 104 | >5000 | 0.0165 | >5000 |
| 105 | >5000 | 0.0179 | >5000 |
| 106 | >5000 | 0.0140 | >5000 |
| 107 | >5000 | 0.0199 | >5000 |
| 108 | >5000 | 0.0088 | >5000 |
| 109 | >5000 | 0.0113 | >5000 |
| 110 | >5000 | 0.0071 | >5000 |
| 111 | >5000 | 0.0065 | >5000 |
| 112 | >5000 | 0.0041 | >5000 |
| 113 | >5000 (n = 3) | 00.0142 (0.0108, n = 3) | >5000 (n = 3) |
| 114 | >5000 | 0.0075 | >5000 |
| 115 | >5000 | 0.0372 | >5000 |
| 116 | >5000 | 0.0280 | >5000 |
| 117 | >5000 | 0.0617 | >5000 |
| 118 | >5000 | 0.0611 | >5000 |
| 119 | >5000 | 0.0220 | >5000 |
| 120 | >5000 | 0.0228 | >5000 |
| 121 | >5000 | 0.0196 | >5000 |
| 122 | >5000 | 0.0100 | >5000 |

As demonstrated by data in Table 2, Example compounds of the present invention are very potent stimulating cAMP from human GIPR in the presence of 0.1% casein.

In Vivo Studies

Pharmacokinetics in Male Cynomolgus Monkeys

The pharmacokinetics of select Examples are evaluated following a single subcutaneous administration of 50 nmol/kg to male cynomolgus monkeys. Blood samples are collected over 504 hours and resulting individual plasma concentrations are used to calculate pharmacokinetic parameters. Peptide plasma ($K_3$ EDTA) concentrations are determined using a qualified LC/MS method that measured the intact mass of the compound. Each peptide and an analog as an internal standard are extracted from 100% cynomolgus monkey plasma using a protein precipitation method. Instruments are combined for LC/MS detection. Mean pharmacokinetic parameters are shown in Table 3.

TABLE 3

Mean Pharmacokinetic Parameters of peptides Following a Single Subcutaneous Administration of 50 nmol/kg to Male Cynomolgus Monkeys.

| Example | $T_{1/2}$ (hr) | $T_{max}$ (hr) | $C_{max}$/Dose (kg*nmol/L/nmol) | $AUC_{Inf}$/Dose (hr*kg*nmol/L/nmol) | CL/F (mL/hr/kg) |
|---|---|---|---|---|---|
| 1 | 71.1 | 24 | 7.20 | 786 | 1.27 |
| 2 | 51.8 | 6 | 6.92 | 624 | 1.61 |
| 3 | 88.8 | 60 | 12.1 | 1764 | 0.57 |
| 4 | 124 | 6 | 8.71 | 1387 | 0.72 |
| 5 | 128 | 120 | 12.0 | 2262 | 0.44 |
| 6 | 129 | 6 | 7.83 | 1382 | 0.77 |
| 7 | 109 | 9 | 10.1 | 1603 | 0.63 |

Abbreviations:
$T_{1/2}$ = half-life,
$T_{max}$ = time to maximal concentration,
$C_{max}$/dose = maximal plasma concentration divided by dose,
$AUC_{Inf}$/Dose = $AUC_{Inf}$ divided by dose,
CL/F = clearance/bioavailability.
Notes:
Data are the mean, where n = 2/group.

As seen in Table 3, results from this study for Example peptides tested are consistent with an extended pharmacokinetic profile.

Pharmacokinetics in Male Sprague Dawley Rats Following Subcutaneous Administration The pharmacokinetics of select Examples are evaluated following a single subcutaneous (SC) administration of 100 nmol/kg to male Sprague Dawley rats. Blood samples are collected over 168 hours following SC administration. Pharmacokinetic parameters are calculated using individual plasma concentrations. A qualified LC/MS method that measures the intact mass of the Example is used to determine plasma ($K_3$ EDTA) concentrations. Each peptide and an analog as an internal standard are extracted from 100% rat plasma using a protein precipitation method. Instruments are combined for LC/MS detection. Mean pharmacokinetic parameters for the Examples are shown in Table 4.

TABLE 4

Mean (+/−SD) Pharmacokinetic Parameters of peptides Following a Single Subcutaneous Administration of 100 nmol/kg to Male Sprague Dawley rats.

| Example | $T_{1/2}$ (hr) | $T_{max}$ (hr) | $C_{max}$/Dose (kg*nmol/L/nmol) | $AUC_{Inf}$/Dose (hr*kg*nmol/L/nmol) | CL/F (mL/hr/kg) |
|---|---|---|---|---|---|
| 1 | 37.4 | 24 | 3.62 | 280 | 3.57 |
| 2 | 26.9 | 12 | 5.47 | 304 | 3.30 |
| 3 | 24.9 | 12 | 3.03 | 130 | 7.67 |
| 5 | 27.1 | 24 | 4.61 | 239 | 4.20 |
| 6 | 34.8 | 24 | 4.07 | 271 | 3.69 |

Abbreviations:

$T_{1/2}$ = half-life, $T_{max}$ = time to maximal concentration, $C_{max}$/Dose = maximal plasma concentration divided by dose, $AUC_{Inf}$/Dose = $AUC_{Inf}$ divided by dose, CL/F = clearance/bioavailability.

Notes:

Data are the mean, where n = 3/group, except for example 3, where the data is from n = 1 animal.

As seen in table 4, results from this study using these Example peptides are consistent with an extended pharmacokinetic profile.

In Vivo Effect on Insulin Secretion in Male Wistar Rats

Male Wistar rats with femoral artery and femoral vein canulas (Envigo, Indianapolis, IN) (280-320 grams) are single-housed in polycarbonate cages with filter tops. Rats maintained on a 12:12 h light-dark cycle (lights on at 6:00 A.M.) at 21° C. and receive food and deionized water ad libitum. Rats are randomized by body weight and dosed 1.5 mL/kg subcutaneously (s.c.) at doses of 0.3, 1.0, 3, 10, 30, and 100 nmol/kg 16 hours prior to glucose administration then fasted. Animals are weighed and anesthetized with sodium pentobarbital dosed intraperitoneally (i.p.) (65 mg/kg, 30 mg/mL). At time 0, a blood sample is collected into EDTA tubes after which glucose is administered intravenously (i.v.) (0.5 mg/kg, 5 mL/kg). Blood samples are collected for glucose and insulin levels at 2, 4, 6, 10, 20 and 30 min post-intravenous administration of glucose. Plasma glucose levels are determined using a clinical chemistry analyzer. Plasma insulin is determined using an electrochemiluminescence assay (Meso Scale, Gaithersburg, MD). Glucose and insulin AUC are examined compared to the vehicle control with n=5 animals per group. Results are presented (SEM)(N).

TABLE 5

The effect of Example compounds on insulin secretion during intravenous glucose tolerance test.

| | Dose (nmol/kg, s.c.) | | | | | | |
|---|---|---|---|---|---|---|---|
| Example | 0.0 | 0.3 | 1.0 | 3.0 | 10 | 30 | 100 |
| 3 | 38.3 | 43.3 | 45.1 | 53.3 | 64.9 | 116.3 | 133.6 |
| | (8.8)(5) | (0.8)(5) | (8.8)(5) | (6.5)(5) | (9.3)(5) | (28.6)(4) | (16.1)(5) |
| 5 | 35.9 | 36.2 | 45.3 | 80.6 | 122.0 | 144 | 212.7 |
| | (7.5)(5) | (4.4)(5) | (6.1)(5) | (6.4)(5) | (5.9)(5) | (16.4)(5) | (19.4)(5) |
| 6 | 39.5 | 34.7 | 54.2 | 75.8 | 100.2 | 135.4 | 166.5 |
| | (2.2)(5) | (3.6)(5) | (6.8)(5) | (10.3)(5) | (15.6)(5) | (22.9)(5) | (21.6)(5) |

The data provided by Table 5 demonstrate a dose dependent increase in insulin secretion.

TABLE 6

| ivGTT Insulin Secretion shown by the following data: | |
|---|---|
| | Insulin secretion (ivGTT) |
| Example | ($ED_{50}$, nmol/kg) (SEM, n) |
| 3 | 17.1 (n = 1) |
| 5 | 18.4 (n = 1) |
| 6 | 12.9 (n = 1) |

The data provided by Table 6 demonstrate dose dependent increase in insulin secretion.

Immunogenicity Assessment of the Compounds of Examples 1, 2, 3, 5, and 6

The purpose of this study is to determine the relative potential for clinical immunogenicity of Example compounds 1, 2, 3, 5, and 6.

Methods:

CD4+ T Cell Assay: The CD4+ T cell assay is used to compare the compounds of Examples 1, 2, 3, 5, and 6 for a potential to induce an immune response in vivo according to methods known in the art (see, e.g., Jones et al. (2004) J. Interferon Cytokine Res. 24:560-572: and Jones et al. (2005) J. Thromb. Haemost. 3:991-1000), where an assessment of clinically tested monoclonal antibodies and peptides shows some degree of correlation between T cell proliferation observed in vitro and immunogenicity in the clinic. Protein therapeutics that induce less than 30% positive response in the CD4+ T cell proliferation assay are associated with a low risk of immunogenicity. Briefly, to assess the propensity for a clinical immunogenic response to the compounds of Examples 1, 2, 3, 5, and 6, CD8+ T cell-depleted peripheral blood mononuclear cells (PBMCs) are prepared and labeled with carboxyfluorescein diacetate succinimidyl ester (CFSE; Invitrogen) from a cohort of 10 healthy donors with diverse human leukocyte antigen (HLA) class II haplotypes. Each donor is tested in triplicate with 2.0 mL media control, keyhole limpet hemocyanin (KLH: 0.33 μM), and the compounds of Examples 1, 2, 3, 5, and 6 (0.33 μM). Cultures are incubated for 7 days at 37° C. with 5% $CO_2$. On day 7, samples are analyzed by flow cytometry using a BD LSR II Fortessa (Becton Dickinson; Franklin Lakes, NJ), equipped with a high throughput sampler (HTS). Data is analyzed using FlowJo® Software (FlowJo, LLC/TreeStar; Ashland, OR).

Results and Discussion

All donors produce a positive T cell response against KLH (100%). Analysis of the frequency and magnitude of the CD4+ T cell response for Example compounds is shown in Table 7.

TABLE 7

CD4 + T Cell Responses for Example compounds and Positive Control (KLH).

| Example or Comparator | % Donor Response (n = 10) | Median Response Strength in positive donors (CDI) |
|---|---|---|
| KLH | 100% | 164.285 (n = 10) |
| Example 1 | 0% | NA (n = 0) |
| Example 2 | 10% | 2.69 (n = 1) |
| Example 3 | 0% | NA (n = 0) |
| Example 5 | 0% | NA (n = 0) |
| Example 6 | 0% | NA (n = 0) |

Cell Division Index ("CDI"): proportion of divided CD4+ T cells to the total number of CD4+ T cells in stimulated versus unstimulated samples.

These data show that the frequency of positive CD4+ T cell response (CDI>2.5) was low for the tested Example compounds, and the magnitude of the response in the one positive donor from the Example 2 group was low (CDI<3). Thus, based on this assay, these compounds have a low risk of immunogenicity.

We claim:

1. A compound comprising SEQ ID NO:10 or a pharmaceutically acceptable salt thereof.

2. A pharmaceutical composition comprising the compound, or a pharmaceutically acceptable salt thereof, as claimed by claim 1, and at least one pharmaceutically acceptable carrier, diluent, or excipient.

3. The pharmaceutical composition of claim 2, wherein the pharmaceutical composition is suitable for subcutaneous administration.

4. The pharmaceutical composition of claim 2, wherein the pharmaceutically acceptable salt is selected from the group consisting of sodium salt, trifluoroacetate salt, hydrochloride salt, ammonium salt, and acetate salt.

* * * * *